US008709090B2

(12) United States Patent
Makower et al.

(10) Patent No.: US 8,709,090 B2
(45) Date of Patent: Apr. 29, 2014

(54) ADJUSTABLE ABSORBER DESIGNS FOR IMPLANTABLE DEVICE

(75) Inventors: Joshua Makower, Los Altos, CA (US); Clinton N. Slone, San Francisco, CA (US); Alan C. Regala, Mountain View, CA (US); Michael E. Landry, Austin, TX (US); William G. Tammen, San Francisco, CA (US)

(73) Assignee: Moximed, Inc., Hayward, CA (US)

( * ) Notice: Subject to any disclaimer, the term of this patent is extended or adjusted under 35 U.S.C. 154(b) by 665 days.

(21) Appl. No.: 12/113,072

(22) Filed: Apr. 30, 2008

(65) Prior Publication Data

US 2008/0275563 A1 Nov. 6, 2008

Related U.S. Application Data

(63) Continuation-in-part of application No. 11/743,097, filed on May 1, 2007, and a continuation-in-part of application No. 11/743,605, filed on May 2, 2007, and a continuation-in-part of application No. 11/775,139, filed on Jul. 9, 2007, and a continuation-in-part of application No. 11/775,149, filed on Jul. 9, 2007, and a continuation-in-part of application No. 11/775,145, filed on Jul. 9, 2007.

(51) Int. Cl.
*A61F 2/38* (2006.01)

(52) U.S. Cl.
USPC ..................................... 623/20.21; 623/20.14

(58) Field of Classification Search
USPC .......... 623/13.11, 13.12, 13.15, 17.13, 18.11, 623/20.12, 20.21, 20.24; 606/59; 267/70, 267/82, 195, 202, 203–205, 214, 216, 218, 267/224, 225; 276/276; 280/276, 277, 299
See application file for complete search history.

(56) References Cited

U.S. PATENT DOCUMENTS

| 2,632,440 | A | 3/1953 | Hauser |
| 2,877,033 | A | 3/1959 | Koetke |
| 3,242,922 | A | 3/1966 | Thomas |
| 3,648,294 | A | 3/1972 | Shahrestani |
| 3,681,786 | A | 8/1972 | Lynch |

(Continued)

FOREIGN PATENT DOCUMENTS

| CA | 1205602 | 6/1986 |
| DE | 19855254 | 6/2000 |

(Continued)

OTHER PUBLICATIONS

Aldegheri, Roberto, M.D. et al.; "Articulated Distraction of the Hip—Conservative Surgery for Arthritis in Young Patients", Clinical Orthopaedics and Related Research, No. 301, pp. 94-101.

(Continued)

*Primary Examiner* — David Isabella
*Assistant Examiner* — Joshua Levine
(74) *Attorney, Agent, or Firm* — Steptoe & Johnson LLP

(57) ABSTRACT

A system for manipulating energy transferred by members defining a joint. The system includes a first attachment structure configured to be attached to a first member of the joint and a second attachment structure configured to be attached to a second member of the joint. There is also an adjustable energy absorbing device attached to the first attachment structure and second attachment structure, wherein adjusting the energy absorbing device changes the load manipulating characteristics of the energy absorbing device.

17 Claims, 71 Drawing Sheets

(56) References Cited

U.S. PATENT DOCUMENTS

| | | |
|---|---|---|
| 3,779,654 A | 12/1973 | Horne |
| 3,875,594 A | 4/1975 | Swanson |
| 3,902,482 A | 9/1975 | Taylor |
| 3,988,783 A | 11/1976 | Treace |
| 4,187,841 A | 2/1980 | Knutson |
| 4,246,660 A | 1/1981 | Wevers |
| 4,308,863 A | 1/1982 | Fischer |
| 4,353,361 A | 10/1982 | Foster |
| 4,501,266 A | 2/1985 | McDaniel |
| 4,570,625 A | 2/1986 | Harris |
| 4,576,158 A | 3/1986 | Boland |
| 4,621,627 A | 11/1986 | DeBastiani et al. |
| 4,637,382 A | 1/1987 | Walker |
| 4,696,293 A | 9/1987 | Ciullo |
| 4,759,765 A | 7/1988 | Van Kampen |
| 4,776,851 A | 10/1988 | Bruchman et al. |
| 4,846,842 A | 7/1989 | Connolly et al. |
| 4,863,471 A | 9/1989 | Mansat |
| 4,871,367 A | 10/1989 | Christensen et al. |
| 4,883,486 A | 11/1989 | Kapadia et al. |
| 4,923,471 A | 5/1990 | Morgan |
| 4,942,875 A | 7/1990 | Hlavacek et al. |
| 4,959,065 A | 9/1990 | Arnett et al. |
| 4,988,349 A | 1/1991 | Pennig |
| 5,002,574 A | 3/1991 | May et al. |
| 5,011,497 A | 4/1991 | Persson et al. |
| 5,019,077 A | 5/1991 | De Bastiani et al. |
| 5,026,372 A | 6/1991 | Sturtzkopf et al. |
| 5,041,112 A | 8/1991 | Mingozzi et al. |
| 5,100,403 A | 3/1992 | Hotchkiss et al. |
| 5,103,811 A | 4/1992 | Crupi |
| 5,121,742 A | 6/1992 | Engen |
| 5,152,280 A | 10/1992 | Danieli |
| 5,318,567 A | 6/1994 | Vichard |
| 5,352,190 A | 10/1994 | Fischer |
| 5,375,823 A | 12/1994 | Navas |
| 5,405,347 A | 4/1995 | Lee et al. |
| 5,415,661 A | 5/1995 | Holmes |
| 5,456,722 A | 10/1995 | McLeod et al. |
| 5,540,688 A | 7/1996 | Navas |
| 5,575,819 A | 11/1996 | Amis |
| 5,578,038 A | 11/1996 | Slocum |
| 5,601,553 A | 2/1997 | Trebling et al. |
| 5,624,440 A | 4/1997 | Huebner |
| 5,662,648 A | 9/1997 | Faccioli et al. |
| 5,662,650 A | 9/1997 | Bailey et al. |
| 5,681,313 A | 10/1997 | Diez |
| 5,695,496 A | 12/1997 | Orsak et al. |
| 5,716,357 A | 2/1998 | Rogozinski |
| 5,803,924 A | 9/1998 | Oni et al. |
| 5,873,843 A | 2/1999 | Draper |
| 5,928,234 A | 7/1999 | Manspeizer |
| 5,976,125 A | 11/1999 | Graham |
| 5,976,136 A | 11/1999 | Bailey et al. |
| 6,036,691 A | 3/2000 | Richardson |
| 6,113,637 A | 9/2000 | Gill et al. |
| 6,139,550 A | 10/2000 | Michelson |
| 6,162,223 A | 12/2000 | Orsak et al. |
| 6,176,860 B1 | 1/2001 | Howard |
| 6,193,225 B1 | 2/2001 | Watanabe |
| 6,264,696 B1 | 7/2001 | Reigner et al. |
| 6,277,124 B1 | 8/2001 | Haag |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,409,729 B1 | 6/2002 | Martinelli et al. |
| 6,482,232 B1 | 11/2002 | Boucher et al. |
| 6,494,914 B2 | 12/2002 | Brown et al. |
| 6,527,733 B1 | 3/2003 | Ceriani et al. |
| 6,540,708 B1 | 4/2003 | Manspeizer |
| 6,572,653 B1 | 6/2003 | Simonson |
| 6,663,631 B2 | 12/2003 | Kuntz |
| 6,692,497 B1 | 2/2004 | Tormala et al. |
| 6,692,498 B1 | 2/2004 | Niiranen et al. |
| 6,752,831 B2 | 6/2004 | Sybert et al. |
| 6,884,242 B2 | 4/2005 | LeHuec et al. |
| 6,966,910 B2 | 11/2005 | Ritland |
| 6,972,020 B1 | 12/2005 | Grayson et al. |
| 6,997,940 B2 | 2/2006 | Bonutti |
| 7,029,475 B2 | 4/2006 | Pajabi |
| 7,141,073 B2 | 11/2006 | May et al. |
| 7,188,626 B2 | 3/2007 | Foley et al. |
| 7,201,728 B2 | 4/2007 | Sterling |
| 7,235,077 B1 | 6/2007 | Wang et al. |
| 7,235,102 B2 | 6/2007 | Ferree et al. |
| 7,238,203 B2 | 7/2007 | Bagga et al. |
| 7,241,298 B2 | 7/2007 | Nemec et al. |
| 7,252,670 B2 | 8/2007 | Morrison et al. |
| 7,261,739 B2 | 8/2007 | Ralph et al. |
| 7,282,065 B2 | 10/2007 | Kirschman |
| 7,285,134 B2 | 10/2007 | Berry et al. |
| 7,291,150 B2 | 11/2007 | Graf |
| 7,306,605 B2 | 12/2007 | Ross |
| 7,361,196 B2 | 4/2008 | Fallin et al. |
| 2001/0020143 A1 | 9/2001 | Stark et al. |
| 2002/0095154 A1 | 7/2002 | Atkinson et al. |
| 2002/0151978 A1 | 10/2002 | Zacouto et al. |
| 2003/0216809 A1 | 11/2003 | Ferguson |
| 2004/0236329 A1* | 11/2004 | Panjabi .................... 606/61 |
| 2004/0260302 A1 | 12/2004 | Manspeizer |
| 2004/0267179 A1 | 12/2004 | Leman |
| 2005/0049708 A1 | 3/2005 | Atkinson et al. |
| 2005/0085815 A1 | 4/2005 | Harms et al. |
| 2005/0119744 A1 | 6/2005 | Buskirk et al. |
| 2005/0154390 A1 | 7/2005 | Biedermann et al. |
| 2005/0192674 A1 | 9/2005 | Ferree |
| 2005/0261680 A1 | 11/2005 | Draper |
| 2006/0064169 A1 | 3/2006 | Ferree |
| 2006/0178744 A1 | 8/2006 | de Villiers et al. |
| 2007/0043356 A1 | 2/2007 | Timm et al. |
| 2007/0106299 A1 | 5/2007 | Manspeizer |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0198088 A1 | 8/2007 | Biedermann et al. |
| 2007/0198091 A1 | 8/2007 | Boyer et al. |
| 2007/0244483 A9 | 10/2007 | Winslow et al. |
| 2007/0244488 A1 | 10/2007 | Metzger et al. |
| 2007/0288014 A1 | 12/2007 | Shadduck et al. |
| 2008/0015593 A1 | 1/2008 | Pfefferle et al. |
| 2008/0071373 A1 | 3/2008 | Molz et al. |
| 2008/0071375 A1 | 3/2008 | Carver et al. |
| 2008/0097434 A1 | 4/2008 | Moumene et al. |
| 2008/0097441 A1 | 4/2008 | Hayes et al. |
| 2008/0132954 A1 | 6/2008 | Sekhon et al. |
| 2008/0275552 A1 | 11/2008 | Makower |

FOREIGN PATENT DOCUMENTS

| | | |
|---|---|---|
| EP | 0383419 | 8/1990 |
| EP | 0953317 | 4/1999 |
| EP | 1770302 | 4/2007 |
| EP | 1005290 | 2/2008 |
| EP | 1468655 | 5/2008 |
| GB | 1507953 | 4/1978 |
| GB | 2223406 | 4/1990 |
| GB | 2250919 | 10/1993 |
| JP | 59-131348 | 7/1984 |
| JP | 7-100159 | 4/1995 |
| JP | 2532346 | 4/1995 |
| JP | 2000-503865 | 4/2000 |
| JP | 2001-145647 | 4/2000 |
| JP | 2003-102744 | 5/2001 |
| JP | 2006-280951 | 10/2006 |
| JP | 2007-167318 | 7/2007 |
| JP | 2007-167319 | 7/2007 |
| JP | 2007-170969 | 7/2007 |
| RU | 2085148 | 7/1997 |
| RU | 2217105 | 11/2003 |
| RU | 2241400 | 9/2004 |
| SU | 578063 | 11/1977 |
| SU | 578957 | 11/1977 |
| SU | 624613 | 8/1978 |
| SU | 640740 | 1/1979 |

(56) References Cited

FOREIGN PATENT DOCUMENTS

| | | |
|---|---|---|
| SU | 704605 | 12/1979 |
| SU | 719612 | 3/1980 |
| SU | 741872 | 7/1980 |
| SU | 1186204 | 10/1985 |
| SU | 1251889 | 8/1986 |
| SU | 1316666 A1 | 6/1987 |
| SU | 1588404 | 8/1990 |
| SU | 1699441 A1 | 12/1991 |
| SU | 1769868 A1 | 10/1992 |
| WO | WO91/07137 | 5/1991 |
| WO | WO 94/06364 | 3/1994 |
| WO | WO 96/19944 | 7/1996 |
| WO | WO02078554 | 10/2002 |
| WO | WO 2004019831 | 3/2004 |
| WO | WO 2004024037 | 3/2004 |
| WO | WO2006/045091 | 4/2006 |
| WO | WO2006/049993 | 5/2006 |
| WO | WO 2006110578 | 10/2006 |
| WO | WO 2007056645 | 5/2007 |
| WO | WO 2007090009 | 8/2007 |
| WO | WO 2007090015 | 8/2007 |
| WO | WO 2007090017 | 8/2007 |
| WO | WO 2007114769 | 10/2007 |
| WO | WO 2007117571 | 10/2007 |
| WO | WO 2008006098 | 1/2008 |

OTHER PUBLICATIONS

Benzel, Edward; "Qualitative Attributes of Spinal Implants"; in: Biomechanics of Spine Stabilization, 1995.
Buckwalter, Joseph A.; "Joint distraction for osteoarthritis"; The Lancet, Department of Orthopaedic Surgery, University of Iowa Hospitals and Clinics, vol. 347, Feb. 3, 1996, pp. 279-280.
Deie, Masataka, M.D. et al.; "A New Articulated Distraction Arthroplasty Device for Treatment of the Osteoarthritic Knee Joint: A Preliminary Report"; Arthroscopy: The Journal of Arthroscopic and Related Surgery; vol. 23, No. 8 (Aug. 2007): pp. 833-838.
Dienst, M. et al.; "Dynamic external fixation for distal radius fractures"; Clinical Orthopaedics and Related Research, 1997, vol. 338, pp. 160-171.
Hall, J. et al.; "Use of a hinged external fixator for elbow instability after severe distal humeral fracture"; Journal of Orthopaedic Trauma, 2000, vol. 14, No. 6, pp. 442-448.
Klein, D. et al.; "Percutaneous treatment of carpal, metacarpal, and phalangeal injuries"; Clinical Orthopaedics and Related Research, 200, vol. 375, pp. 116-125.
Krakauer, J. et al.; "Hinged device for fractures involving the proximal interphalangeal joint"; Clinical Orthopaedics and Related Research, 1996, vol. 327, pp. 29-37.
Lafeber et al., Unloading Joints to Treat Osteoarthritis, Including Joint Distraction, Current Opinion in Rheumatology 2006, 18;519-525.
Madey, S. et al.; Hinged external fixation of the elbow: optimal axis alignment to minimize motion resistance; Journal of Orthopaedic Trauma, 2000, vol. 14, No. 1, pp. 41-47.

Neel, Michael D, M.D. et al.; "Early Multicenter Experience With a Noninvasive Expandable Prosthesis"; Clinical Orthopaedics and Related Research, 2003, No. 415, pp. 72-81.
Neel, Michael D., M.D.; "Repiphysis—Limb Salvage System for the Skeletally Immature"; Wright Medical Technology, Repiphysis Limb Salvage System, 2004, pp. 1-8.
Nockels, Russ P.; "Dynamic Stabilization in the Surgical Management of Painful Lumbar Spinal Disorders"; Spine, 2005, vol. 30, No. 16S, pp. S68-S72.
Orthofix; "Xcaliber Articulated Ankle"; advertising brochure, May 2004.
Orthofix; "Gentle Limb Deformity Correction"; website pages, http://www.eight-plate.com/, 2008.
Perry, Clayton R. et al.; "Patellar Fixation Protected with a Load-Sharing Cable: A Mechanical and Clinical Study"; Journal of Orthopaedic Trauma, 1988, vol. 2, No. 3, pp. 234-240.
Pollo, Fabian E. et al.; "Reduction of Medial Compartment Loads With Valgus Bracing of the Osteoarthritic Knee"; American Journal Sports Medicine, vol. 30, No. 3, 2002; pp. 414-421.
Sommerkamp, G. et al.; "Dynamic external fixation of unstable reactures of the distal part of the radius"; The Journal of Bone and Joint Surgery; 1994, vol. 76-A, No. 8, pp. 1149-1161.
Uchikura, C. et al.; "Comparative study of nonbridging and bridging external fixators fro unstable distal raduis fractures"; Journal of Orthopaedic Science, 2004, vol. 9, pp. 560-565.
Weisstein. Jason S., M.D. et al.; "Oncologic Approaches to Pediatric Limb Preservation"; Journal of the American Academy of Orthopaedic Surgeons; vol. 13, No. 8, Dec. 2005.
Wilke, Hans-Joachim et al.; "Biomechanical Evaluation of a New Total Posterior-Element Replacement System"; Spine, 2006, vol. 31, No. 24, pp. 2790-2796.
Wilkins, Ross M., M.D. et al.; "The Phenix Expandable Prosthesis"; Clinical Orthopaedics and Related Research, No. 382, pp. 51-58.
Yamamoto, Ei et al.; "Effects of Stress Shielding on the Transverse Mechanical Properties of Rabbit Patellar Tendons"; Journal of Biomechanical Engineering, 2000, vol. 122, pp. 608-614.
Lapinskaya, Valentina Spiridonovna, "Treatment of Diseases and Injuries of Hip Joint Using a Method of Distraction", Kuibyshev Medical Institute, 1990.
Larionov d. Yu, et al., "Medical Devices", Scientific and Technical Bimonthly Journal, May-Jun. 2008.
Lapinskaya, V.S., et al., "An Endoapparatus for Restoration of the Hip Joint", Writers Collective, 2008, UDK 615.472.03:616.728.2-089.28.
Nagai, et al., "B109 Mobility Evaluation of Hip-Joint Nonweight-Bearing Device", The Japan Society of Mechanical Engineers No. 02-26.
Tomita, Naohide, "Development of Treatment Devices for Cartilage Regeneration", BME vol. 16, No. 2.
Lentsner, A.A., et al., "Device for Functional Relief of Hip Joint in Cotyloid Cavity Fracture Cases", Ortop Travmatol Protez. Apr. 1990 (4) 44-6.

* cited by examiner

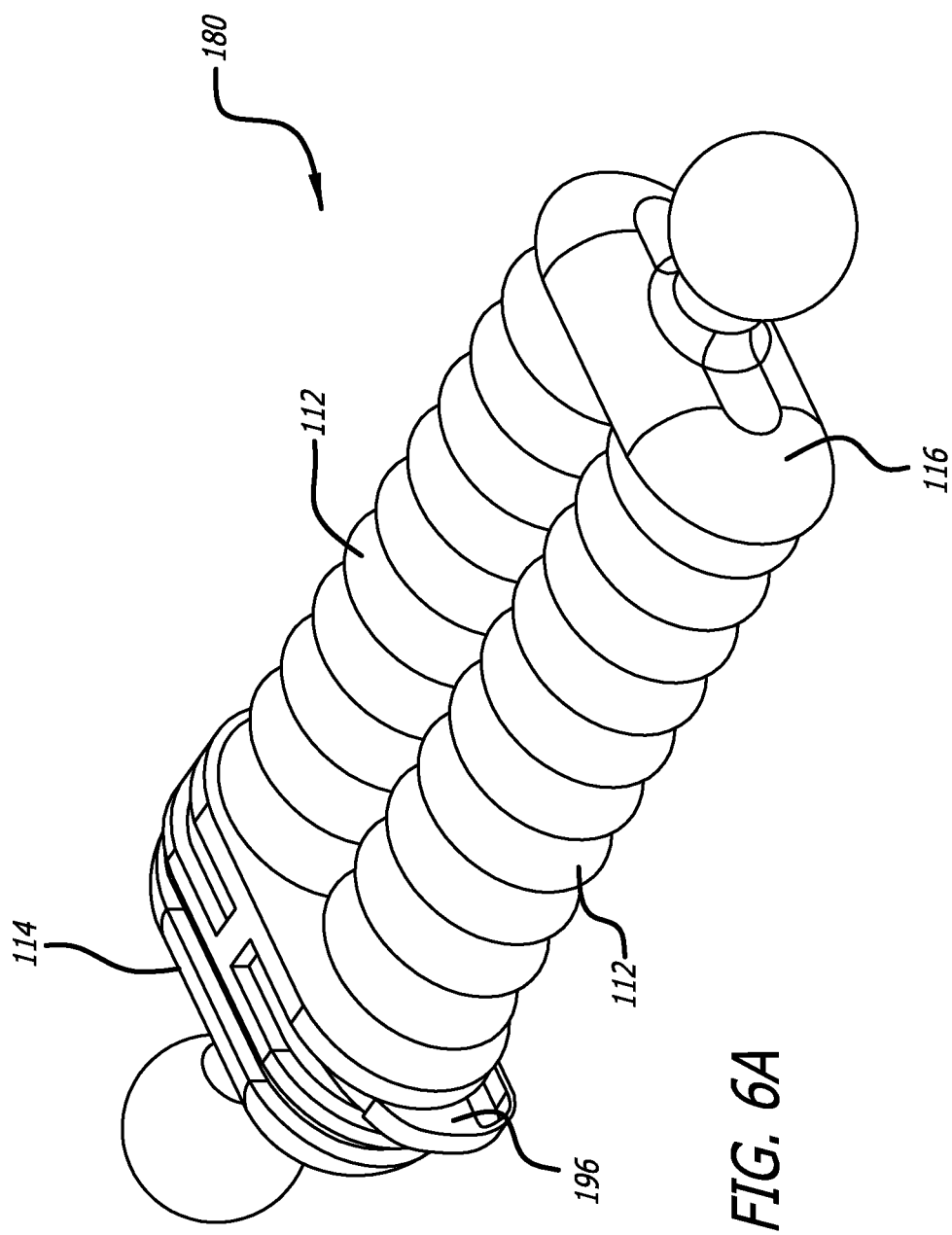

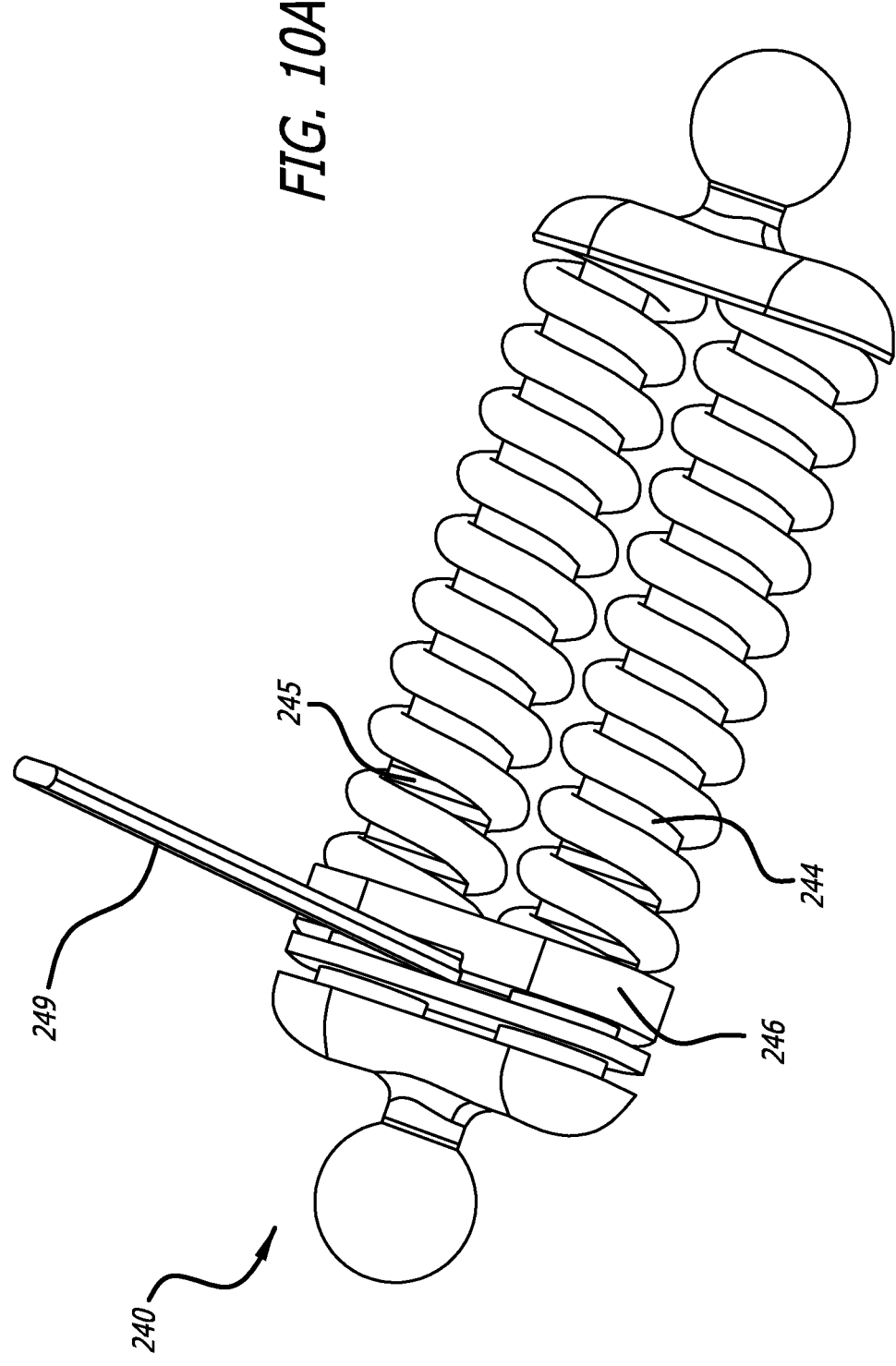

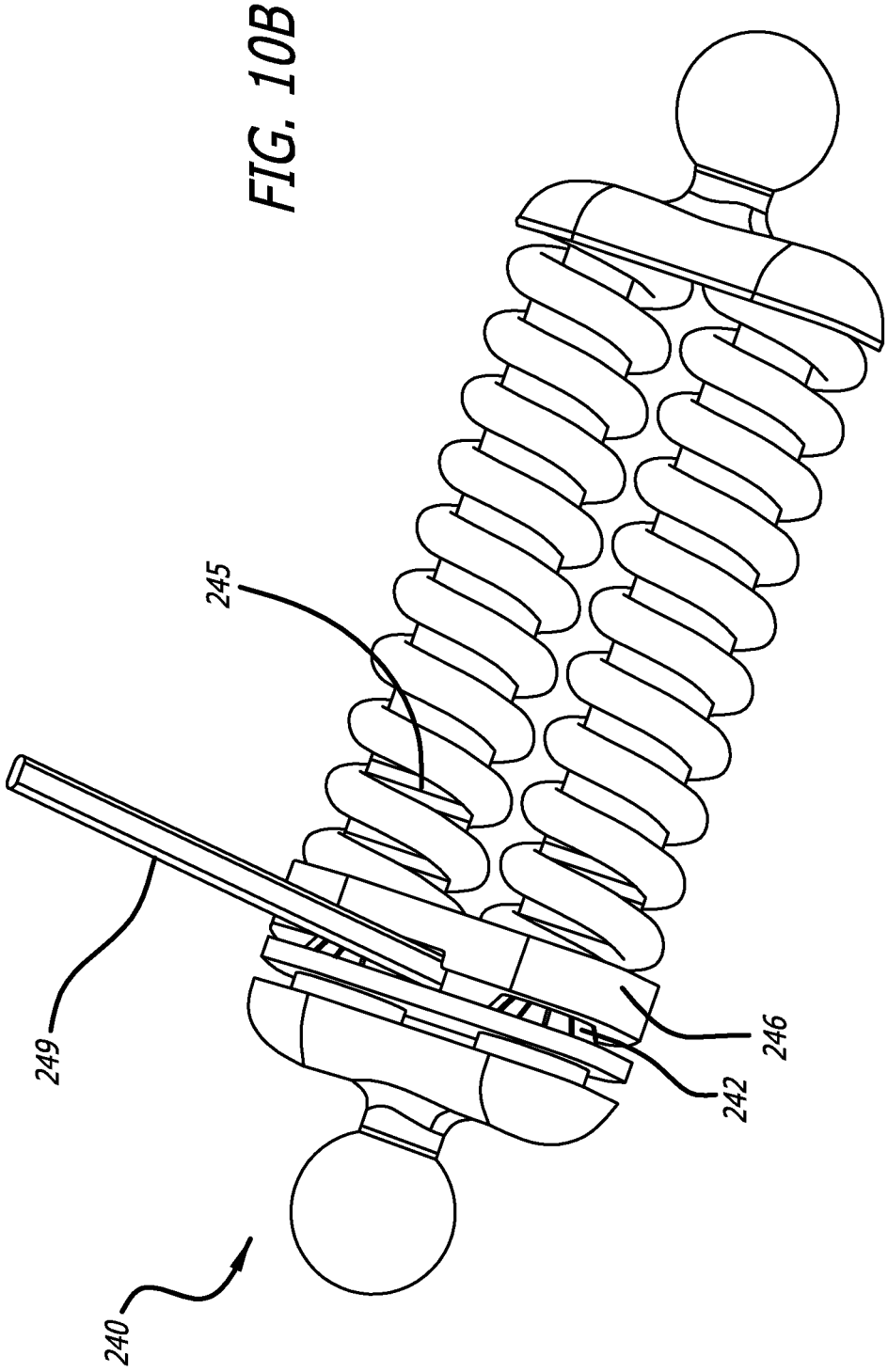

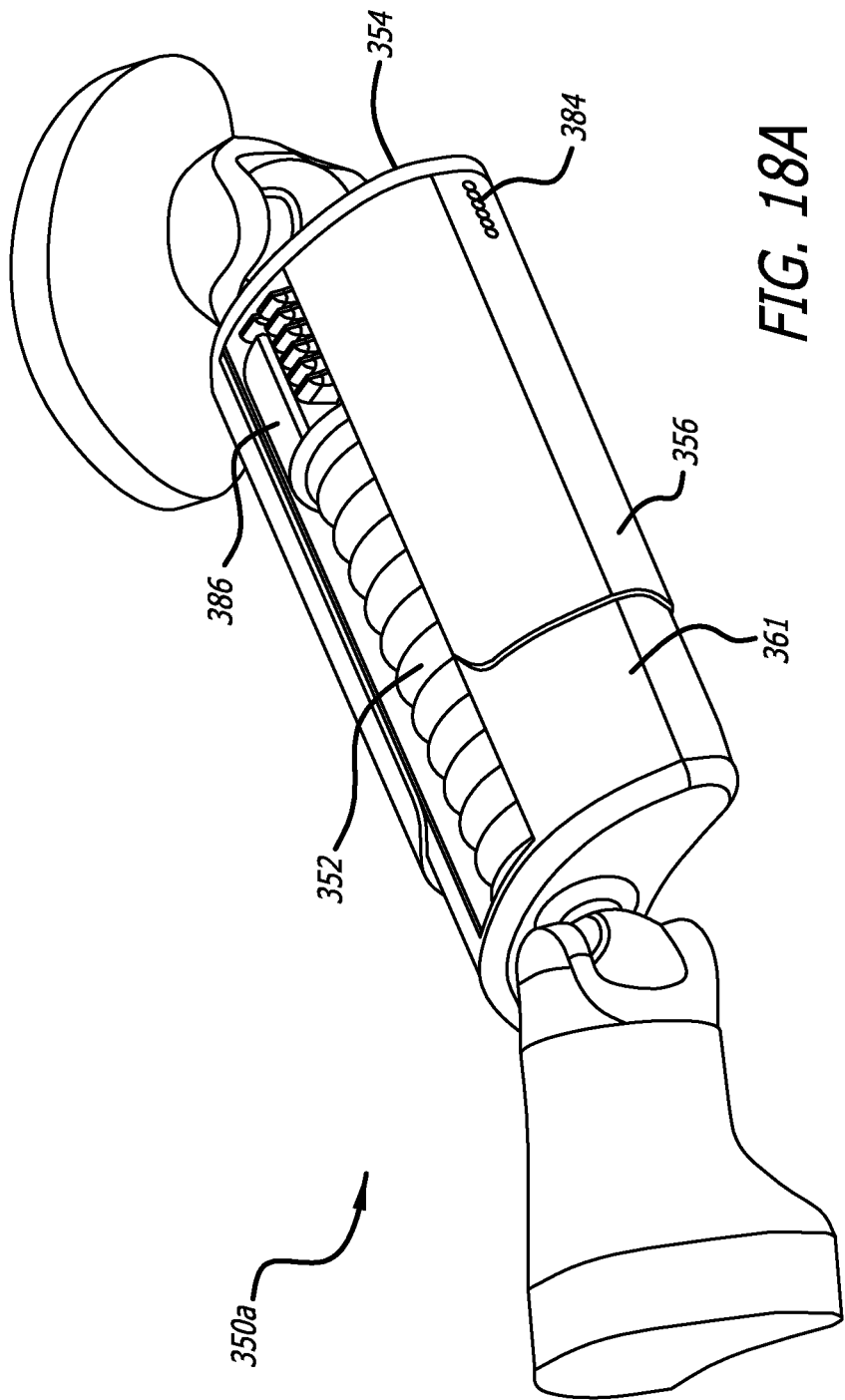

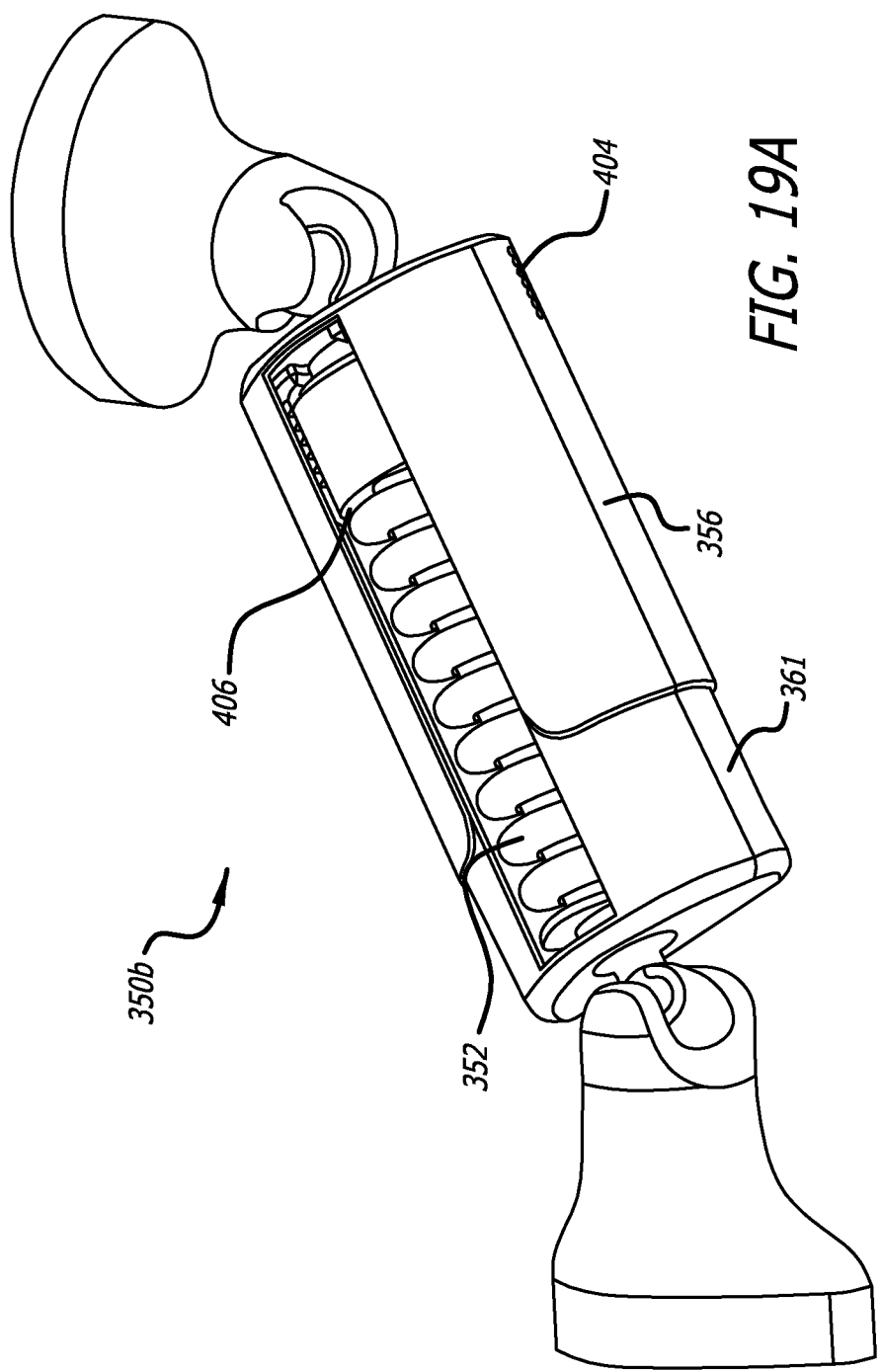

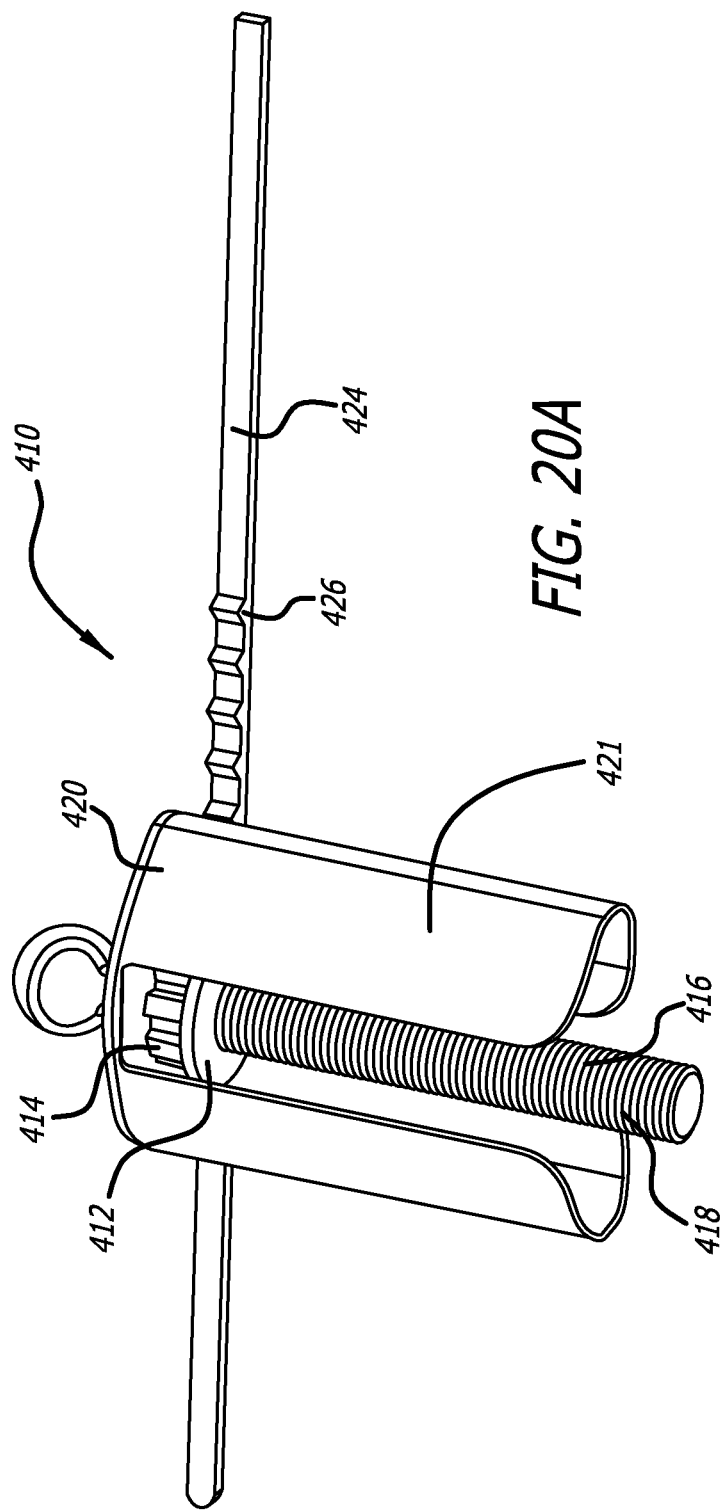

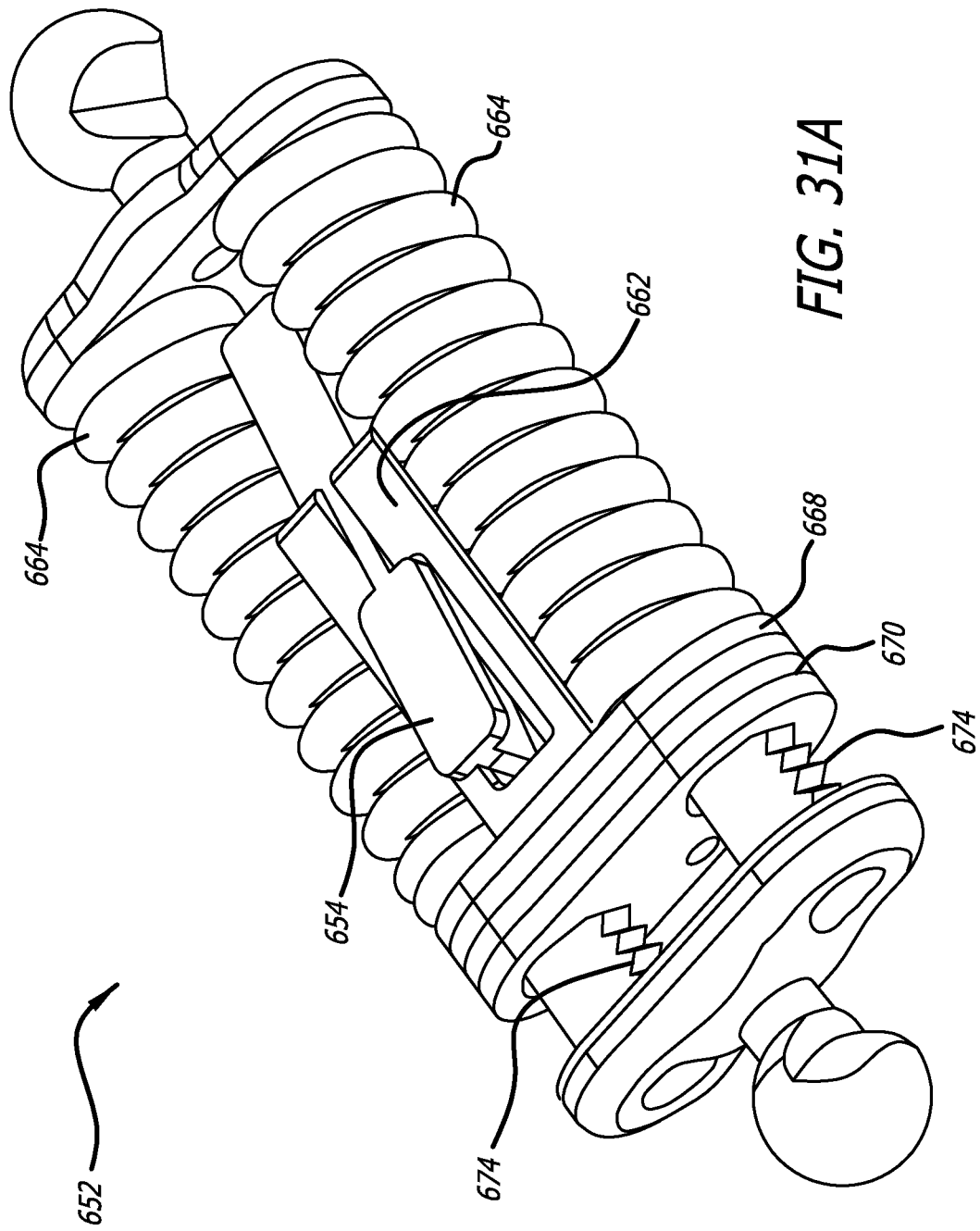

ADJUSTABLE ABSORBER DESIGNS FOR IMPLANTABLE DEVICE

CROSS-REFERENCES TO RELATED APPLICATIONS

This application is a continuation-in-part of U.S. application Ser. No. 11/743,097, filed May 1, 2007, a continuation-in-part of U.S. application Ser. No. 11/743,605, filed May 2, 2007, a continuation-in-part of U.S. application Ser. No. 11/775,139, filed Jul. 9, 2007, a continuation-in-part of U.S. application Ser. No. 11/775,149, filed Jul. 9, 2007 and a continuation-in-part of U.S. application Ser. No. 11/775,145, filed Jul. 9, 2007, the entire disclosures of which are expressly incorporated herein by reference.

BACKGROUND

Joint replacement is one of the most common and successful operations in modern orthopaedic surgery. It consists of replacing painful, arthritic, worn or diseased parts of a joint with artificial surfaces shaped in such a way as to allow joint movement. Osteoarthritis is a common diagnosis leading to joint replacement. Such procedures are a last resort treatment as they are highly invasive and require substantial periods of recovery. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unincompartmental arthroplasty in which the articular surfaces of only one of multiple compartments at a joint (such as the surfaces of the thigh and shin bones on just the inner side or just the outer side at the knee) are replaced. Arthroplasty as a general term, is an orthopaedic procedure which surgically alters the natural joint in some way. This includes procedures in which the arthritic or dysfunctional joint surface is replaced with something else, procedures which are undertaken to reshape or realigning the joint by osteotomy or some other procedure. As with joint replacement, these other arthroplasty procedures are also characterized by relatively long recovery times and their highly invasive procedures. A previously popular form of arthroplasty was interpositional arthroplasty in which the joint was surgically altered by insertion of some other tissue like skin, muscle or tendon within the articular space to keep inflammatory surfaces apart. Another previously done arthroplasty was excisional arthroplasty in which articular surfaces were removed leaving scar tissue to fill in the gap. Among other types of arthroplasty are resection(al) arthroplasty, resurfacing arthroplasty, mold arthroplasty, cup arthroplasty, silicone replacement arthroplasty, and osteotomy to affect joint alignment or restore or modify joint congruity. When it is successful, arthroplasty results in new joint surfaces which serve the same function in the joint as did the surfaces that were removed. Any chondrocytes (cells that control the creation and maintenance of articular joint surfaces), however, are either removed as part of the arthroplasty, or left to contend with the resulting joint anatomy. Because of this, none of these currently available therapies are chondro-protective.

A widely-applied type of osteotomy is one in which bones are surgically cut to improve alignment. A misalignment due to injury or disease in a joint relative to the direction of load can result in an imbalance of forces and pain in the affected joint. The goal of osteotomy is to surgically re-align the bones at a joint and thereby relieve pain by equalizing forces across the joint. This can also increase the lifespan of the joint. When addressing osteoarthritis in the knee joint, this procedure involves surgical re-alignment of the joint by cutting and reattaching part of one of the bones at the knee to change the joint alignment, and this procedure is often used in younger, more active or heavier patients. Most often, high tibial osteotomy (HTO) (the surgical re-alignment of the upper end of the shin bone (tibia) to address knee malalignment) is the osteotomy procedure done to address osteoarthritis and it often results in a decrease in pain and improved function. However, HTO does not address ligamentous instability—only mechanical alignment. HTO is associated with good early results, but results deteriorate over time.

Other approaches to treating osteoarthritis involve an analysis of loads which exist at a joint. Both cartilage and bone are living tissues that respond and adapt to the loads they experience. Within a nominal range of loading, bone and cartilage remain healthy and viable. If the load falls below the nominal range for extended periods of time, bone and cartilage can become softer and weaker (atrophy). If the load rises above the nominal level for extended periods of time, bone can become stiffer and stronger (hypertrophy). Finally, if the load rises too high, then abrupt failure of bone, cartilage and other tissues can result. Accordingly, it has been concluded that the treatment of osteoarthritis and other bone and cartilage conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain but have ultimately been unsuccessful due to lack of patient compliance or the inability of the devices to facilitate and support the natural motion and function of the diseased joint. The loads acting at any given joint and the motions of the bones at that joint are unique to the body that the joint is a part of. For this reason, any proposed treatment based on those loads and motions must account for this variability to be universally successful. The mechanical approaches to treating osteoarthritis have not taken this into account and have consequently had limited success.

Prior approaches to treating osteoarthritis have also failed to account for all of the basic functions of the various structures of a joint in combination with its unique movement. In addition to addressing the loads and motions at a joint, an ultimately successful approach must also acknowledge the dampening and energy absorption functions of the anatomy, and be implantable via a minimally invasive technique. Prior devices designed to reduce the load transferred by the natural joint typically incorporate relatively rigid constructs that are incompressible. Mechanical energy (E) is the action of a force (F) through a distance (s) (i.e., $E=F^x s$). Device constructs which are relatively rigid do not allow substantial energy storage as the forces acting on them do not produce substantial deformations—do not act through substantial distances—within them. For these relatively rigid constructs, energy is transferred rather than stored or absorbed relative to a joint. By contrast, the natural joint is a construct comprised of elements of different compliance characteristics such as bone, cartilage, synovial fluid, muscles, tendons, ligaments, etc. as described above. These dynamic elements include relatively compliant ones (ligaments, tendons, fluid, cartilage) which allow for substantial energy absorption and storage, and relatively stiffer ones (bone) that allow for efficient energy transfer. The cartilage in a joint compresses under applied force and the resultant force displacement product represents the energy absorbed by cartilage. The fluid content of cartilage also acts to stiffen its response to load applied quickly and dampen its response to loads applied slowly. In this way, cartilage acts to absorb and store, as well as to dissipate energy.

With the foregoing applications in mind, it has been found to be necessary to develop effective structures for mounting to body anatomy. Such structures should conform to body anatomy and cooperate with body anatomy to achieve desired load reduction, energy absorption, energy storage, and energy transfer. These structures should include mounting means for attachment of complementary structures across articulating joints.

For these implant structures to function optimally, they must not cause an adverse disturbance to joint motion. Therefore, what is needed is an approach which addresses both joint movement and varying loads as well as complements underlying or adjacent anatomy.

SUMMARY OF THE DISCLOSURE

Briefly and in general terms, the present disclosure is directed towards treating diseased or mal-aligned body joints, typically affected by osteoarthritis, using an adjustable energy absorbing device without limiting the range of motion of the patient's articulating joint. The devices of the present invention accomplish one or more of: absorbing energy during normal gait, reducing load on at least a portion of the natural joint, load transferring or bypassing, energy cushioning, and load sharing or redistribution. In addition, both energy dampening and shock absorption are considered in effecting such load manipulations. Further, the particular anatomy of a patient is considered in the contemplated approaches in that loads on desired portions of anatomy are manipulated without overloading healthy surfaces. In a preferred embodiment, the present invention adds an energy absorber to the joint to reduce energy transferred through the natural joint. One embodiment includes a system for manipulating or absorbing energy transferred by members defining a joint. The system includes a first attachment structure configured to be attached to a first member of the joint and a second attachment structure configured to be attached to a second member of the joint. There is also an adjustable energy absorbing or absorption device attached to the first attachment structure and second attachment structure, wherein adjusting the energy absorbing or absorption device alters the load manipulating or absorbing function of the device. This system may be used to treat a knee joint, or other joint, affected with osteoarthritis and variable amounts of energy absorbing or absorption occurs while the members follow the path of motion of the joint.

The device can be intraoperatively or post-operatively adjusted. For example, the device can be adjusted post-operatively as further or less load manipulation becomes necessary. Moreover, the device can be activated and adjusted to absorb energy to desired degree or can be deactivated so that no energy absorbing occurs such as just subsequent to implantation. In this way, a natural healing process where tissue and bone at the interventional site grows over the implanted structure helps in fixation of the structure prior to activating its load manipulating capabilities. Various approaches are contemplated to accomplish adjustment through a patient's skin. In this regard, components of the device are translated to achieve desired load manipulating as well as to prohibit accidental adjustments of the device. Moreover, feedback systems are incorporated into the device to both indicate translation during adjustment as well as locking and unlocking adjustable components. Such feedback can come in the form of sound or proprioperception.

In one embodiment, the implantable system may include a dual spring energy absorbing device. Still in another embodiment, the system may include a single spring energy absorbing device. In either embodiment, adjusting the compression of the springs/spring alters the character of the load the energy absorption system manipulates in response to articulation of members to which it is attached. The load manipulating profile the system provides may be adjusted during surgery when the energy absorption system is implanted onto a joint, or after a patient has recovered from surgery. Adjustment of the load manipulating characteristics may be performed multiple times as needs and circumstances surrounding the patient change over time. Alternatively, the amount of load the system can manipulate may be adjusted by replacing the springs/spring of the device with springs/spring having a different measure of stiffness.

In other approaches, adjustment is provided by selectively positioning mounts to which absorbers are attached. Moreover, in certain embodiments, adjustment can be provided by adjusting link ends in combination with or to the exclusion of adjusting springs forming the load bearing structure. Adjusting a point of translatable components of a link such that the link does not carry loads beyond a predetermined amount and the natural joint carries the load above that amount is also contemplated so as to control forces being transferred to the bases of an energy absorbing device. Such bases can be made of flexible material for absorbing forces. Additionally, desired adjustment can be achieved through mechanical aspects of a machined spring itself.

In one embodiment of the energy absorbing system, the adjustable energy absorbing device includes an arbor shaft and an adjustable assembly or a collar slidably attached to the arbor shaft. The arbor shaft may be connected to an arbor having an arbor base. The assembly or collar is configured to translate along a portion of the length of the arbor shaft and lock into a position on the shaft. In certain embodiments, the collar may be a split collar, spring loaded collar, a twist and pull locking collar, stop collar, "Grip Fast" collar, or any other collar that can be configured to lock and unlock along a shaft. The assembly or collar may also be any collar configured to translate over threads of the arbor shaft. The adjustable energy absorbing device may also include a piston shaft that slides within a lumen of the arbor shaft. The lumen can pass completely through the arbor base to provide structure suited to avoid the piston from locking up with the arbor shaft. The piston shaft includes a piston that is connected to a base of the piston arbor.

In one embodiment, the adjustable energy absorbing device includes a compression spring disposed over the arbor shaft between the collar and the piston base. Adjusting the position of the collar over the arbor shaft changes the compression of the compression spring, thereby changing a load manipulating profile of the energy absorbing system. In a dual spring embodiment the adjustable energy absorbing device includes a first spring and a second spring disposed over a first arbor shaft and a second arbor shaft, respectively.

In another embodiment, the energy absorbing device may include a spring stop or assembly that is free floating along an arbor shaft between a stationary arbor base and a compression spring. The compression spring is disposed over the arbor shaft between the spring stop or assembly and a piston base. The piston base includes a piston that slides within a lumen of the arbor shaft. To adjust the load manipulating characteristics of the system in this embodiment, the device includes a plurality of shims attached to the arbor base on a pivot disposed adjacent to the spring stop. The shims are configured to be individually rotated and slid in between the arbor base and the spring stop or assembly to move the spring stop or assembly along the arbor shaft towards the piston base, thereby increasing the compression of the spring when a load is applied to the spring. Shims may also be rotated and slid out from between the arbor base and the spring stop or assembly, thereby decreasing the compression of the spring when a load is applied to the spring.

Yet another embodiment of an energy absorbing device includes an arbor having a first shaft and a second shaft, the first and second shafts each having a lumen extending at least partially through each of the first and second shafts. A collar is slidably engaged to the first and second shafts, and the collar is configured to lock into a position along the lengths of the first and second shafts. There is also a piston base having a first piston and a second piston extending from the piston base, with the first and second pistons configured to slide within the lumens of the first and second arbor shafts, respectively. Again, the anchor base can be equipped with through holes in communication with the lumen which received the piston shafts. A first spring is disposed over the first arbor shaft between the collar and the piston base arbor, and a second spring is disposed over the second arbor shaft between the collar and the piston base. Adjusting the position of the collar over the first and second arbor shafts changes the compression of the first and second springs, which alters the load manipulating characteristics of the energy absorbing device.

In one embodiment, the collar of the energy absorbing device may include an adjustment core and an adjustment block being arranged to slidingly engage together. Sliding the adjustment core and adjustment block towards each other unlocks the collar from the first and second arbor shafts. The adjustment core and adjustment block each include an arm extending towards the piston base. In one embodiment, the piston base may include a first piston wall and a second piston wall that extend towards the arbor base, and are configured to slide along the arms of the adjustment core and adjustment block, respectively. Still in another embodiment, the arms of the adjustment core and adjustment block each include a tooth, and the first and second piston walls of the piston arbor include a slot that engage the teeth of the arms to connect the piston walls with the collar.

One embodiment of a method for treating a joint includes attaching a first attachment structure to a first member of the joint and attaching a second attachment structure to a second member of the joint. An energy absorbing device is then attached to the first attachment structure and second attachment structure, and the character of load manipulating of the energy absorbing device is adjusted to meet the needs of the patient. In treating a knee joint, the device can be implanted extra-capsular and/or to variably change knee kinematics.

In one embodiment, adjusting the load manipulating characteristics of the energy absorbing device as a function of the movement of members defining a joint involves translating a collar or assembly over an arbor shaft of the energy absorbing device to change the compression of a spring disposed over the shaft when a load is applied to the spring. The method of adjusting the energy absorbing device may also include removing any load from the spring before translating the collar over the shaft. Load may be removed from the spring by flexing the joint with the system attached to the members of the joint. A load will generally be applied to the spring when the joint is extended. In certain embodiments, adjusting the energy absorbing device may include inserting a tool into the collar or assembly to unlock the collar or assembly, thereby allowing the collar or assembly to translate over the shaft. In other embodiments, the collar or assembly can be unlocked by squeezing or pushing arms or wings associated with the collar or assembly to overcome a spring biasing force that locks the collar or assembly onto the shaft. Once the desired load capability of the device is set by adjusting the absorber or the spring, the collar or assembly is then locked into position along the length of the shaft.

Adjustments may be done through or over the skin of a patient. In some embodiments, an audible sound such as a click is created by the collar or adjustment assembly when it is unlocked or locked to provide feedback to the physician. Also, audible sounds or tactile feedback can be provided to the physician as the collar or adjustment assembly is translated along the length of the shaft. Such feedback can be incorporated both into unlocking the energy absorbing device as well as for translating components of the device to new positions. Structure can be further incorporated into the implanted system to prevent accidental unlocking and/or translation as well as to facilitate translation through the skin. In the latter regard, the motion or placement of members defining the target joint and secondary structures such as a secondary compression spring can be utilized.

Other features of the energy absorbing system and device will become apparent from the following detailed description, taken in conjunction with the accompanying drawings, which illustrate, by way of example, the principles of the embodiments.

BRIEF DESCRIPTION OF THE DRAWINGS

FIG. 6A is a perspective view, depicting one embodiment of an energy absorbing device with a locking collar;

FIG. 10A is a perspective view, depicting another embodiment of an energy absorbing device with a locking collar in a locked configuration;

FIG. 10B is a perspective view, depicting the energy absorbing device of FIG. 10A in an unlocked configuration;

FIG. 18A is a perspective view, depicting another embodiment of a single spring energy absorbing device;

FIG. 19A is a perspective view, depicting an embodiment of a single spring energy absorbing device;

FIGS. 20A and 20B depict partial perspective views showing another embodiment of a single spring energy absorbing device;

FIG. 31A is a perspective view, depicting yet a further embodiment of an energy absorbing device;

DETAILED DESCRIPTION

Figure 1A:
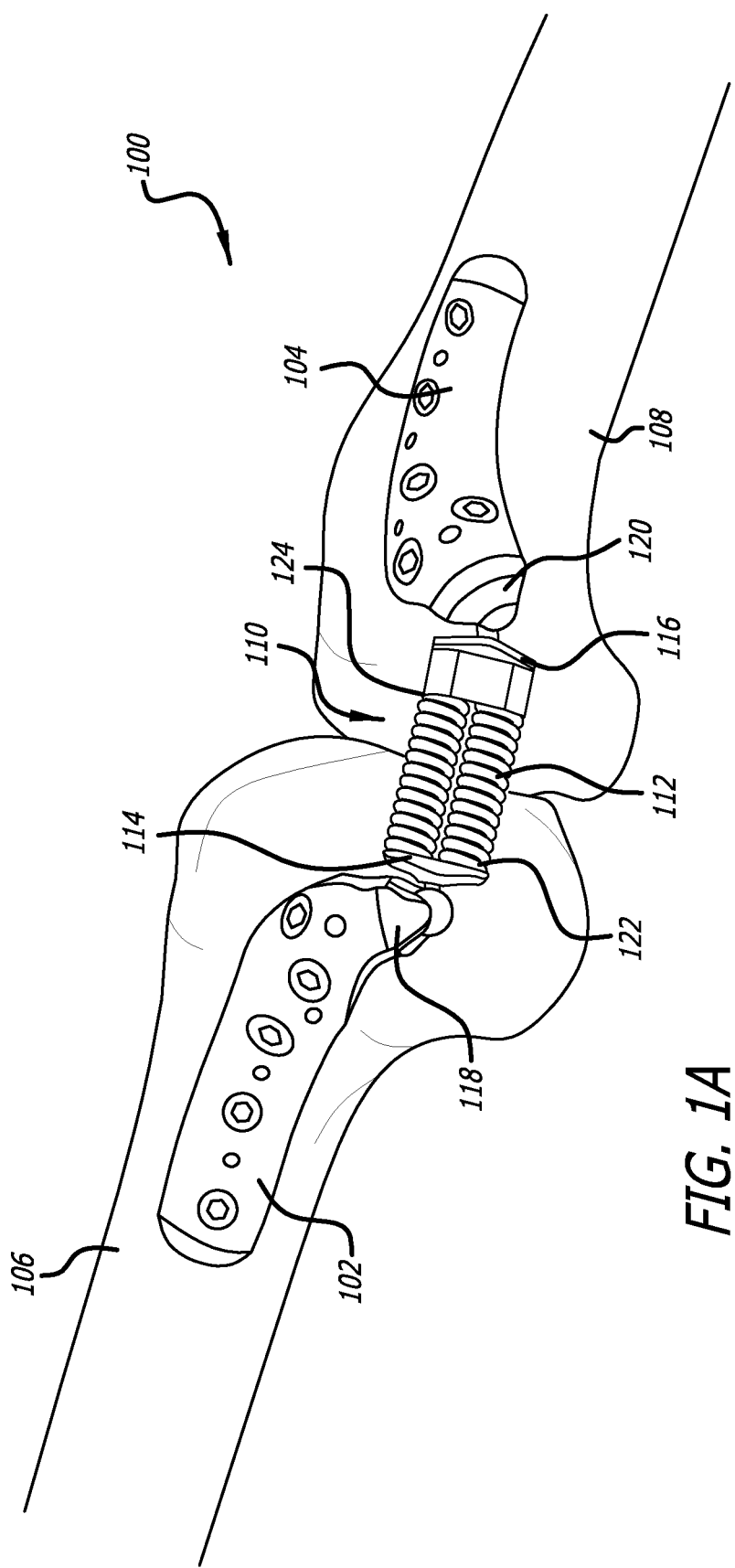
FIG. 1A is a perspective view, depicting an embodiment of an energy absorbing system mounted at a knee joint at full extension.

Referring now to the drawings, which are provided by way of example and not limitation, the disclosed embodiments are directed towards apparatus and methods for treating the knee joint. However, these embodiments may also be used in treating other body joints, and to alleviate pain associated with the function of diseased or misaligned members forming a body joint without limiting the range of motion of the joint. The embodiments described below relate to apparatuses and methods for adjusting the amount of load an energy absorbing device can manipulate. Some embodiments include an energy absorbing device including a dual spring member and other embodiments include the use of a single spring member.

Certain of the embodiments include energy absorbing devices designed to minimize and complement the dampening effect and energy absorption provided by the anatomy of the body, such as that found at a body joint. It has been postulated that to minimize pain, load manipulation or absorption of 1-40% of forces, in varying degrees, may be necessary. Variable load manipulation or energy absorption in the range of 5-20% can be a target for certain applications.

In body anatomy incorporating energy absorbing systems as described below, less forces are transferred to the bones and cartilage of the members defining the joint, and a degree of the forces between body members is absorbed by the energy absorbing system. In one embodiment, the energy absorbing system can be initially configured to eliminate, variably reduce or manipulate loads to a desired degree, and to be later adjusted or altered as patient needs are better determined or change.

In applications to the knee joint, the energy absorbing system can be designed to absorb medial compartment loads in a manner that completely preserves the articulating joint and capsular structures. One embodiment of the present invention is load bypassing knee support system comprised of a kinematic load absorber, two contoured base components and a set of bone screws. The implanted system is both extra articular and extra capsular and resides in the subcutaneous tissue on the medial (or lateral) aspect of the knee. The device is inserted through two small incisions above the medial femoral and tibial condyles. The base components are fixed to the medial cortices of the femur and tibia using bone screws. The energy absorber having a spring value of about twenty pounds can provide therapeutic benefit for patients of 275 pounds or less. Higher spring forces would provide greater reduction in joint load and may correlate to greater symptom (i.e., pain) relief.

It has been recognized that knee forces have multiple components. There are a quadriceps force $F_Q$ and a ground reaction force $F_G$ directed generally longitudinally along a leg and there are lateral compartment forces $F_L$ and medial compartment forces $F_M$. There is, however, no conventional clinical measure of $F_M$ or $F_L$. On the other hand, there are non-axial knee forces which result in a moment being applied across the joint referred to as a knee adduction moment. The knee adduction moment (KAM) can be measured clinically. The measurements are useful as KAM can be considered to be a clinical surrogate measure for knee forces.

It has been further observed that a high knee adduction moment correlates with pain. That is, it would be expected that a group of people with diseased joints having lower KAM may not have pain whereas individuals with a relatively higher KAM would experience pain. Thus, an active reduction of knee adduction moment can reduce pain. The system of the present invention reduces the KAM of the patient.

It has also been found that a medial compartment of a knee of an average person with osteoarthritis can benefit from an absorber set for compression between 1 mm and 10 mm, and preferably 3-6 mm with a spring or absorber element that accommodates a range from 20-60 pounds. In a preferred embodiment, the absorber is set for about 4 mm of such compression and a pre-determined load of about 40 pounds.

In each of the disclosed embodiments, various features can be incorporated from other of the disclosed embodiments. Thus, audible and textile feedback sub-systems can be incorporated in the disclosed embodiments to both indicate translation of load adjustment structure as well as to exhibit locking and unlocking of subcomponents. Moreover, each of the contemplated embodiments can include springs machined to provide desirable energy absorbing which varies as the spring is compressed during various degrees of flexion and extension of joint markers to which the energy absorbing device is attached. The term "spring" is used throughout the description but it is contemplated to include other energy absorbing and compliant structures can be used to accomplish the functions of the invention as described in more detail below. Additionally, any of the various disclosed approaches to achieving adjustment through a patient's skin, either through direct engagement with the energy absorbing device with a tool or by applying forces to the device through the surface of the skin can be incorporated to fill a perceived need.

In certain situations, it has been found to be a benefit to implant the energy absorbing device in an inactivated condition, only later taking steps, perhaps several weeks later, to place the device into an activated state. In this way, the device can become further affixed to bone as the bone and surrounding tissue grows over portions of the device. Accordingly, each of the disclosed embodiments can be so implanted and later activated and adjusted through a patient's skin.

Further, various approaches to adjusting the energy absorbing device are contemplated and disclosed below. That is, various approaches to adjusting structure between piston and arbor structure as well as adjusting mounts to which the piston and arbor structures are configured to engage are disclosed. In the former regard, adjustable collars and adjustable link ends are contemplated approaches.

Figure 1B:
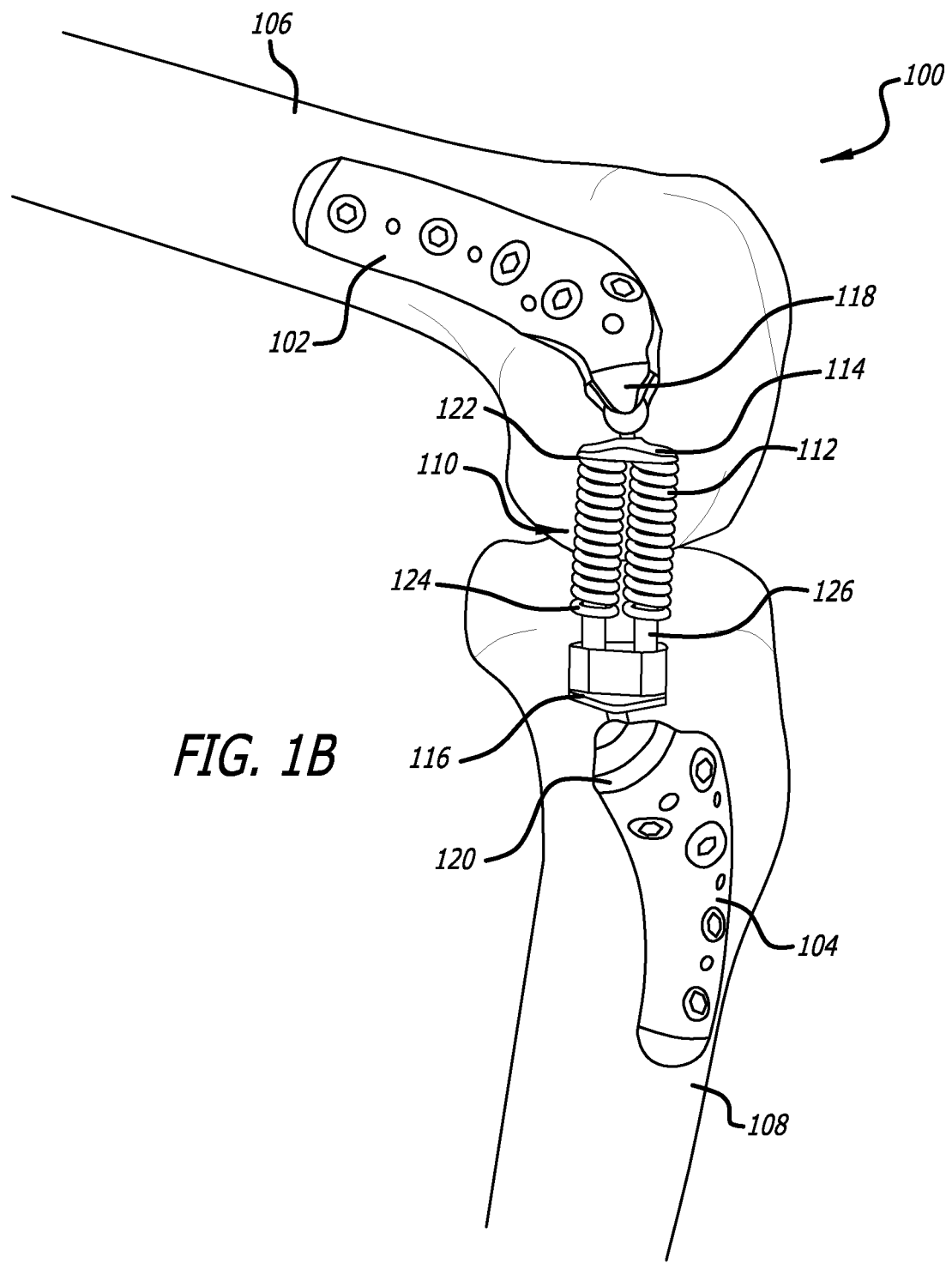
FIG. 1B is a perspective view, depicting the embodiment shown in FIG. 1A with the knee joint flexed to 90°.
Figure 1C:
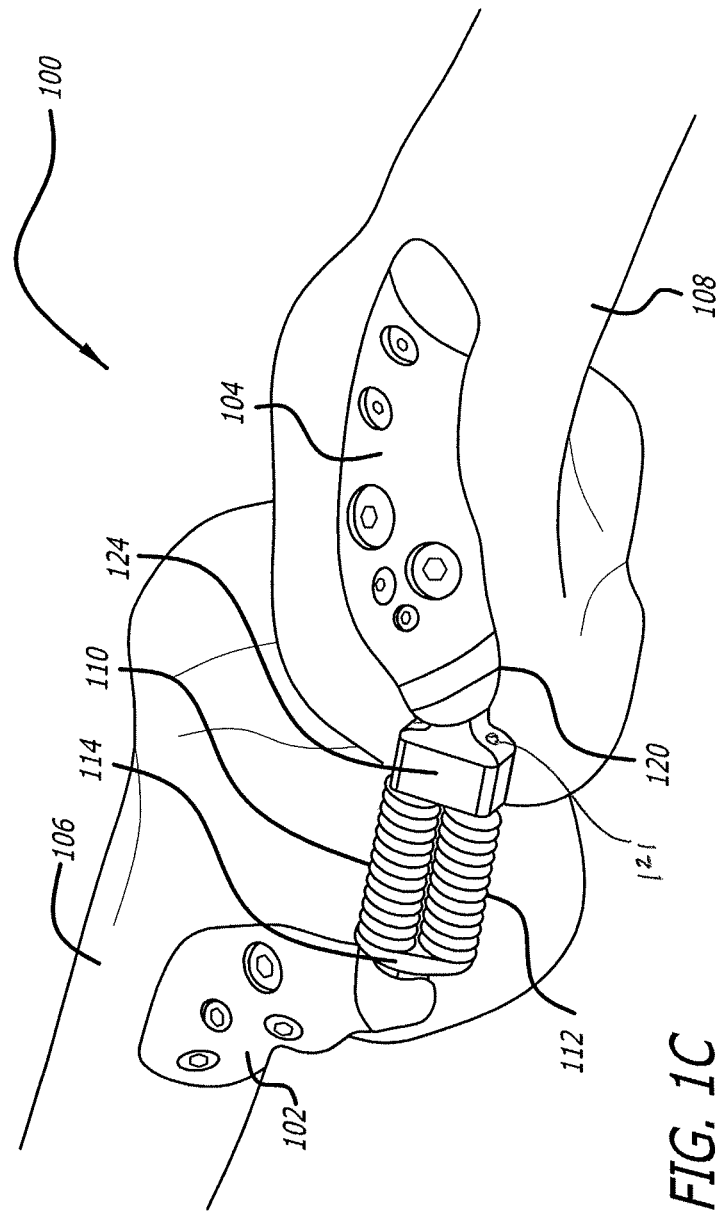
Figure 2A:
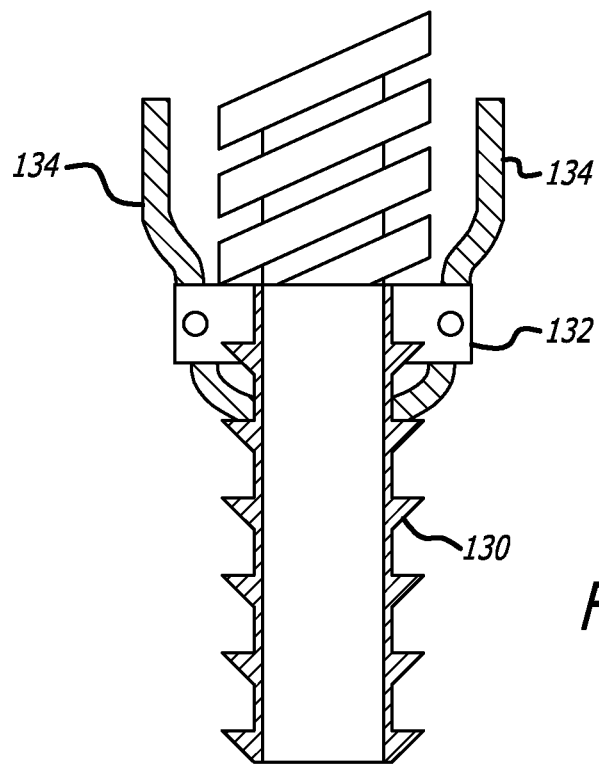
FIG. 2A is a partial cross-sectional view, depicting one embodiment of an adjustment sub-structure.
Figure 2B:
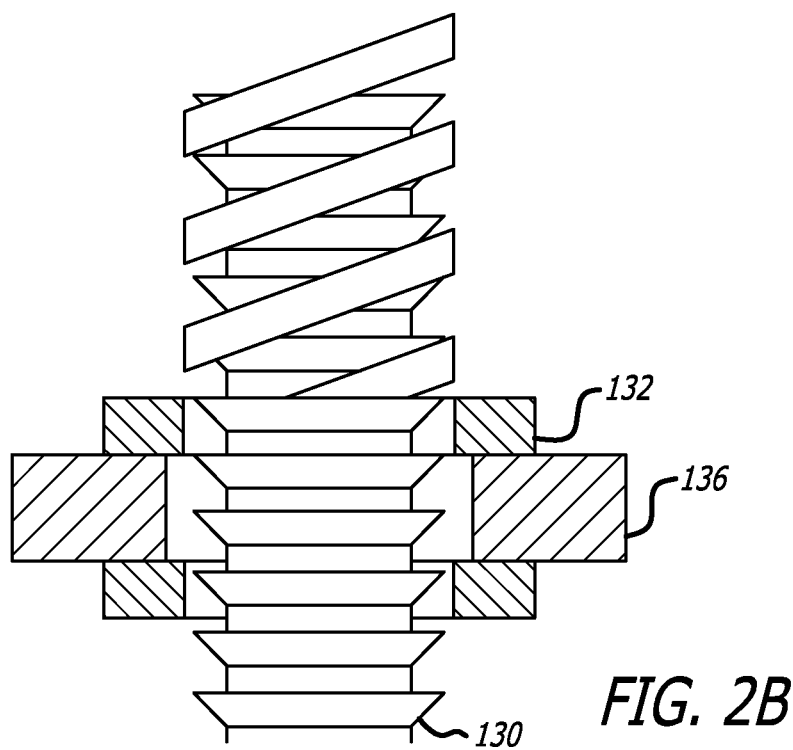
FIG. 2B is a partial cross-sectional view, depicting another embodiment of an adjustment sub-structure.
Figure 2C:
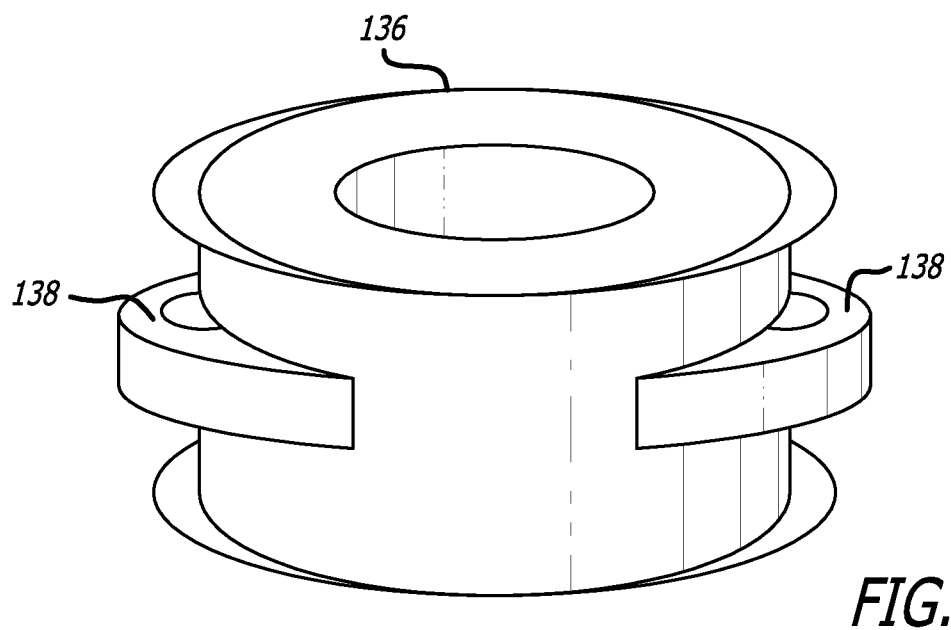
FIG. 2C is an enlarged view, depicting an adjustment ring of FIG. 2B shown in a ratchet engaged state.
Figure 2D:
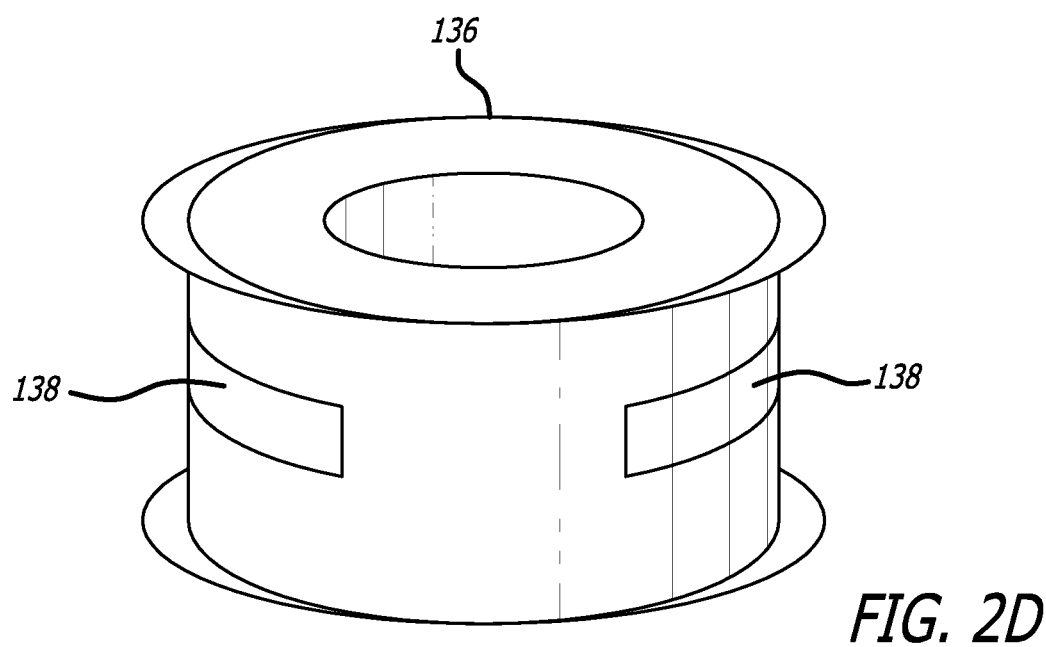
FIG. 2D is an enlarged view, depicting the adjustment ring of FIG. 2C in a ratchet release state.

Referring now to FIGS. 1A-1C, one embodiment of an energy absorbing system 100 is shown with proximal 102 and distal 104 base components positioned upon first 106 and second 108 members, respectively of a typical body joint. Here, the terminal end portions of the femur and tibia are depicted without surrounding tissue. It is noted that portions of the base components are contoured to match potential mounting surfaces of the femur and tibia. Also shown is an energy absorbing device 110 that is configured between and mounted to the base components. FIG. 1A shows the knee joint at full extension with load being applied to springs 112 of the energy absorbing device, whereas FIG. 1B shows the knee joint flexed to 90° with zero load being applied to the springs by virtue of the springs 112 being shorter than the length of the piston shafts 126. The energy absorbing device lengthens as the knee swings from full extension to flexion and subsequently shortens as the knee swings from flexion to full extension such that the springs begin to be compressed between the ends of the device to absorb the load that the knee articulating surfaces normally would experience. The energy absorbing device and base components are mounted across the joint such that once the springs have achieved a predetermined amount of compression, and therefore load, the articulating surfaces of the knee then begin to carry the load in combination with the energy absorbing device such that the energy absorbing device does not "bottom out". The various energy absorbing devices in the present application are shown without a protective covering or sheath but it is contemplated that they can be within a protective covering or sheath to protect the moving elements from impingement by surrounding tissues and to prevent the devices from damaging surrounding tissue.

Still referring to FIGS. 1A-1C, one embodiment of an energy absorbing device 110 includes a piston base 114 and an arbor base 116. The piston base is connected to a first or proximal mount 118 that is in connection with the proximal or first base component 102. On the other end of the energy absorbing device, the arbor base is connected to a second or distal mount 120 that is in connection with the distal or second base component 104. As shown in FIG. 1C, holes 121 are formed in the arbor base 116 to allow and/or contract fluid flow through the arbor during motion. A valve can be added to convert the structure into a pneumatic absorber. A first or proximal end 122 of the springs 112 is in connection with or in contact with the piston base, and a second or distal end of the springs are in contact with a spacer 124 when the knee joint is extended as shown in FIG. 1A. The size of the spacer 124 can be adjusted to affect the amount of compression of the springs. Also, the spacer 124 can be formed of material providing compliance or spring behavior for added energy absorbing or as a built-in overload safety mechanism.

During flexion and extension of the knee joint, piston shafts 126 (not shown) of the piston base slide within arbor shafts (See FIG. 1B) of the arbor base. Although two compression springs are shown in the energy absorbing device, one or more springs may be used. The configuration of the springs may be varied to minimize device size while maximizing its energy absorbing capabilities. Moreover, various types of springs such as coaxial or leaf springs can be employed and the spring structure can be placed serially and adjusted one by one.

The energy absorbing system has the capacity to absorb energy in addition to transfer energy from the joint. The energy absorption of the dual or single spring can be expressed as the product of force and displacement. Although actual springs are used to show various embodiments, these elements could also be substituted with a material or other device with spring-like characteristics (e.g., an elastomeric member). Such elastomers include thermoplastic polyurethanes such as Tecoflex, Tecothane, Tecoplast, Carbothene, Chronthane and ChronoFlex (grades AR, C, AL) which also could be employed as a dampener. Moreover, materials such as Pebax, C-flex, Pellathane and silicone and silicone foam can also be employed.

In other embodiments, the energy absorbing device may include dampening devices such as dash pots. In these embodiments, the spring element is a storage or absorber device while the dashpot acts to dissipate the energy. Such embodiments or other structure defining a shock absorber which alter the velocity of displacement of the spring can be employed to thereby alter the energy absorption behavior. Although more traditional dampening devices may be used with the energy absorbing device, these elements could also be substituted with a material or other device with dampening characteristics (e.g., a small pore sponge).

For one embodiment of system 100, a pre-operative session is performed to assess the need at a joint and to map the articulation of the members 106 and 108 forming the joint. Attachment sites are also assessed pre-operatively. During surgical intervention, a first center of rotation location is identified along the first member of a joint. Next, access is gained to an area proximate the first center of rotation location and the first base component 102 is fixed upon the first member in a manner maintaining use of the first center of rotation location. A second rotation location is then identified along the second member of a joint and surgical access is obtained proximate the second rotation location. Subsequently, the second base component 104 is fixed along the second member while maintaining use of the second rotation location. A subcutaneous channel is created between the first center of rotation and second rotation locations and the energy absorbing device 110 is inserted within the channel. The energy absorber is thereafter mounted to the bases. A tissue barrier, such as a sheath, may be placed about the energy absorber to protect joint anatomy or exclude the device from surrounding tissue. The connection of the absorber 110 to the bases 102 and 104 through attachable/detachable mounts 118 and 120 provides a method for good attachment of the base to the bone and a more simple surgical technique for installing the absorber. It also allows a sheath and/or the wear components of the absorber/mount assembly to be removeable and/or replaceable without removing or replacing the base components. It further allows the wear components of the absorber/mount assembly and the base components to be different materials. For example, the base components can be titanium or titanium alloy which promote osteo-integration and the wear components can be much harder materials such as cobalt chrome (e.g., Biodur CCM Plus), ceramic, or other durable materials that produce a minimal amount of particulate material or, if particulate material is generated, the smallest size of particulate material.

In a contemplated method, the energy absorbing device 110 can be initially configured to eliminate or reduce loads to a desired degree, and to be later adjusted or altered as patient needs are better determined or change. Accordingly, postoperative alterations are contemplated as are adjustments resulting from changing the diameter of a dampening component or a spring rate of a device. In this regard, it is also contemplated there be no initial or load manipulation until the interventional site heals and the device is firmly implanted or during an initial treatment episode to substantially reduce the effects and pain associated with a patient afflicted with osteoarthritis for a long time. The device can provide distraction forces and carry all of the load to an extent that the joint surfaces do not experience load when the joint is fully load bearing. This distraction can continue for up to three months (or preferably two months) and then later the device can be adjusted to accomplish energy absorption without distraction. Moreover, as needs change, the method can involve removal or replacement of one or more components of the energy absorbing assembly. Further, various degrees of non-invasive approaches can be employed as is practical for a given interventional procedure. Additional details and other embodiments of an energy absorbing system and method of implantation are shown and described in U.S. application Ser. No. 11/775,149, which has already been incorporated by reference.

Turning now to FIGS. 2A-D, there is shown approaches to adjusting the energy absorbing device 110. In the approaches depicted, the device includes an arbor shaft 130 including outwardly projecting and angled teeth. The shaft may form part of the arbor base 116. A spring-biased collar assembly 132 is further provided and configured in a lockable arrangement with the shaft. In a first approach (FIG. 2A), the collar assembly 132 is further provided with spring biased buttons 134 (here shown biased in a closed position by an elastomeric ring) having a distant terminal end. As the buttons are each depressed inwardly, this engagement with the teeth of the shaft disengages, thereby allowing the assembly 132 to move up or down. As the assembly 132 is so translated an audible sound is made between the detents of the buttons and the shaft 130. An observable tactile response can also be produced to alert the operator that motion has occurred. Such feedback is contemplated to be incorporated into each of the disclosed embodiments.

In a second approach (See FIGS. 2 B-D), the spring-biased collar assembly 132 is equipped with a two piece collar spring 136 which can assume both ratchet engaged (FIG. 2C) and ratchet released (FIG. 2D) configurations. Thus, by pressing on the spring arms 138 of this embodiment of the spring-biased collar assembly, the collar disengages from the shaft 130 and is permitted to be translated longitudinally. As a safety measure, it is to be appreciated that the angle and length of the teeth formed on the shaft and corresponding engaging structures of the collar assemblies can be configured to only allow translation if two points of the collar are sufficiently pressed.

In these embodiments, moving the spring biased collar assembly 132 proximally towards the first base component 102 changes the stored potential energy in the spring 112. If it is determined during or any time after surgery that the energy absorbing system should be adjusted, the collar/piston assembly is moved distally towards the first base component 102 to further compress the spring between the collar assembly and the piston base 114.

Figure 3A:
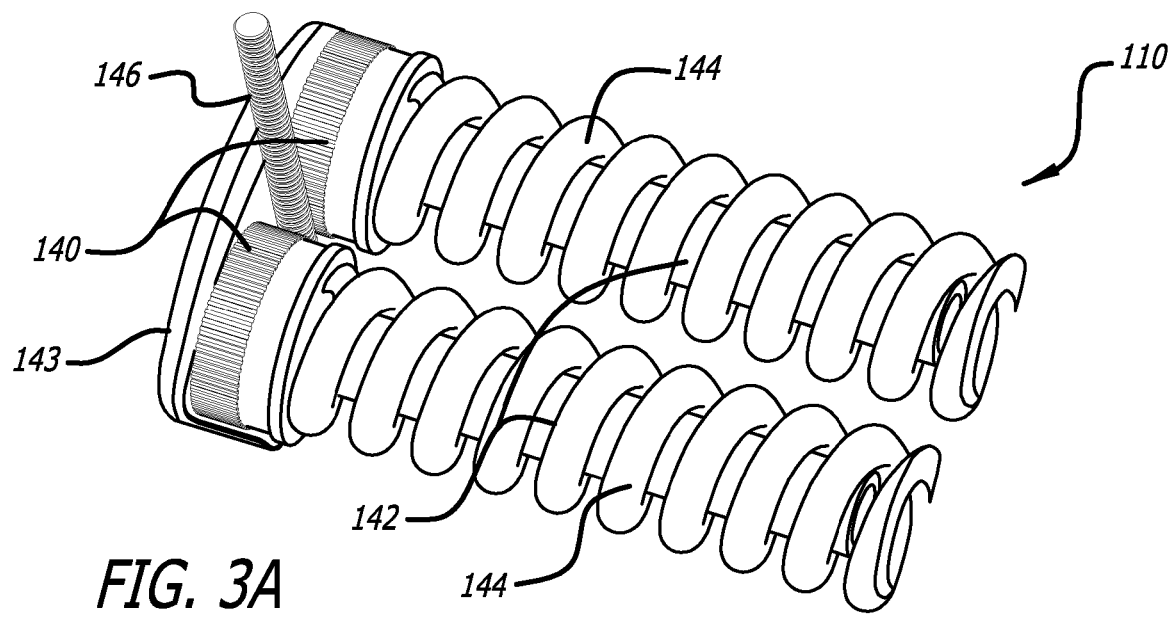
FIGS. 3A and 3B are partial views, depicting one embodiment of an energy absorbing device.
Figure 3B:
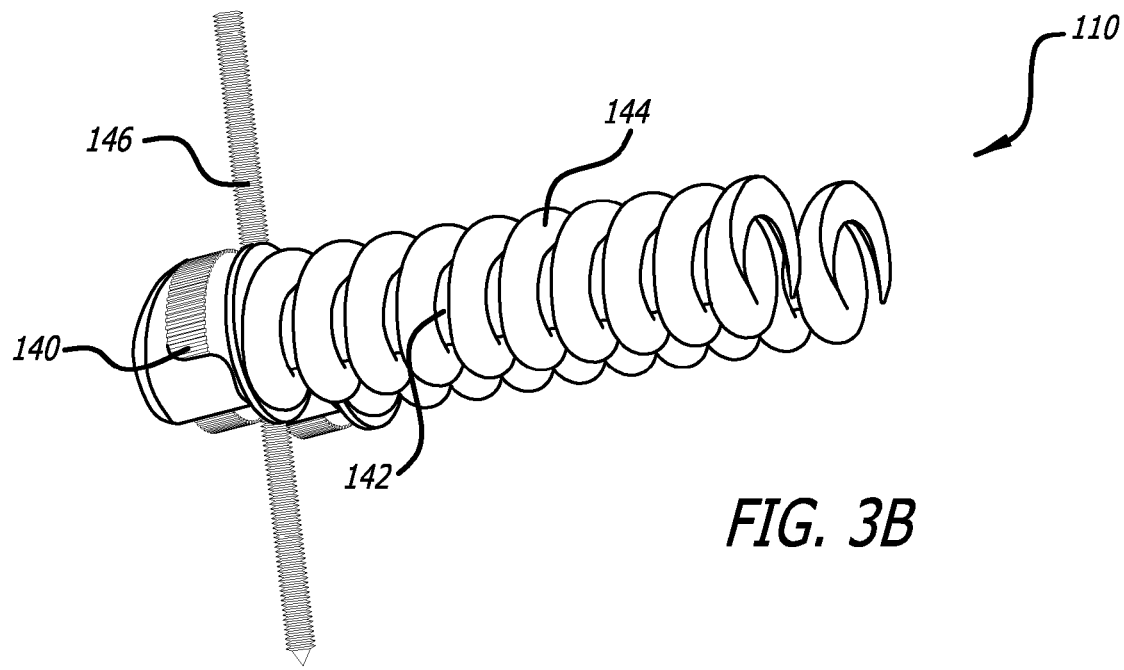

Another embodiment of adjusting the energy absorbing device 110 is shown in FIGS. 3A and 3B. In this embodiment, the device includes two oppositely threaded spring stops 140 configured in a lockable arrangement with arbor shafts 142 of an arbor base 143, the arbor shafts having threads or teeth. To adjust springs 144 of the device, a rod 146 with teeth can be inserted in one of two directions between the two spring stops to create rotation of the spring stops. Rotation in one direction translates the spring stops proximally towards the arbor base, thereby decreasing the stored potential energy in the spring 142. Rotation of the stops in the opposite direction compresses the spring between the stops and the piston base (not shown) when a load is applied to the spring. It has also been contemplated that the rod could be threaded and either permanently located in between the stops and rotated via a hex tool, or other tool, or inserted only during time of adjustment.

Figure 4A:
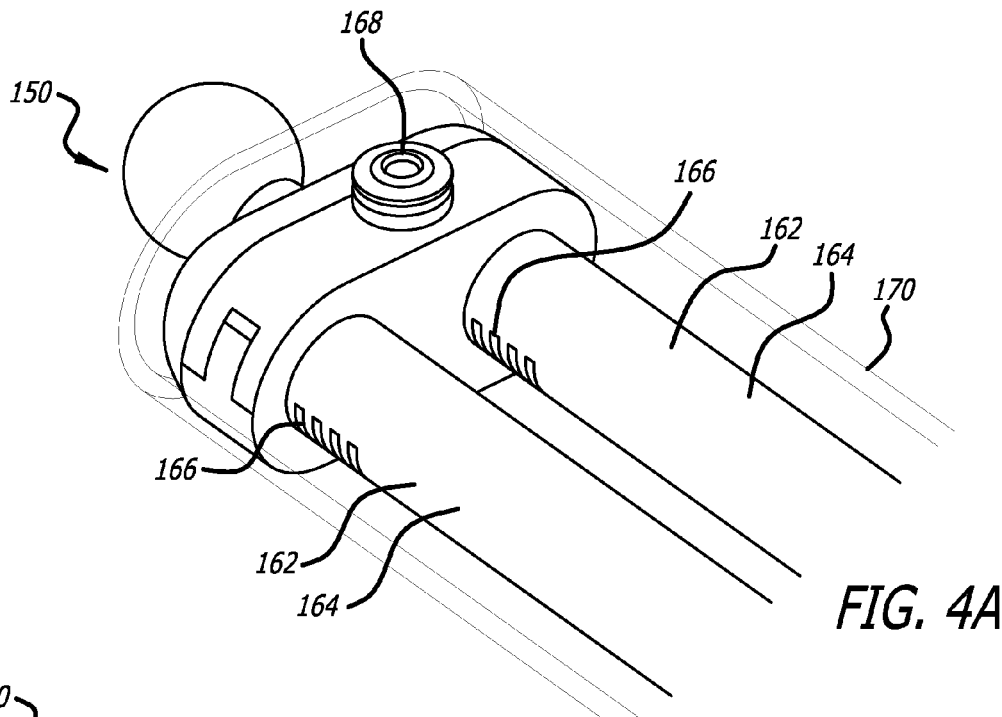
FIG. 4A is a partial perspective view, depicting one embodiment of an energy absorbing device with a split collar.
Figure 4B:
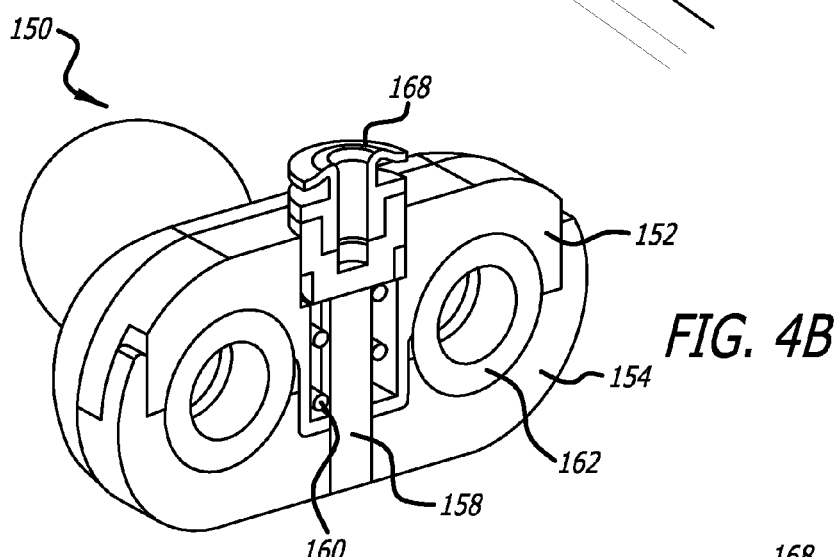
FIG. 4B is a cross-sectional view of the split collar shown in FIG. 4A in a locked configuration.
Figure 4C:
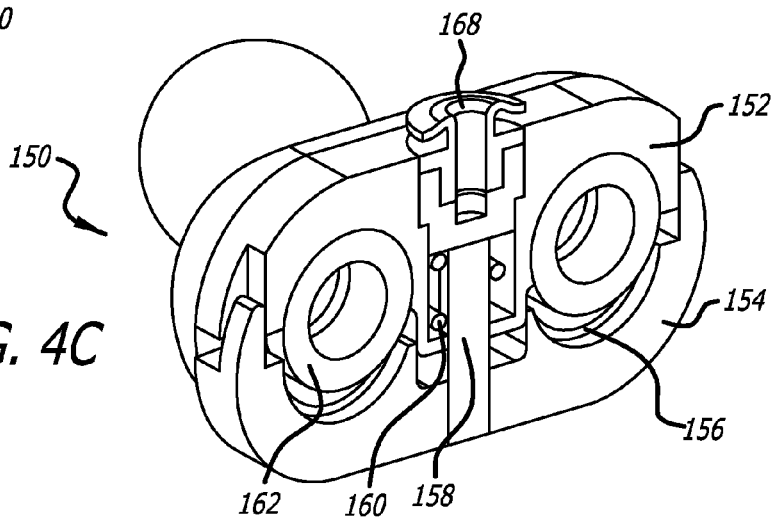
FIG. 4C is a cross-sectional view of the split collar shown in FIG. 4A in an unlocked configuration.

Another embodiment for adjusting the energy absorbing device 110 is shown in FIGS. 4A through 4C. This embodiment includes a split collar 150 having a top portion 152 and a bottom portion 154, with teeth 156 on the bottom portion (see FIG. 4C). A pin 158 is attached to the bottom portion of the collar and is biased upward with a spring 160, which forces the top and bottom portions to be in a closed position as shown in FIG. 4B. In the closed or locked position, the collar is locked onto the shafts 162 of the arbor assembly 164, which include indentations or teeth 166 to engage the teeth 156 of the bottom portion of the collar. In this embodiment, a grommet 168 is press fit into the pin, providing adjustment access via a tool, such as a 1 mm needle. As shown in FIG. 4A a sheath 170 may be disposed over the energy absorbing device, in which case the grommet is attached to the sheath so that the device can be adjusted without penetrating the sheath boundary. Other embodiments do not include a sheath.

To position the split collar 150 into an open configuration, a user inserts a tool into the grommet 168 and presses downward overcoming the biasing force of the spring 160 and moving the bottom portion 154 away from the top portion 152 as shown in FIG. 4C. Once the split collar lock is in the open or unlocked configuration, the springs 112 (not shown in FIGS. 4A-4C) may be adjusted by moving the split collar lock proximally or distally along the shafts of the arbor to increase or decrease the compression of the springs 112. Once the desired compression of the spring is achieved when the joint is at full extension, the user can remove the tool from the grommet to allow the force of spring 160 to move the split collar into the closed or locked position.

Figure 5A:
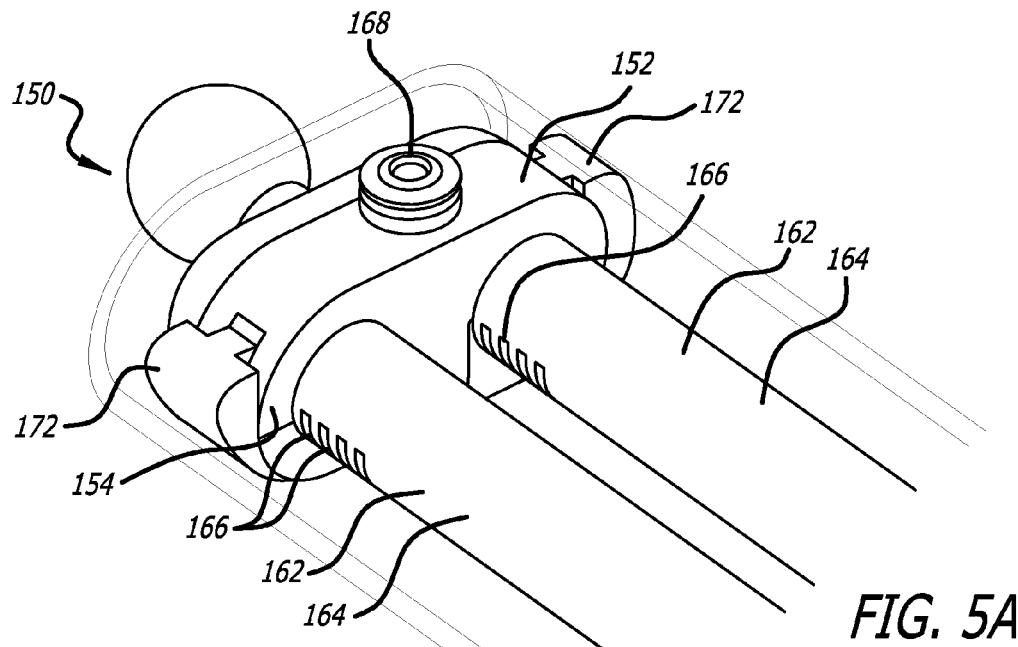
FIG. 5A is a partial perspective view, depicting one embodiment of an energy absorbing device with a split collar having compressible wings.
Figure 5B:
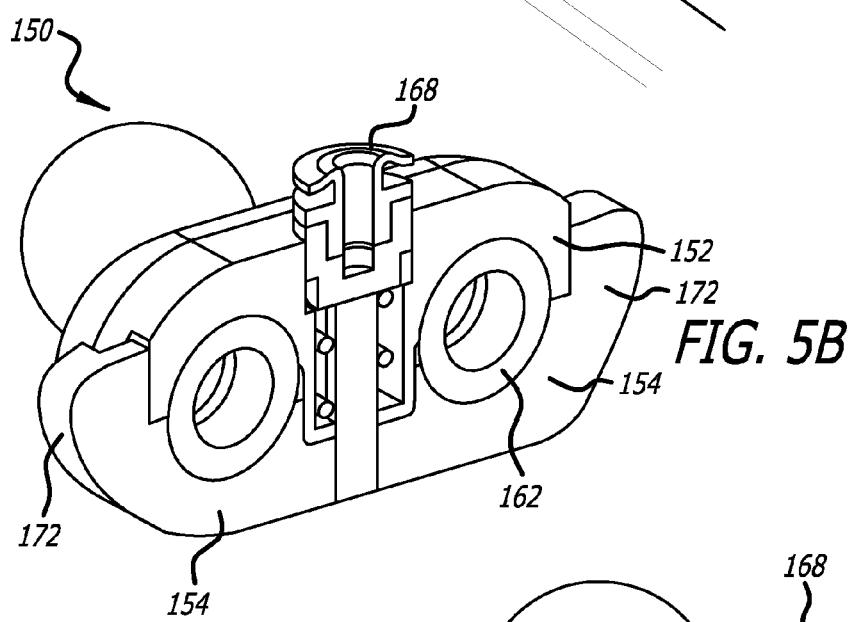
FIG. 5B is a cross-sectional view of the split collar shown in FIG. 5A in a locked configuration.
Figure 5C:
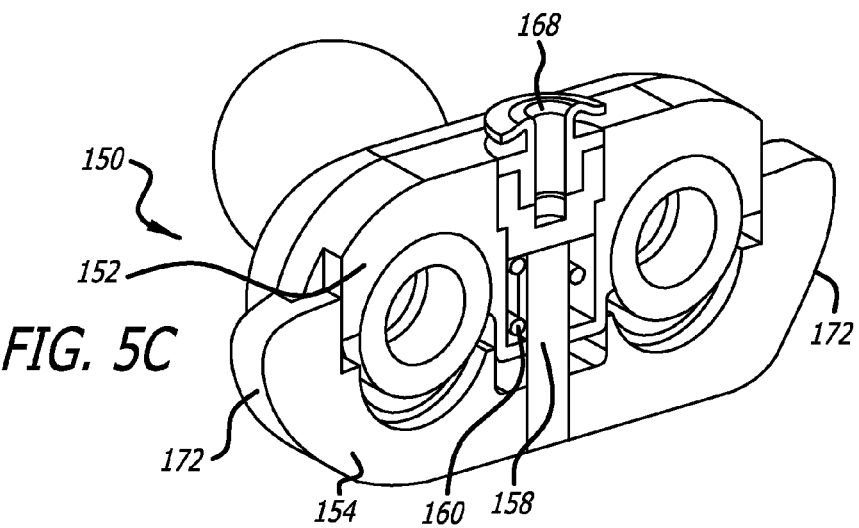
FIG. 5C is a cross-sectional view of the split collar shown in FIG. 5A in an unlocked configuration.
Figure 5D:
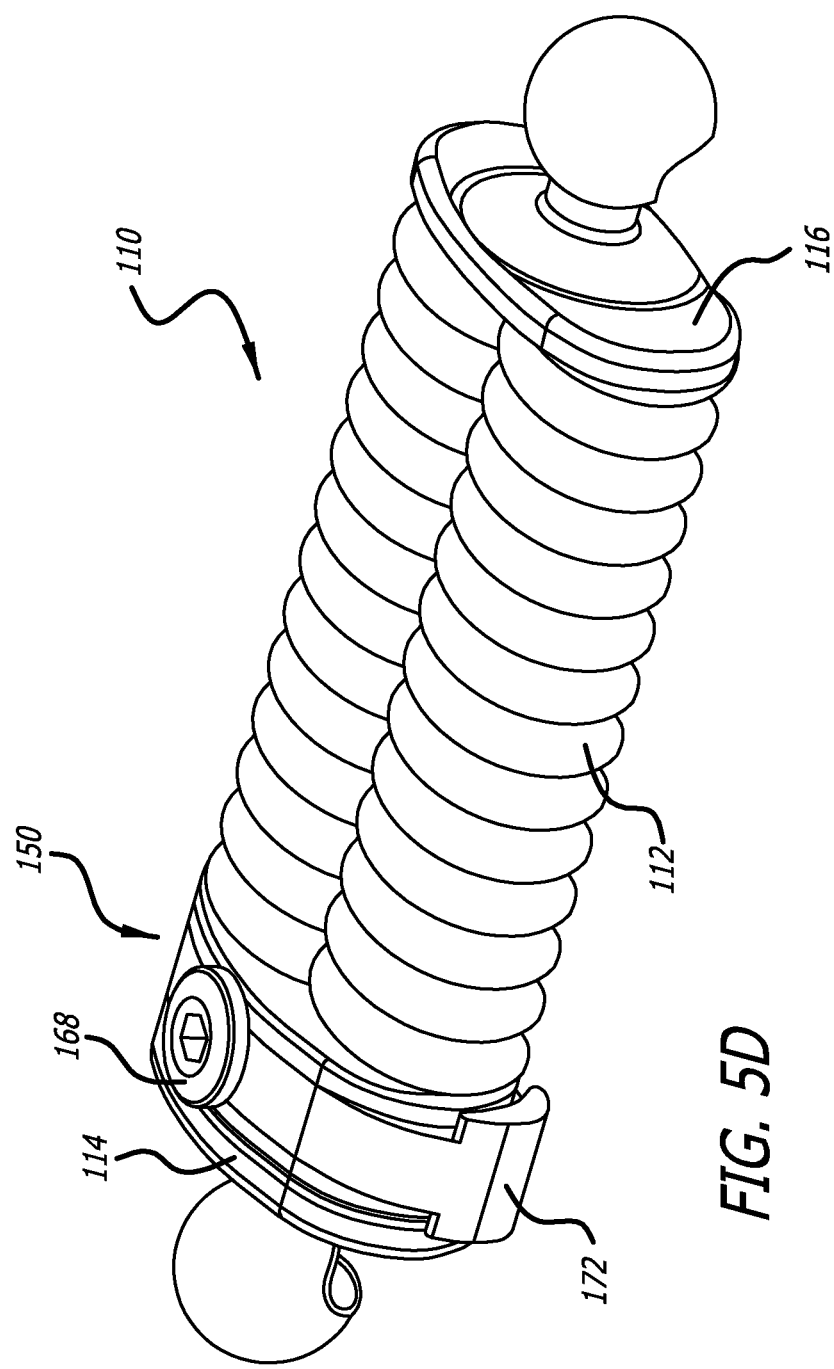
FIG. 5D is a perspective view, depicting one embodiment of an energy absorbing device with a split collar having one compressible wing.

Other embodiments are shown in FIG. 5A through 5D, and are similar to the embodiment in FIGS. 4A through 4C. Therefore, like reference numerals will be used to indicate like elements. In the embodiment shown in FIGS. 5A through 5C, the bottom portion 154 includes two wings 172 protruding from the sides of the split collar 150. The embodiment shown in FIG. 5D includes one wing 172 protruding form only one side of the device. A user can unlock the device with his fingers by pushing downward on the wings or wing to overcome the biasing force of the spring 160 and translate the collar from the closed or locked configuration, shown in FIG. 5B, into the open or unlocked configuration as shown in FIG. 5C. This allows for adjustments to be made from outside of the skin of the patient while the device is implanted. The grommet 168 may or may not be included in these embodiments to allow access with a tool to unlock the split collar lock.

In one embodiment for adjusting the energy absorbing device 110 that is attached to a knee joint, the knee starts out in an extended position. The knee is then flexed to remove any load from the springs 112. After removing the load from springs, the adjustment is made to the energy absorbing device as described above in relation to each different embodiment. Typically, the adjustment can be made over or through the skin of the patient. In one approach, the teeth on the collar locks can support up to about sixty-five pounds of pressure before yielding.

Figure 6B:
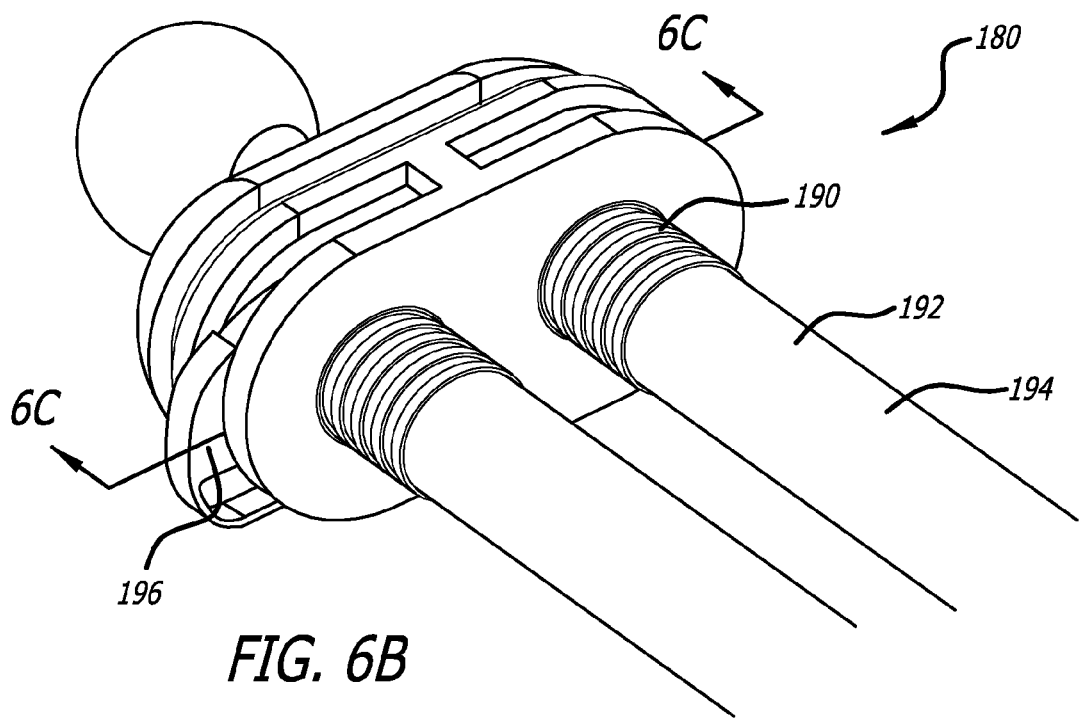
FIG. 6B is a partial perspective view of the locking collar shown in FIG. 6A in a locked configuration.
Figure 6C:
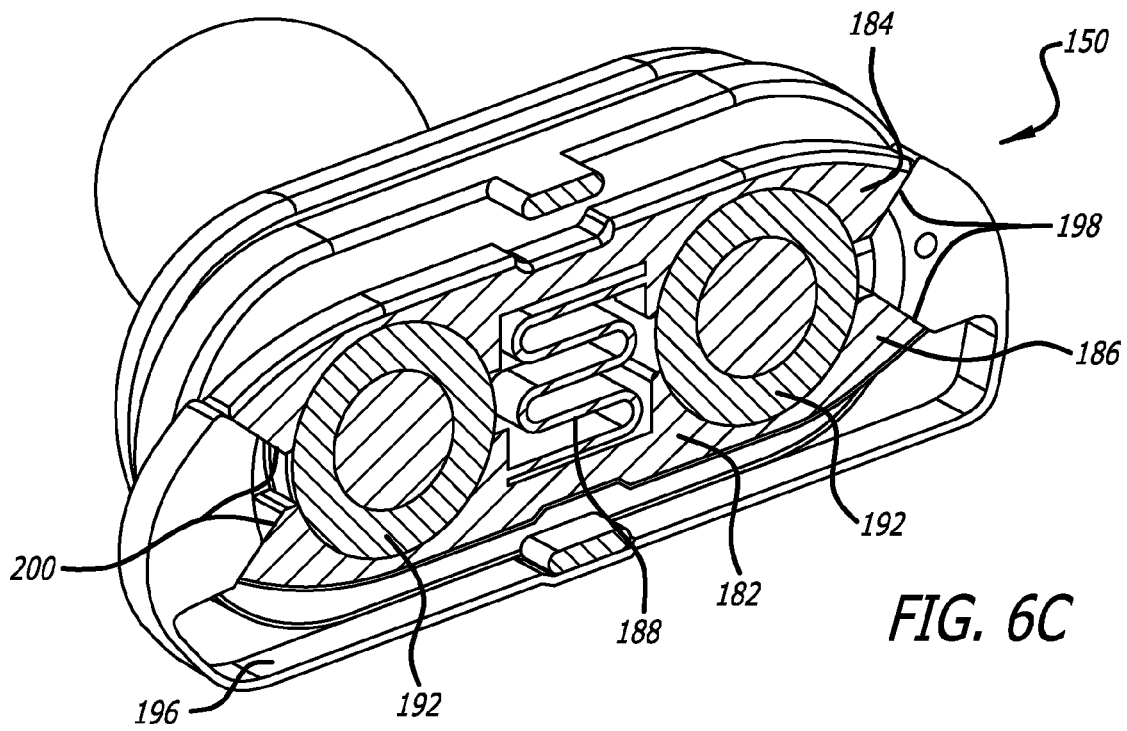
FIG. 6C is a cross-sectional view taken along line 6C-6C of FIG. 6B of the locking collar.

Another embodiment of a locking collar 180 is shown in FIGS. 6A through 6C. In this embodiment, the locking collar includes a center locking plate 182 with a top portion 184 and a bottom portion 186 connected together with an integrated spring 188. The locking plate is nominally locked in grooves 190 around the shafts 192 of the arbor 194. FIG. 6C is a cross-sectional view taken along line 6C-6C of FIG. 6B, and shows the device in the closed or locked configuration around the shafts. To unlock the top and bottom portions of the center plate, a button/spring mechanism 196 that separates the portions of the plate is pressed by a user. Tapered surfaces 198 of the button/spring mechanism engage tapered surfaces 200 of the top and bottom portion of the center locking plate to push the top and bottom portions apart from one another and overcome the biasing force of the integrated spring. This configuration disengages the teeth of the locking plate from the grooves in the shafts. Once unlocked, the collar can be moved proximally or distally to adjust the positioning of the springs 112. The adjustment of the device can be done by a user squeezing both sides of the button/spring mechanism at the same time through the skin of the patient, and then releasing the button/spring mechanism when the desired position of the spring is reached to lock the locking plate into the grooves of the shafts.

Figure 7A:
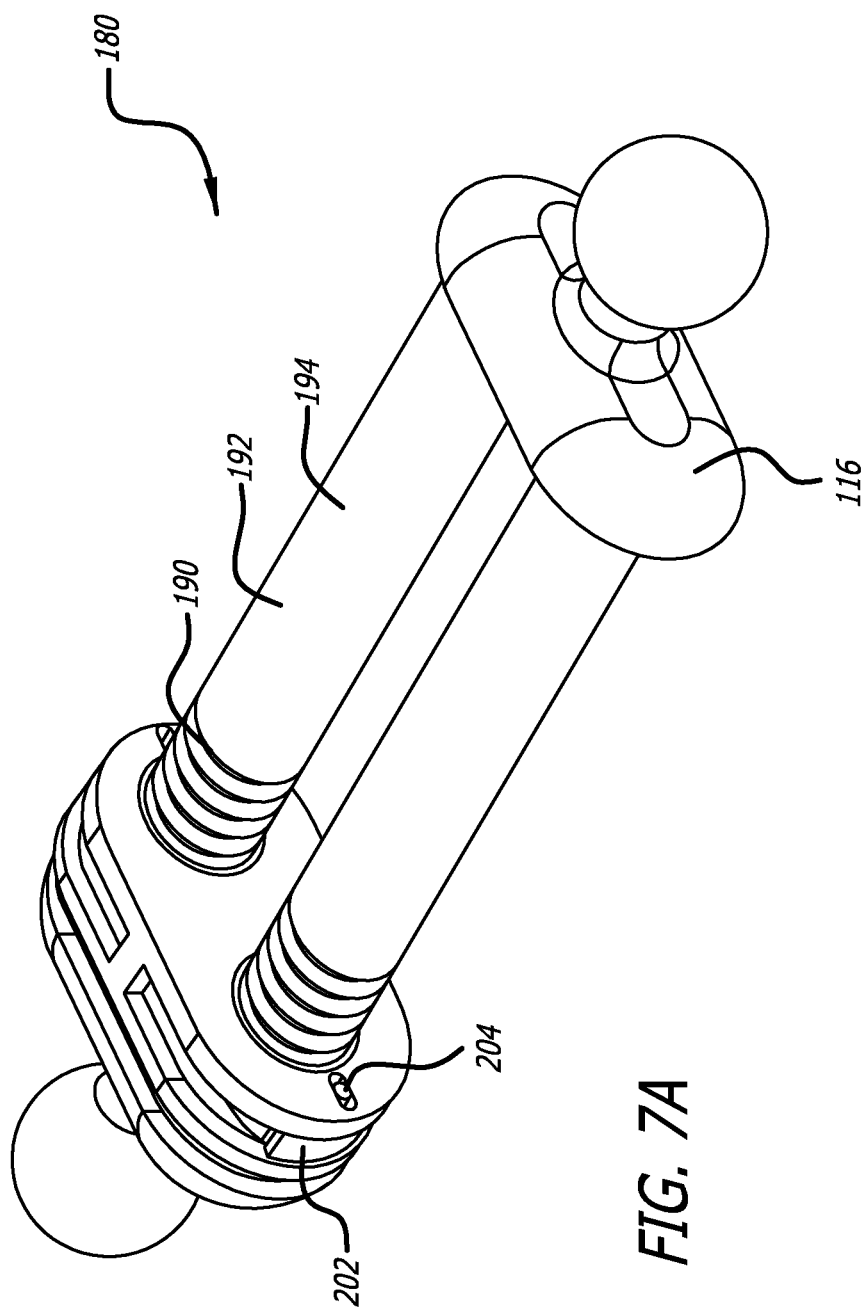
FIG. 7A is a partial perspective view, depicting another embodiment of an energy absorbing device with a locking collar.
Figure 7B:
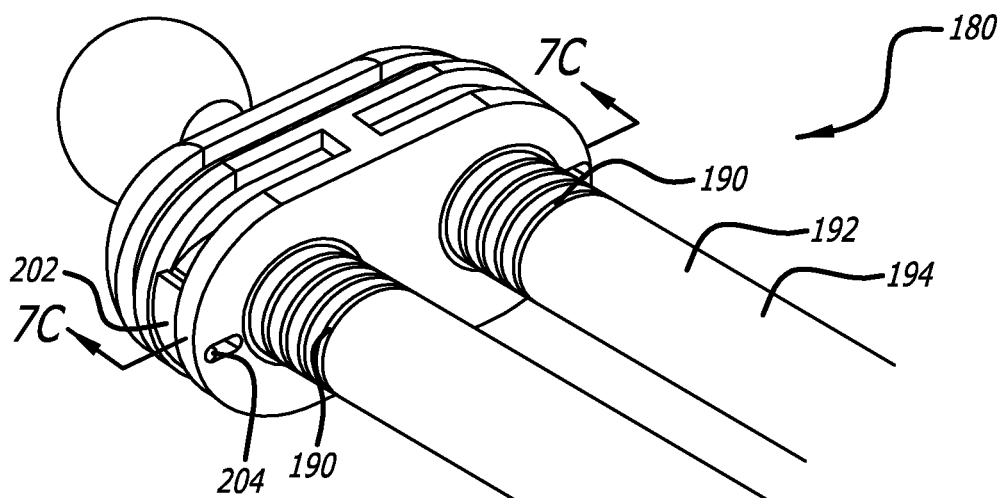
FIG. 7B is a partial perspective view of the locking collar shown in FIG. 7A.
Figure 7C:
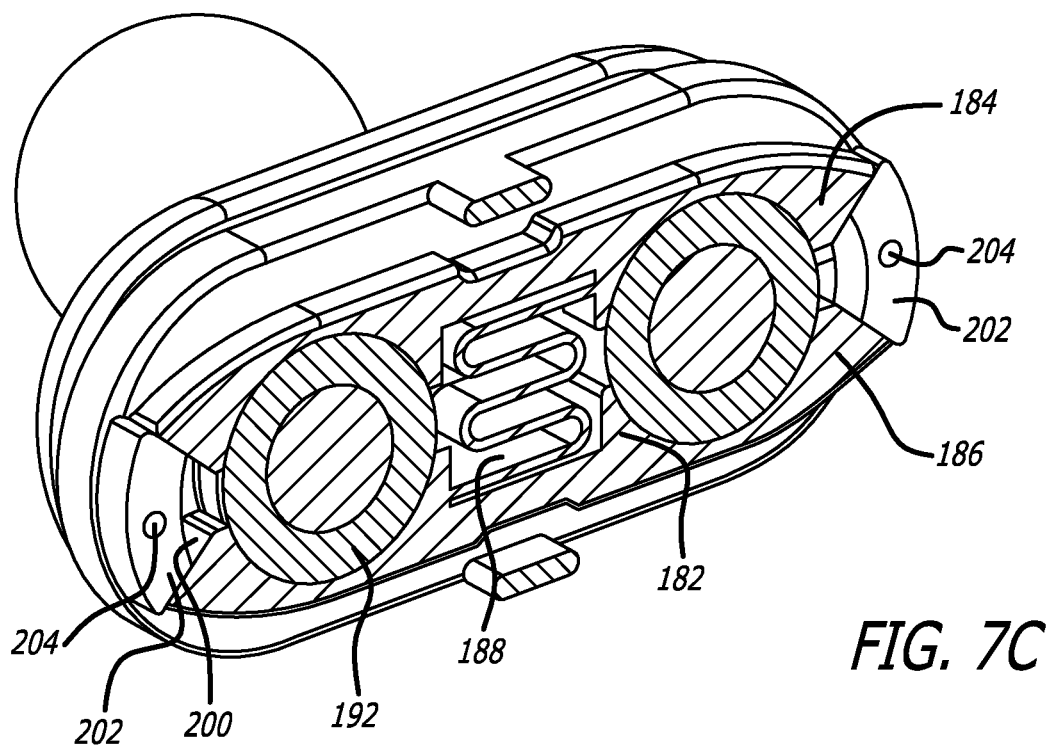
FIG. 7C is a cross-sectional view taken along line 7C-7C of FIG. 7B of the locking collar.

An embodiment similar to the embodiment shown in FIGS. 6A through 6C is shown in FIGS. 7A through 7C, and again, like reference numerals will be used to indicate like elements. In this embodiment, the button/spring mechanism 196 has been replaced with two separate buttons 202 held within the locking collar 180 by pins 204. FIG. 7C is a cross-section view taken along line 7C-7C of FIG. 7B. Operation of the locking collar in this embodiment is similar to the above embodiment in FIGS. 6A through 6C. To unlock the collar, the two buttons 202 on each side of the device are pressed inward to separate the top and bottom portions 184 and 186 of the center locking plate 182. Once the desired compression of the springs 112 is achieved, the buttons are released, thereby locking the center locking plate into the grooves 190 of the shafts 192.

Figure 8A:
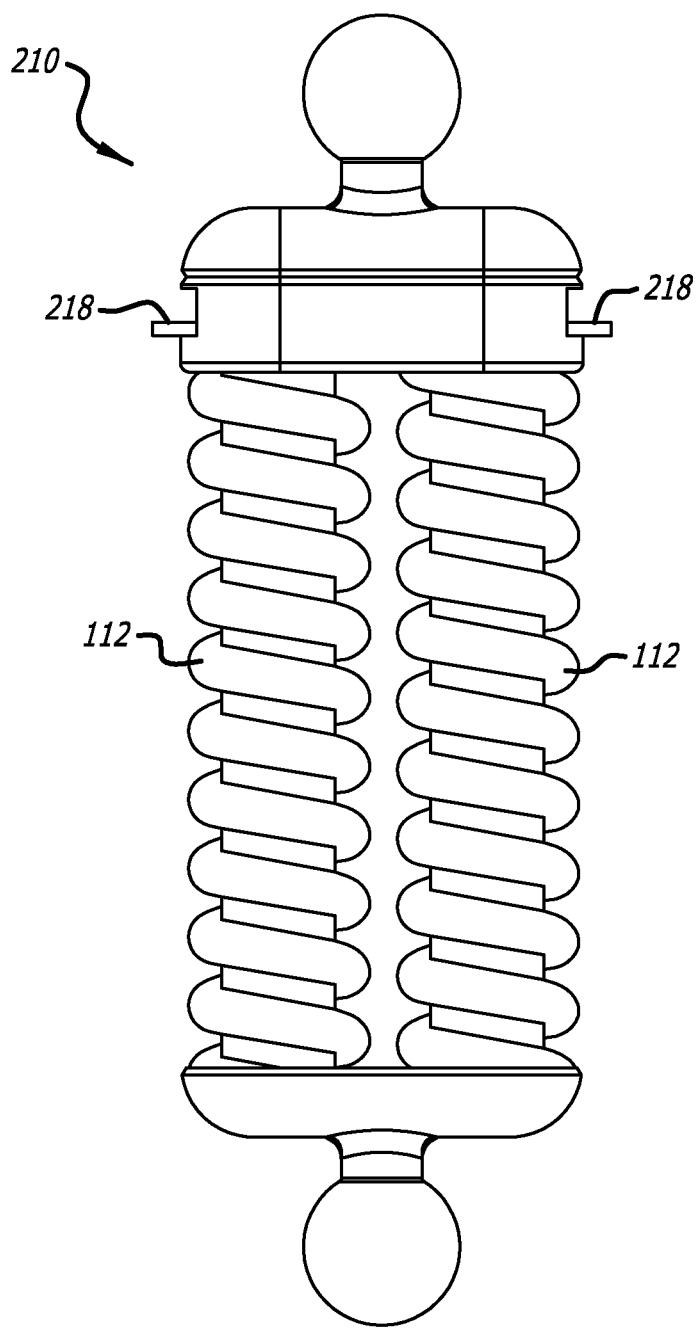
FIG. 8A is a planar view, depicting another embodiment of an energy absorbing device with a locking collar.
Figure 8B:
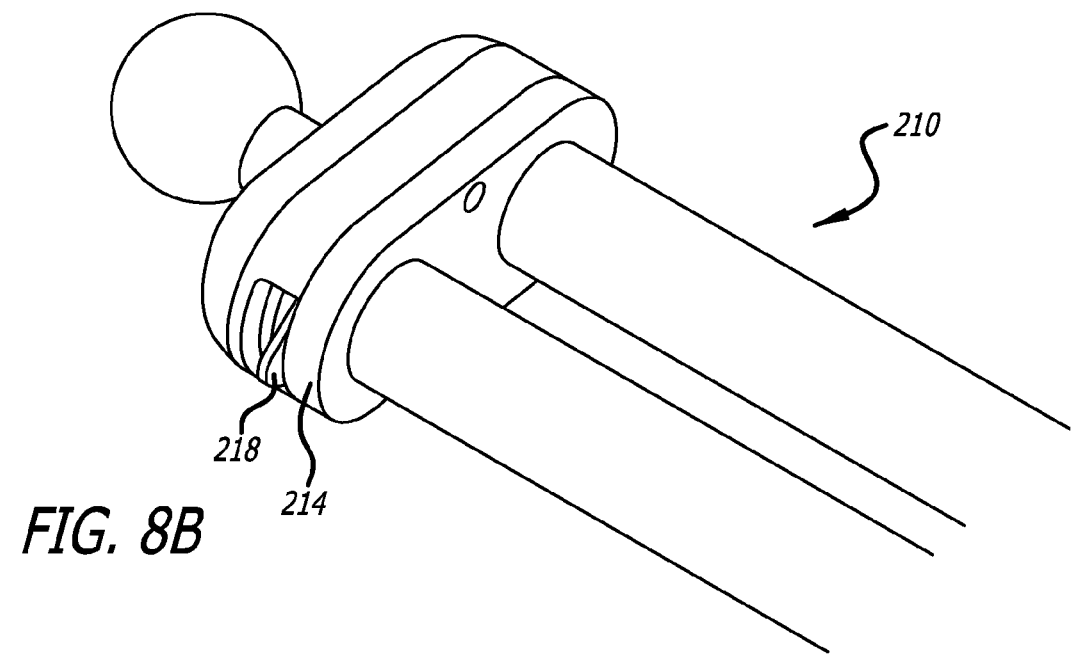
FIG. 8B is a partial perspective view of the locking collar shown in FIG. 8A.
Figure 8C:
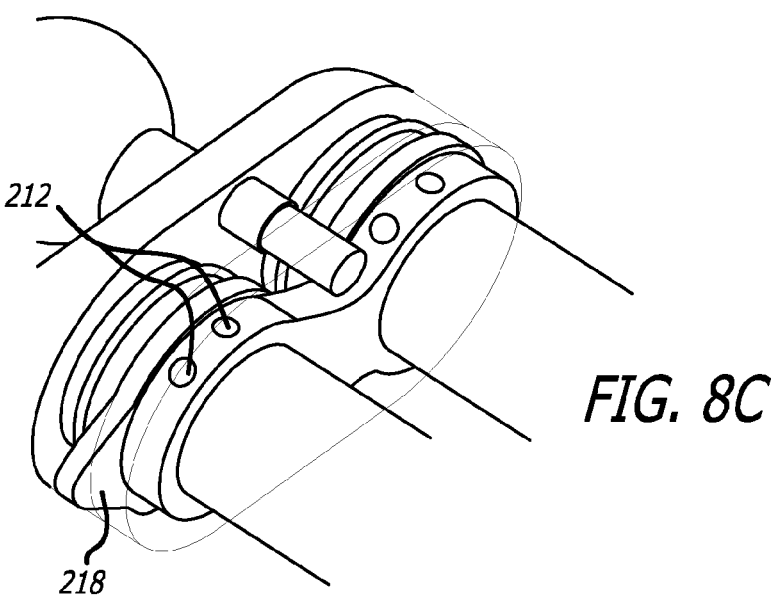
FIG. 8C is a partial perspective view showing the ball bearings of the locking collar shown in FIG. 8A.
Figure 8D:
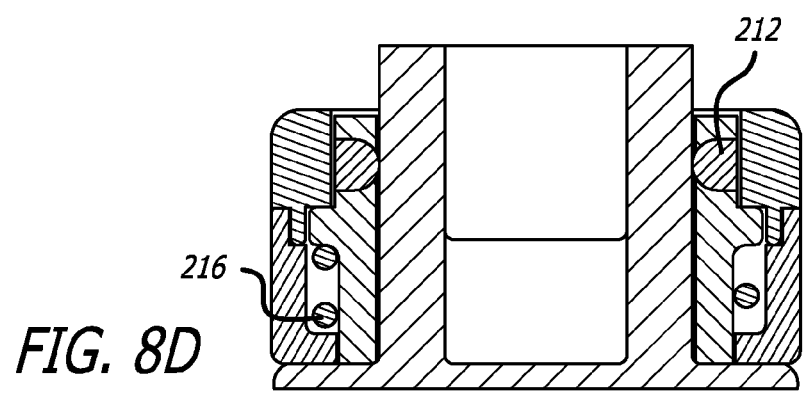
FIG. 8D is a cross-sectional view of the locking collar shown in FIG. 8B.
Figure 9A:
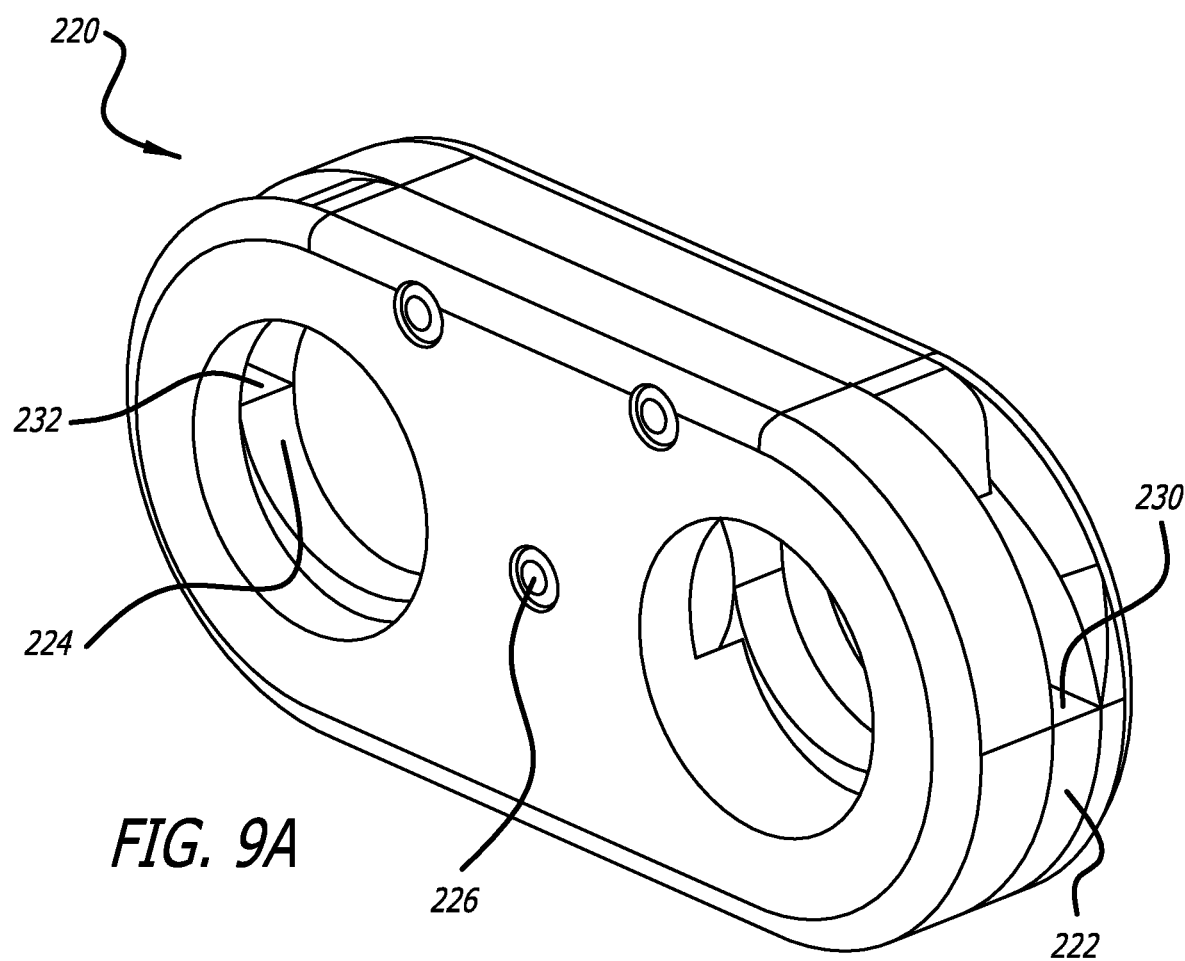
FIGS. 9A through 9D depict various views of another embodiment of a locking collar.
Figure 9B:
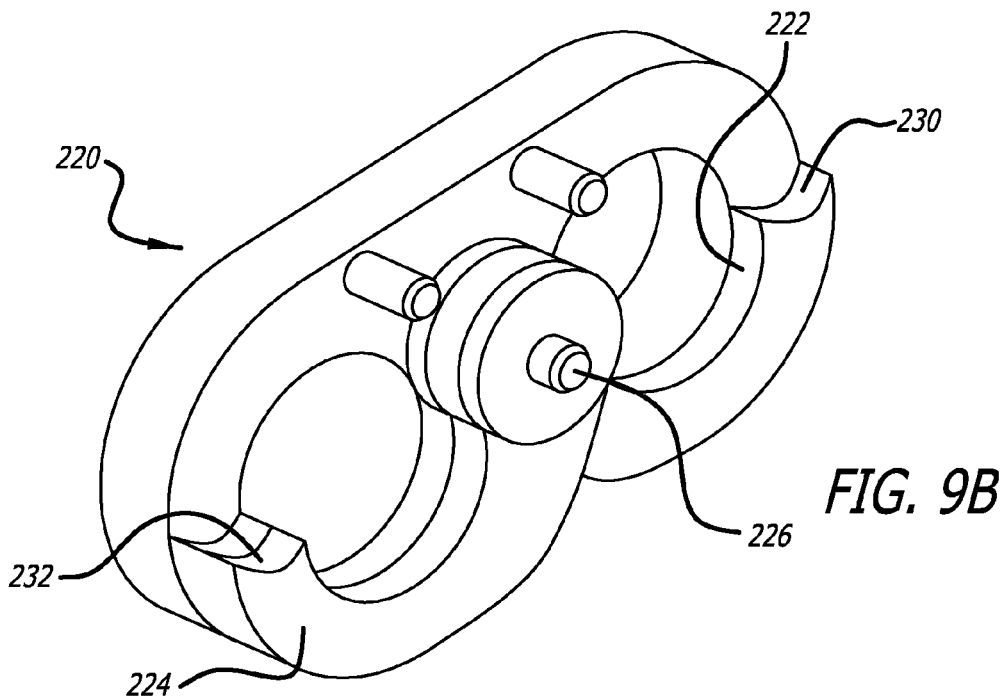
Figure 9C:
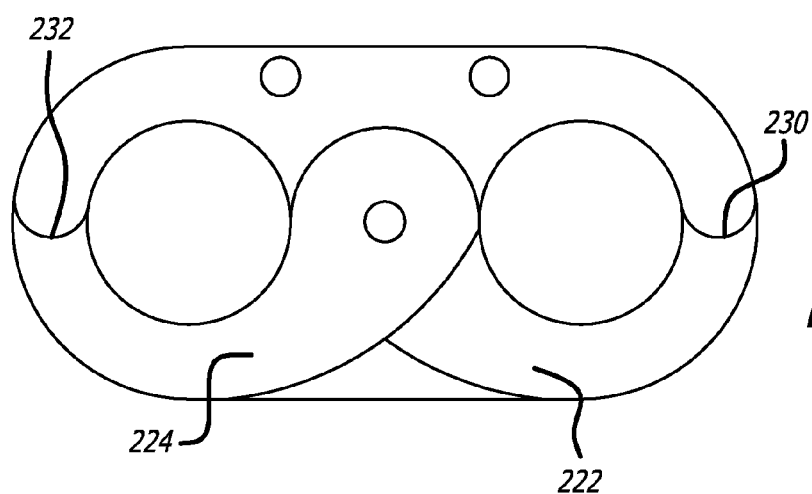
Figure 9D:
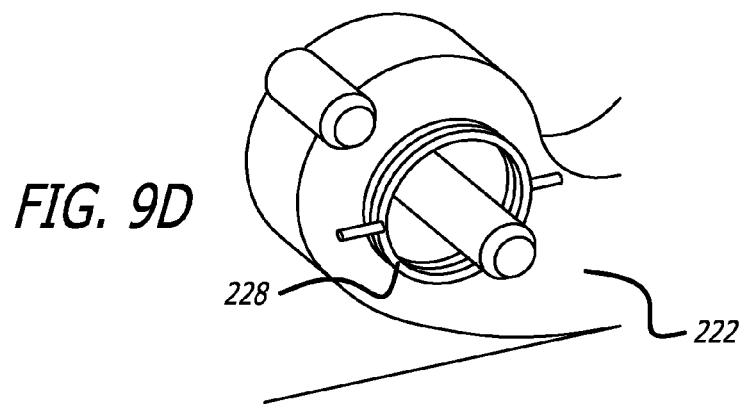

Another embodiment of a locking collar 210 is shown in FIGS. 8A through 8D. The locking collar of this embodiment is a "Grip Fast" collar, which includes a set of ball bearings 212 and a tapered locking plate 214 that locks the mechanism in place when the internal spring 216 is loaded. The locking collar is transitioned into the unlocked configuration when a user presses protruding wings 218 that remove pressure from the ball bearings, which in the locked configuration are pressed against the arbor shafts. FIG. 8D is a cross-sectional view of the "Grip Fast" collar.

FIGS. 9A through 9D show another embodiment of a locking collar 220 that includes a first locking arm 222 and a second locking arm 224 that engage with the teeth or grooves on the shafts of the arbor. The two locking arms are rotated on a pin 226 and two torsion springs 228 bias the arms in the locked position. To transition the locking collar into the unlocked configuration, a tool is used to push down on the tips 230 and 232 of the first and second locking arms, respectively, which disengages the locking arms from the grooves or teeth of the shafts and unlocks the collar. Once unlocked the collar can be moved to adjust the springs of the energy absorbing system.

Figure 10C:
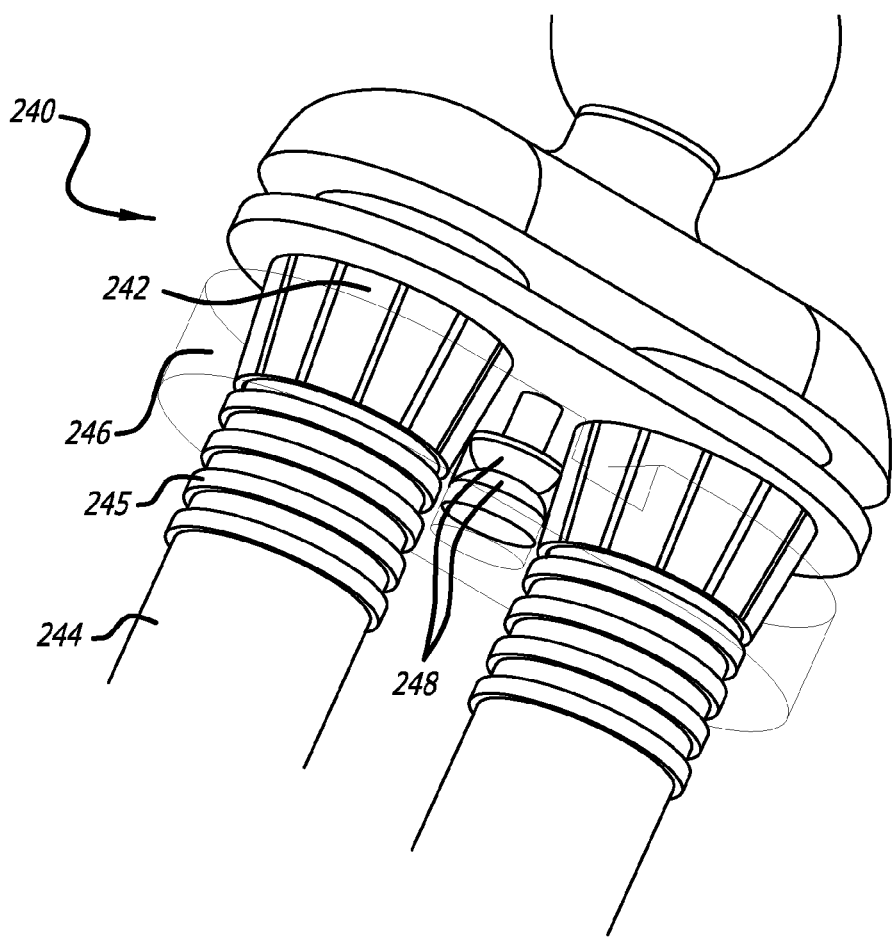
FIG. 10C is a partial perspective view showing the locking collar of FIG. 10A.
Figure 10D:
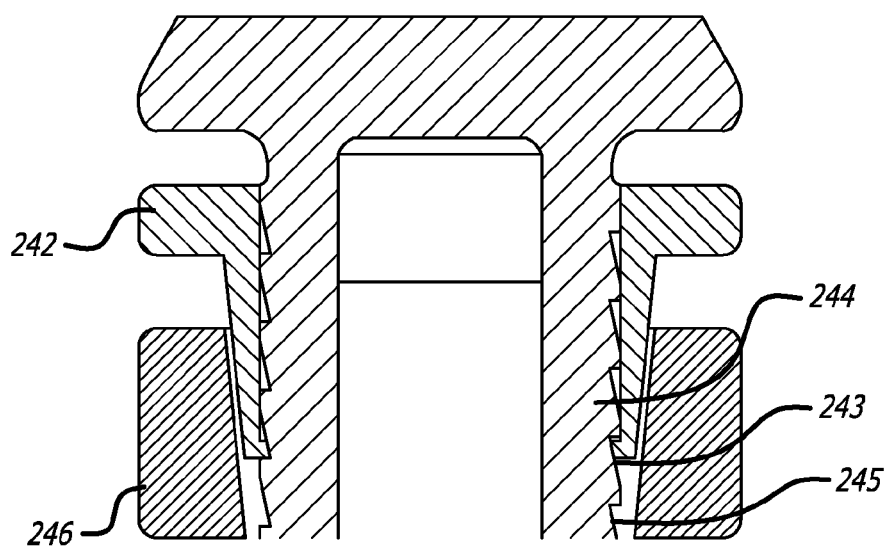
FIG. 10D is a cross-sectional view of the locking collar shown in FIG. 10A.

Another embodiment of a locking collar 240 is shown in FIGS. 10A through 10D. The collar includes a set of collets 242 with small teeth 243 which are locked into grooves 245 in shafts 244 when the spring stop 246 is forced against the set of collets. The collets and the spring stop are nominally biased against each other by two small inverted disc springs 248 in the locked configuration shown in FIG. 10A. To unlock the collar, a tool 249, such as a 2×1 mm tool, is used to disengage the collar from the shafts by inserting the tool and rotating it, thereby separating the collets and spring stop. This unlocked configuration is shown in FIGS. 10B through 10D. To return the collar to the locked configuration, the tool is rotated in an opposite direction and removed to re-engage the teeth 245 of the collets 244 with the grooves 245 of the shafts 244.

Figure 11A:
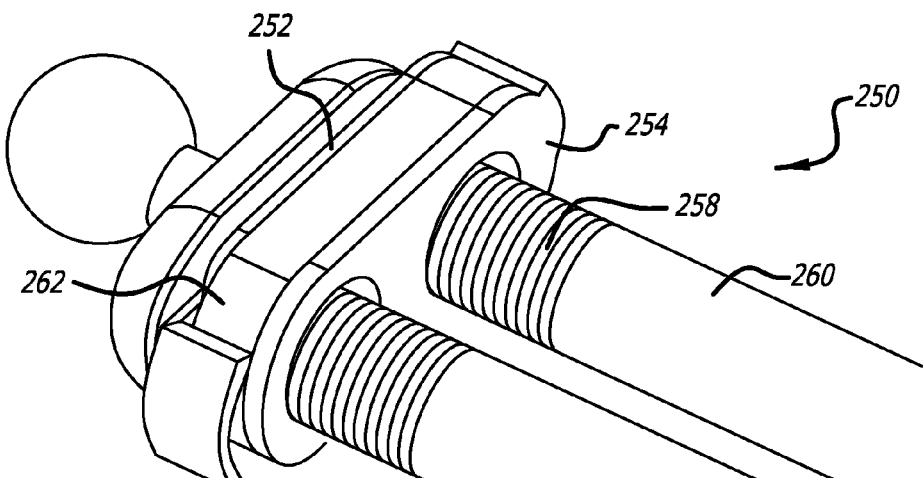
FIGS. 11A through 11C show various views of another embodiment of a locking collar.
Figure 11B:
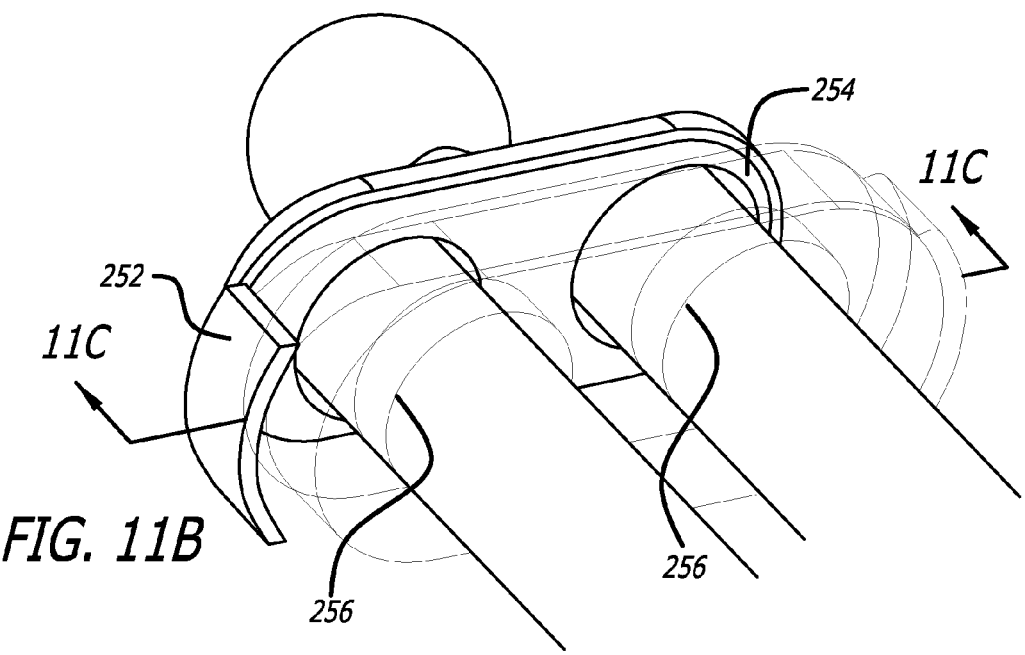
Figure 11C:
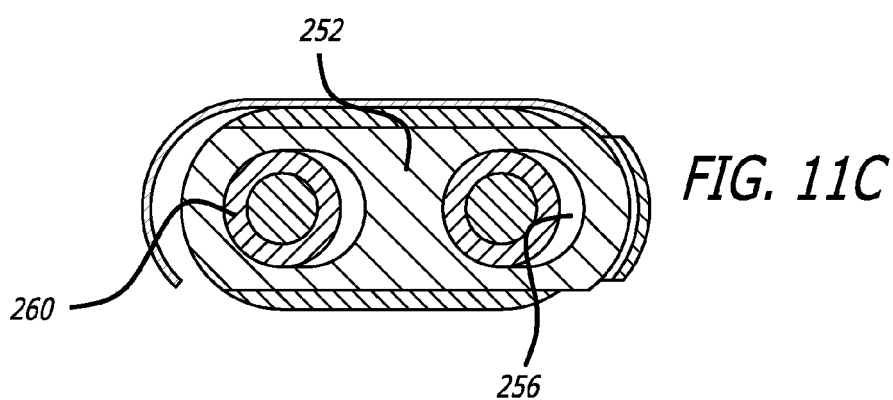

Yet another embodiment of a stop collar 250 is shown in FIGS. 11A through 11C. The stop collar includes a first spring stop slider 252 and a second spring stop slider 254, each having two cutouts 256 that engage teeth or grooves 258 in shafts 260. The cutouts 256 of the first and second spring stops disengage the grooves on the shafts when slid perpendicular to the shafts. The first and second sliders are separated by a single spring 262 and biased nominally in the locked position. The mechanism is disengaged once the first and second sliders are squeezed together to disengage the cutouts of the spring stop sliders from the shafts. FIG. 11B shows the second spring stop slider in phantom so the cutouts of the first spring stop can be seen. Also, FIG. 11C shows the cross-section taken at line 11C-11C of FIG. 11B, with the mechanism in the locked configuration and the first spring stop engaging the grooves of the shafts.

Figure 12B:
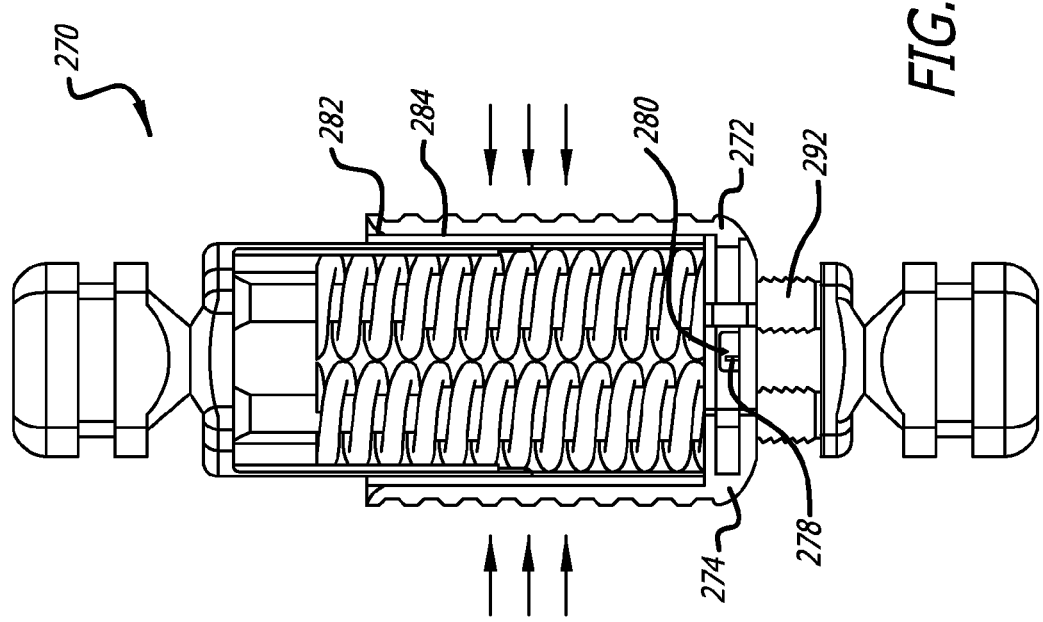
FIGS. 12A through 12H show one embodiment of an energy absorbing device and a method for adjusting the load of the device.
Figure 12A:
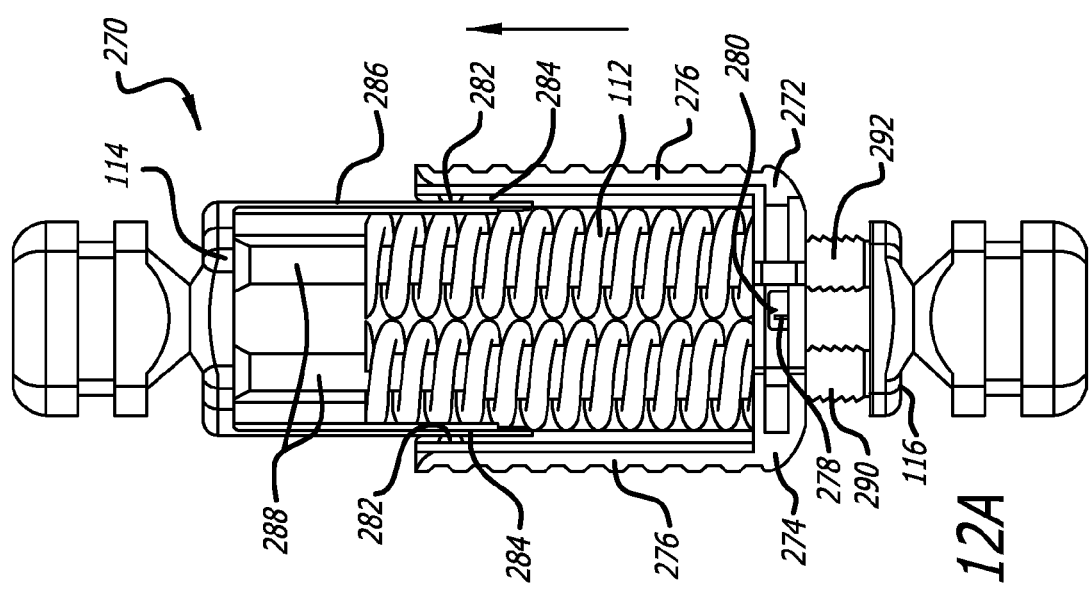

FIGS. 12A through 12H show another embodiment of an energy absorbing device with a stop collar 270, and a method of adjusting the device. FIG. 12A shows the stop collar having an adjustment core 272 and an adjustment block 274 that are slidingly engaged together. The adjustment core and adjustment block each include a grip arm 276 that can be manipulated or squeezed by a user. There is also a spring finger 278 disposed on the adjustment block, and a tooth 280 disposed on the adjustable core near the spring finger, so that when the adjustment core and adjustment block are squeezed together or released, the spring finger is deflected by the tooth 280 and creates an audible sound letting the user know when the stop collar is unlocked and locked. Each grip arm 276 includes a tooth 282 that comes in contact and rests within a slot 284 disposed on a wall 286 of the piston base 114. The piston base also includes pistons 288 that slide within shafts 290 of the arbor base 116. To adjust the energy absorbing device by increasing or decreasing the compression of spring 112, the patient's leg is flexed to about a 90° angle, and the energy absorbing device 110 will be in a similar configuration to that shown in FIG. 12A. In this position there is no load on the springs 112 and the stop collar 270 is locked into position on the teeth or grooves 292 of the shaft.

Figure 12C:
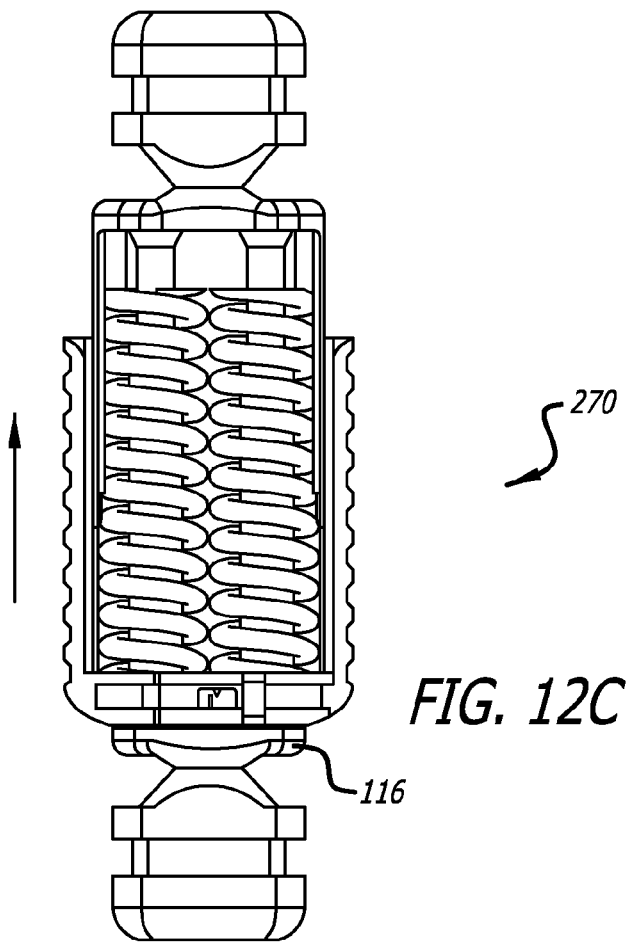

Next, as shown in FIG. 12B, the stop collar 270 is forced into the unlocked configuration by squeezing the grip arms 276 of the adjustment core 272 and the adjustment block 274 towards one another. An audible sound will result when the spring finger 278 deflects off of the tooth 280. The leg is then extended and the stop collar stops on the arbor base 116 at a zero load position as shown in FIG. 12C.

Figure 12D:
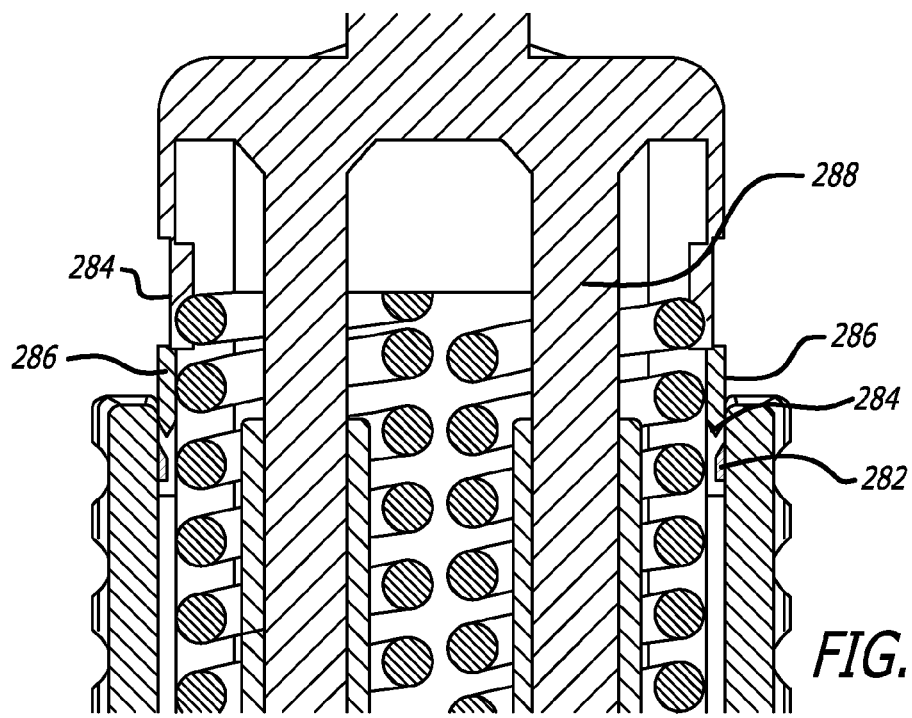
Figure 12E:
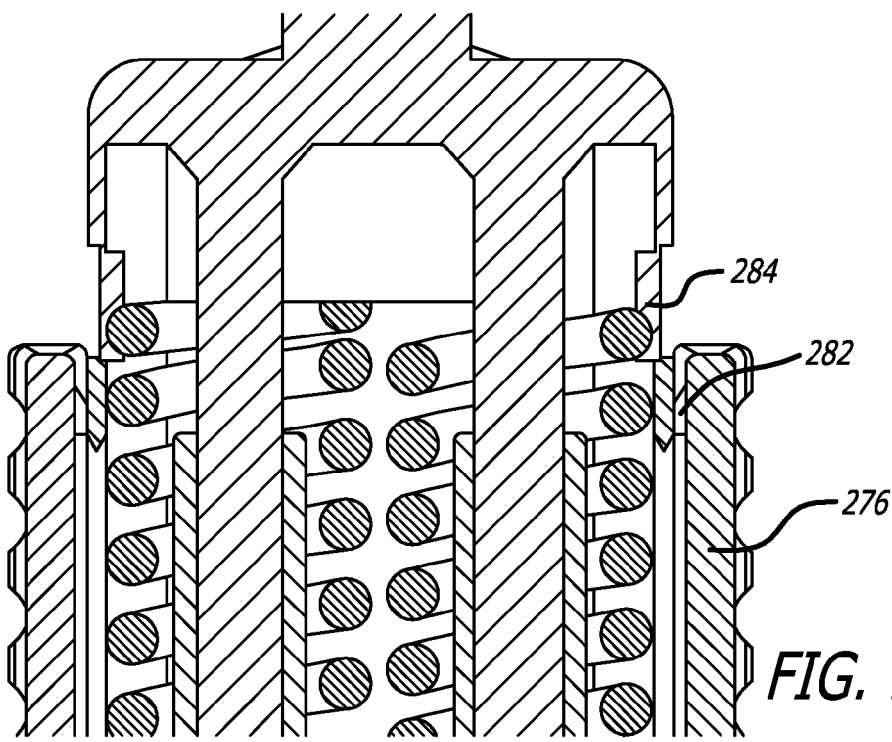

FIG. 12D shows the teeth 282 of the grip arms 276 hitting the piston walls 286. As the leg is extended, the grip arms open slightly for the teeth 282 to ride over the piston walls as shown in FIG. 12E. Finally, at complete extension, the teeth 282 fall into slots 284 of the piston walls, linking the piston walls with the arms of the stop collar, as shown in FIG. 12F.

Figure 12F:
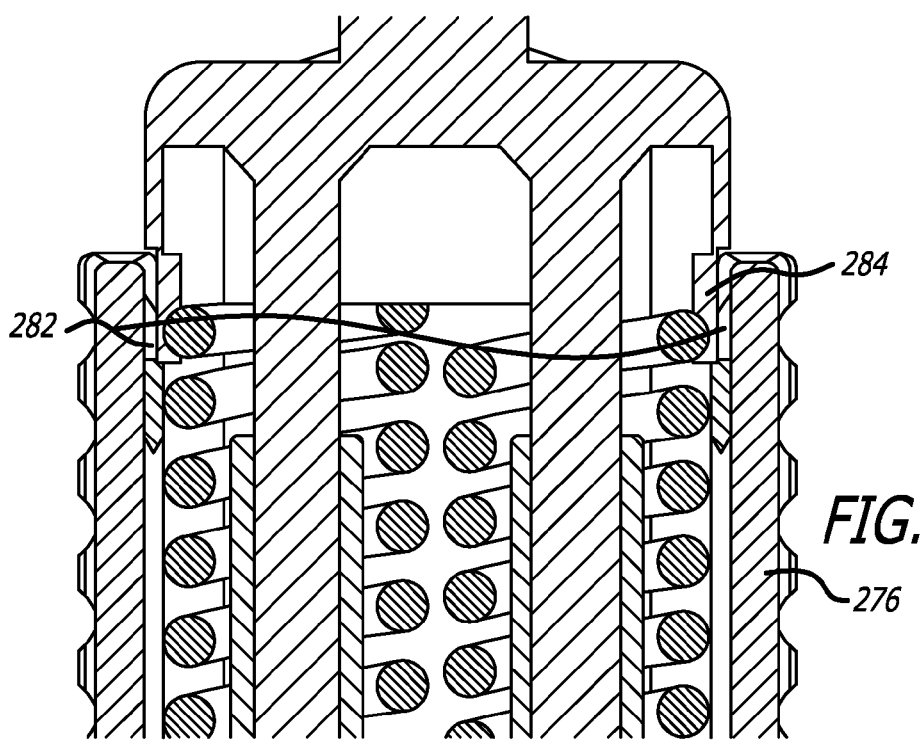
Figure 12H:
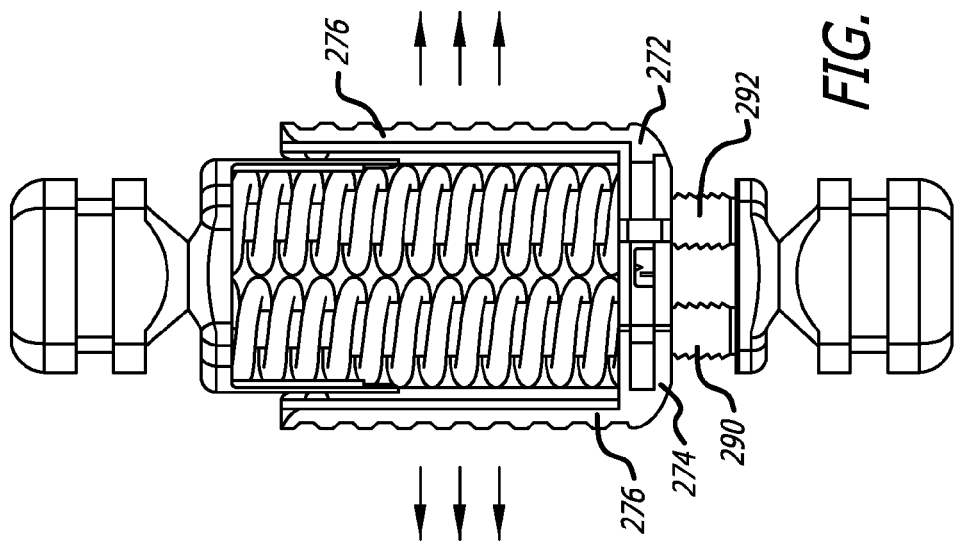
Figure 12G:
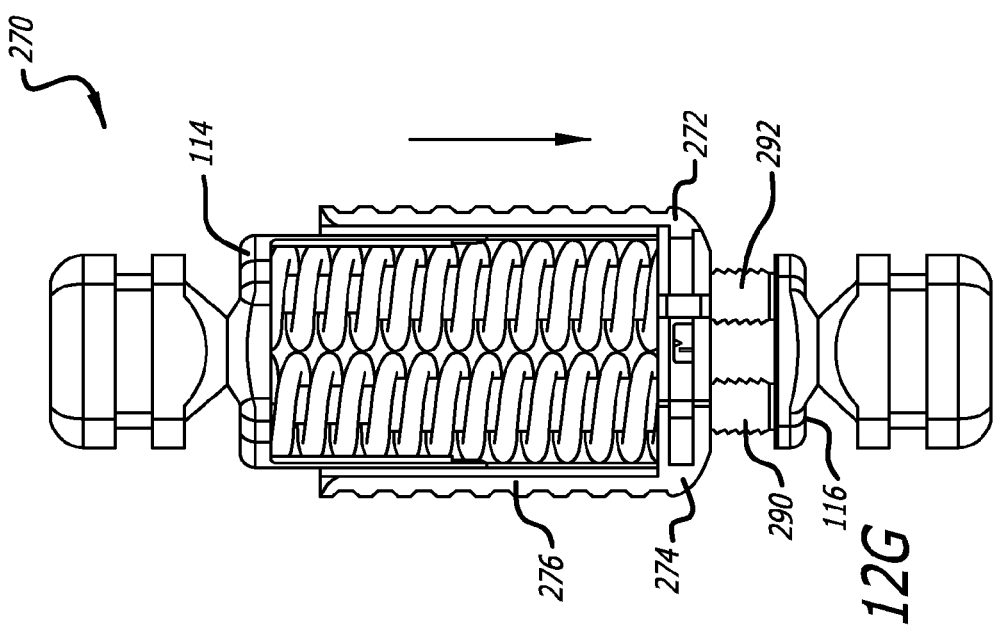

With the stop collar 270 still in the unlocked configuration, the leg is now flexed to a desired angle, and the shafts 290 extend away from the stop collar as shown in FIG. 12G. Once the desired angle and the desired compression of the springs 112 are reached, the arms 276 of the stop collar are released and the leg is extended to engage the stop collar and lock into the new position in the grooves 292 of the shafts 290 as shown in FIG. 12H. When the stop collar is released, another audible sound will be created by the spring finger 278. In one embodiment there is also another spring finger located on the adjustment core that comes into contact with teeth on the arbor shaft to provide an audible sound when the stop collar is being translated over the arbor shaft. These audible sounds provide feedback to the user who may be adjusting the load of the device over the skin of the patient.

Figure 13:
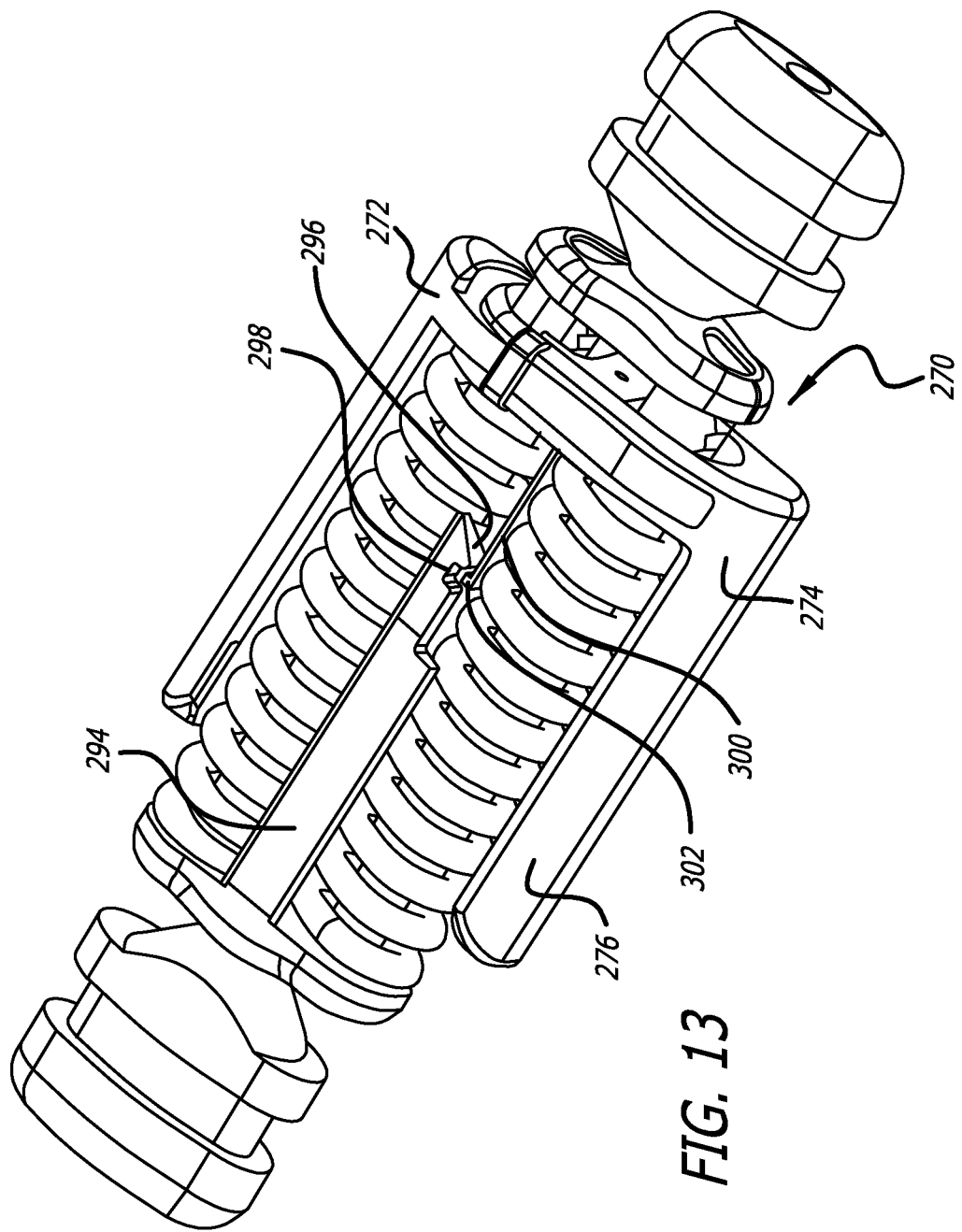
FIG. 13 is a perspective view, depicting another embodiment of an energy absorbing device.

An embodiment of the energy absorbing device 110 shown in FIG. 13 is similar to the device depicted in FIGS. 12A through 12H. In this embodiment however, there are no piston walls, but there is a post 294 on the piston base 116, and the post includes a tapered end 296 and a notch 298 near the tapered end. There is also a snap clip 300 extending away from the stop collar 270 with a hook 302 at its end. Instead of teeth 282 on the grip arms 276 engaging slots 284 on the piston wall as shown in FIG. 12F of the above embodiment, in this embodiment, the hook of the snap clip engages the notch of the piston post to connect the piston base with the stop collar.

Figure 14:
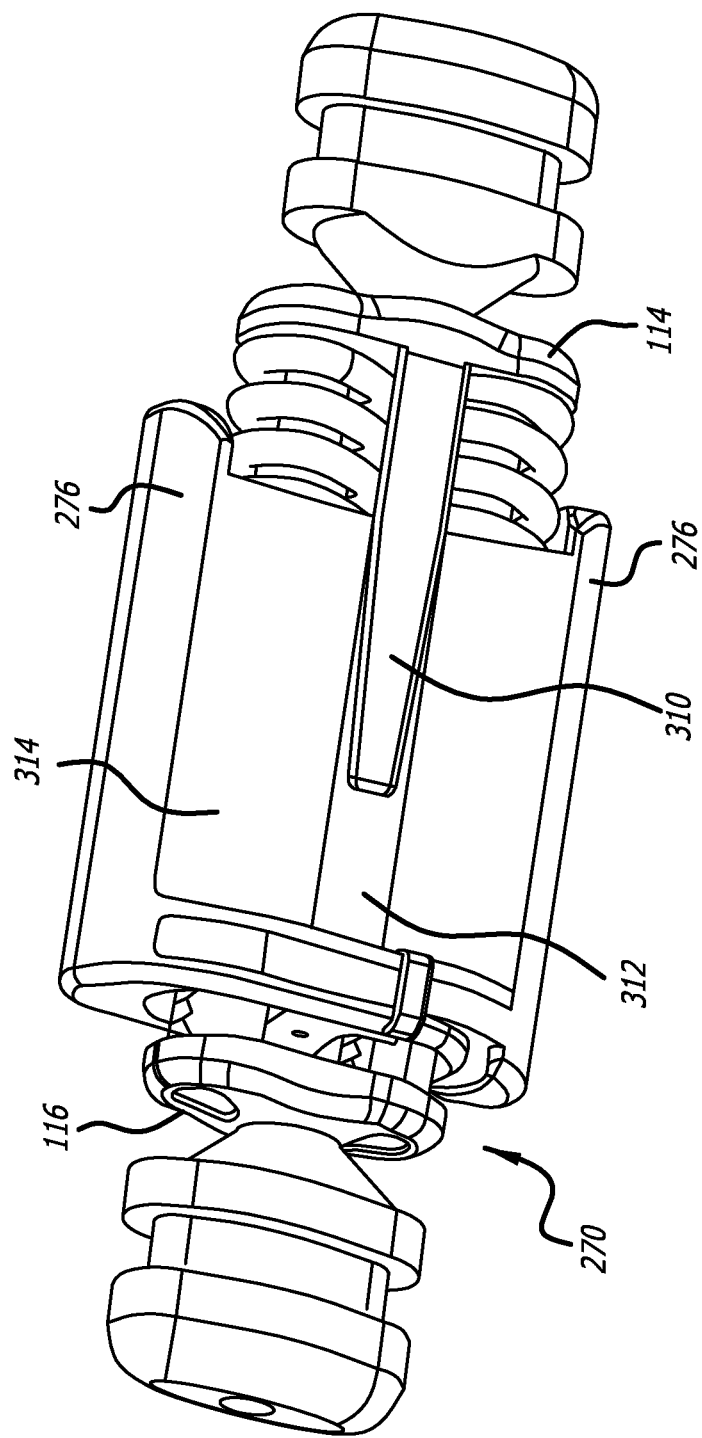
FIG. 14 is a perspective view, depicting yet another embodiment of an energy absorbing device.

FIG. 14 depicts another embodiment that is similar to last two embodiments, except in this embodiment, the piston base 114 includes a tapered post 310 that slides over a recess 312 in a spring tube 314. The spring tube covers the springs 112 of the energy absorbing device 110 and is in contact with the stop collar 270.

Figure 15:
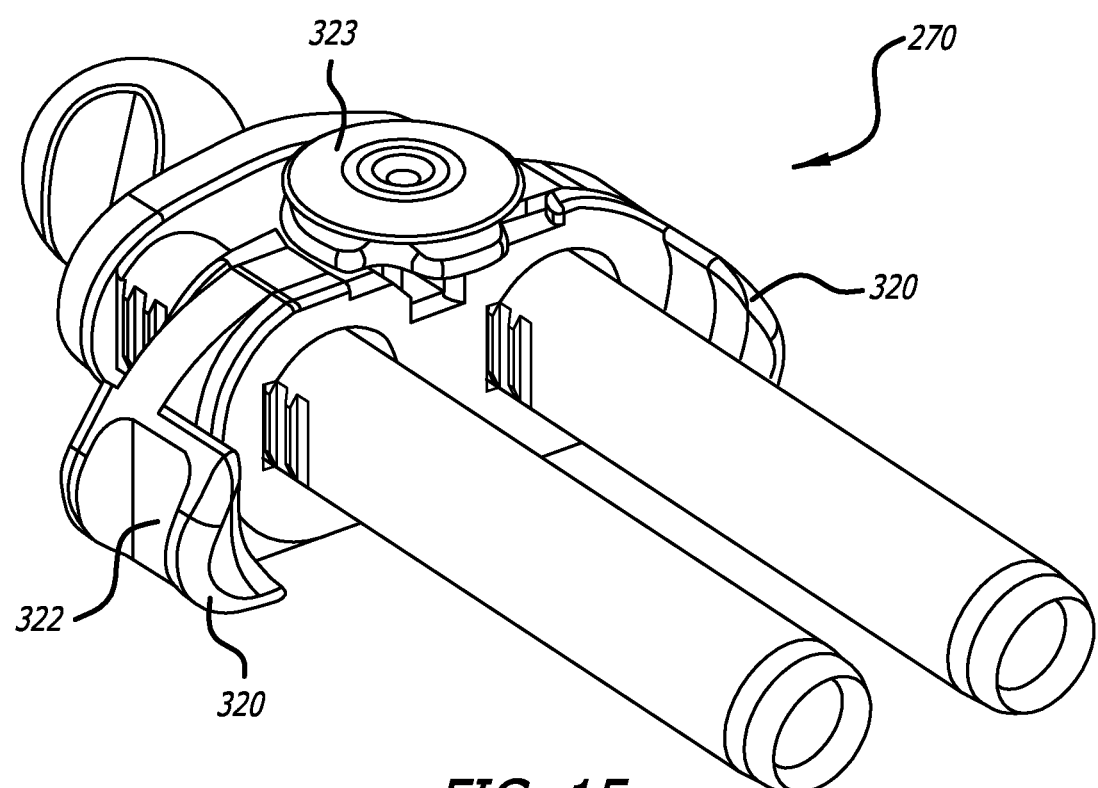
FIG. 15 is a perspective view, depicting another embodiment of an energy absorbing device.

FIG. 15 shows another similar embodiment, of the collar stop 270. In this embodiment, the long grip arms have been replaced with short arms 320 with recesses 322 configured for receiving the ends of pliers or another tool that can be used to grip and squeeze the short arms to unlock the stop collar 270. As shown in FIG. 15, this embodiment may also include a sheath eyelet 323 for attachment to a sheath that covers the energy absorbing device.

Figure 16:
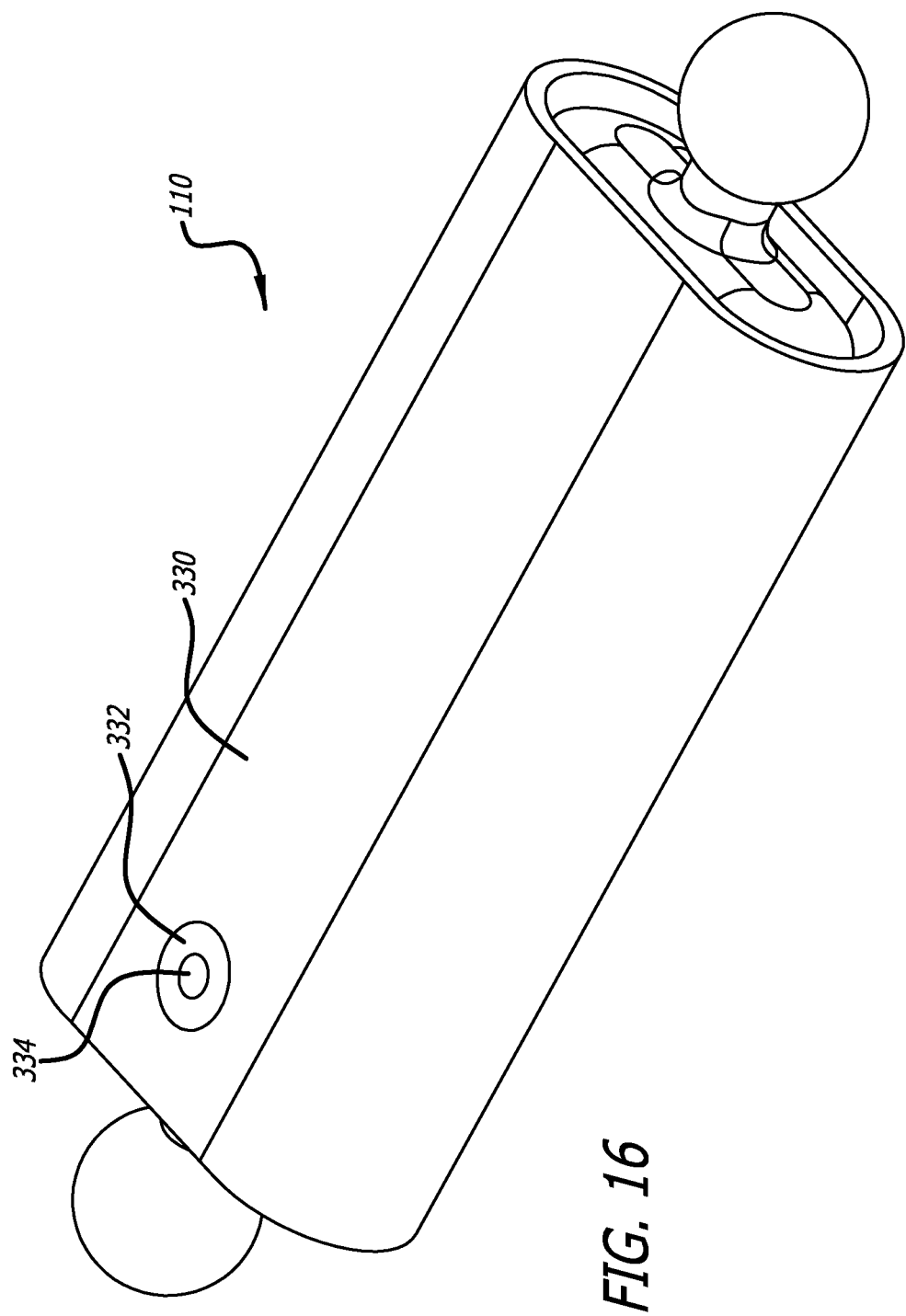
FIG. 16 is a perspective view, depicting a sheath placed over an energy absorbing device.

Any of the dual spring embodiments discussed above can be covered by a sheath 330 as shown in FIG. 16. A sheath eyelet 332 may be attached to the collar stop of the energy absorbing device 110. There may also be a hole 334 to gain access to a grommet associated with the stop collar to lock or unlock the device in order to adjust the device.

Figure 17A:
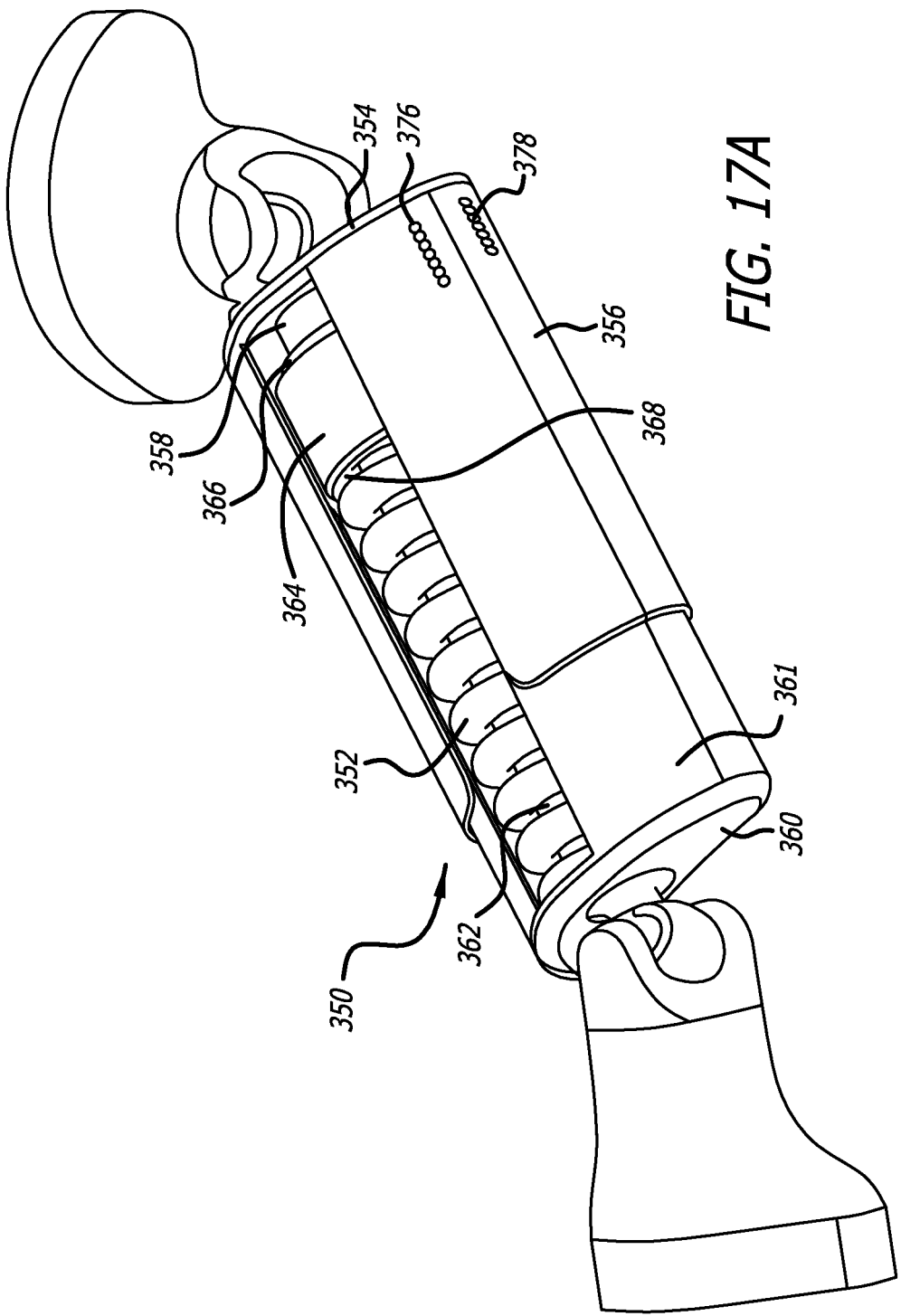
FIG. 17A is a perspective view, depicting an embodiment of a single spring energy absorbing device.
Figure 17B:
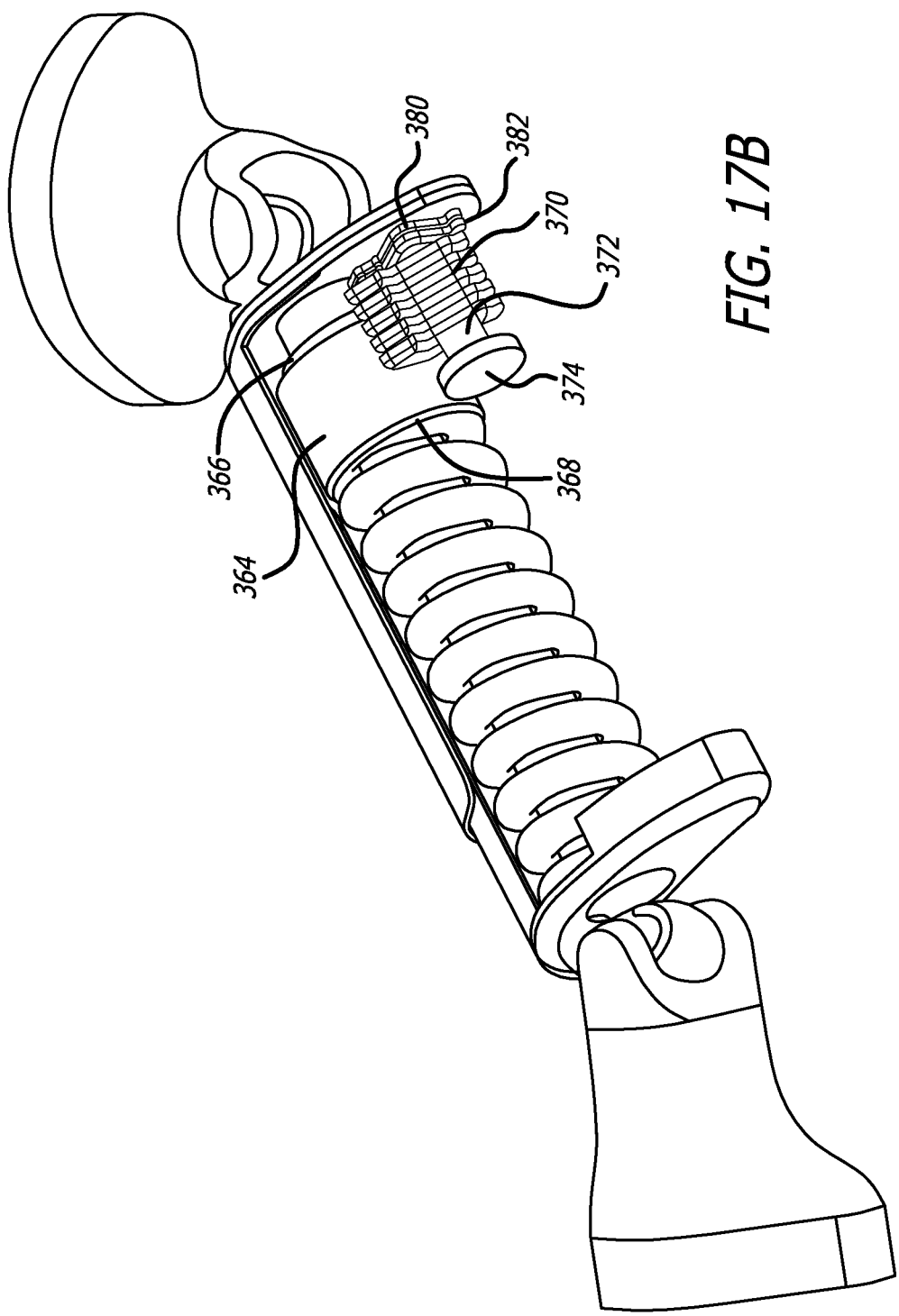
FIG. 17B is a partial perspective view of the energy absorbing device shown in FIG. 17A.

Referring now to FIGS. 17A and 17B, another embodiment of an energy absorbing device 350 is shown to include a single spring 352 to absorb energy. The device includes an arbor base 354 with an arbor casing 356 and a shaft 358. Also included is a piston base 360 with a piston casing 361 and a piston 362 that slides within the shaft of the arbor base. The piston casing is configured to slide under the arbor casing. Surrounding the arbor shaft is a spring stop 364 with a proximal or first end 366 and a distal or second end 368. There are also a plurality of shims 370 that are disposed on a post 372 connected to the arbor base. The post is disposed adjacent to the spring stop. A shim stop 374 is positioned at the end of the post to keep the shims on the post and still allowing the shims to rotate about the post. In this embodiment there are seven shims, that are each about 1 mm in width, however, any number of shims can be used and they may be any width. As shown in FIG. 17A, there are a plurality of top holes 376 in the arbor casing and a plurality of bottom holes 378 in the arbor casing.

To adjust the load manipulation profile of the energy absorbing device 350, a tool, such as a needle or other instrument, is inserted into the most proximal top hole 376 to activate the most proximal shim 370. An end of the instrument inserted through the top holes will push against a first edge 380 of the shim and rotate the shim on the post 372 so that the shim slides inbetween the proximal end 366 of the spring stop 364 and the base of the arbor base 354. This pushes the spring stop distally and thereby compresses the spring 352 that is abutted against the distal end 368 of the spring stop. FIG. 17B shows two shims activated. Any number of the shims can be activated by inserting an instrument into consecutive top holes starting from the proximal end. To deactivate any number of the shims, the instrument is inserted into the bottom holes 378 disposed on the arbor casing. The end of the instrument inserted through the bottom holes will come into contact with a second edge 382 of the shim and rotate the shim in an opposite direction to remove the shim from between the spring stop and the arbor base. Any number of shims can be deactivated starting at the distal most activated shim. Activating and deactivating shims allow a user to adjust the compression of the position of the spring stop and the spring. Such adjustments can be made when the device 350 is unloaded such as during flexion.

Figure 18B:
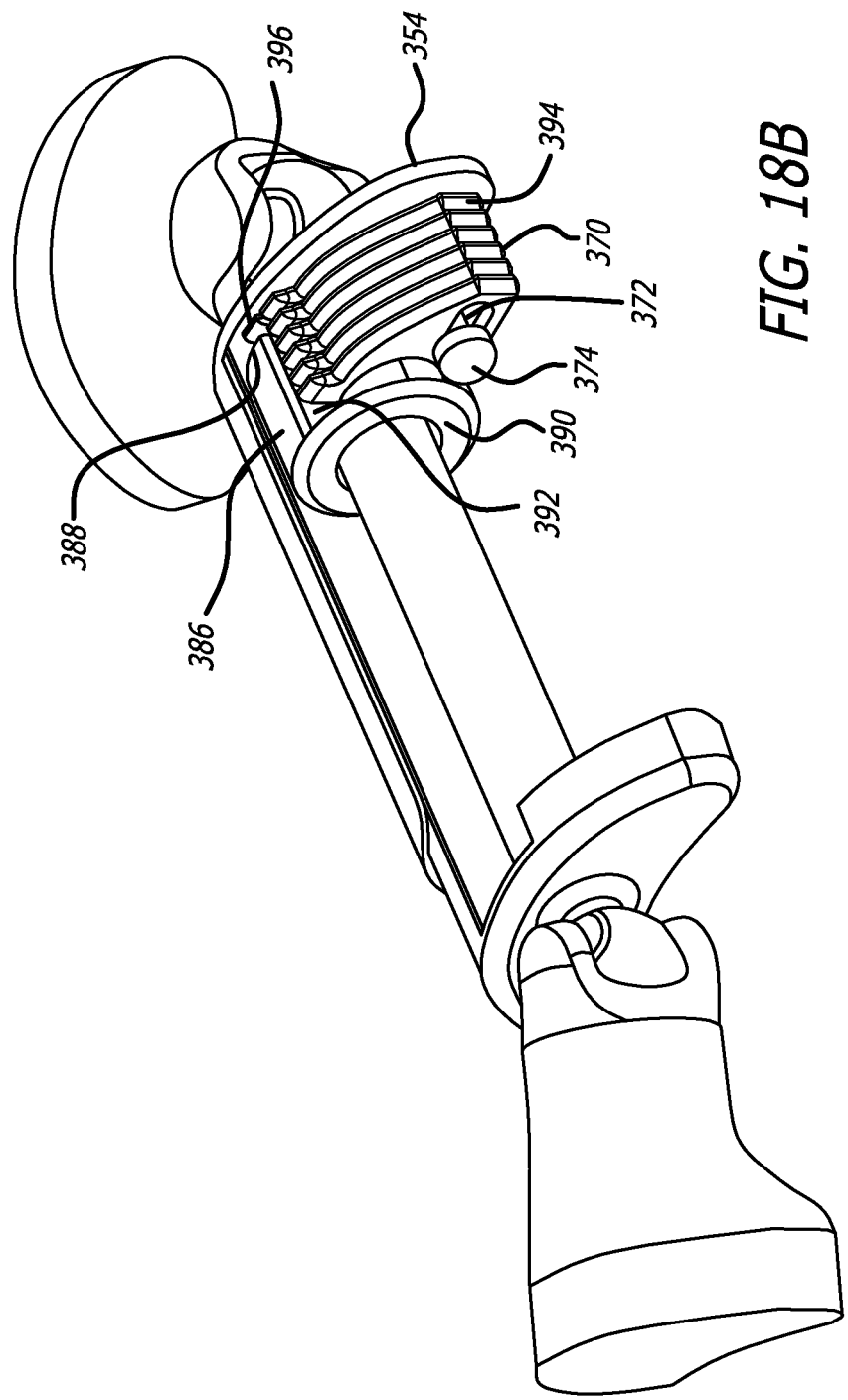
FIG. 18B is a partial perspective view of the energy absorbing device shown in FIG. 18A.

Another embodiment of an energy absorbing device 350a is shown in FIGS. 18A and 18B, and is similar to the embodiment of the device 350 shown in FIGS. 17A and 17B, and thus, like reference numerals will be used for like elements. In this embodiment, the arbor casing 356 includes a set of activation holes 384 on one side and a set of deactivation holes (not shown) on the opposite side of the arbor casing. This embodiment also includes a spring stop 386 with a proximal end 388 and a distal end 390 and a recess 392 designed to allow a plurality of shims to be stored in a deactivated state as best shown in FIG. 18B. To activate one of the shims, an instrument is inserted into the most proximal activation hole where it engages a first edge 394 of the shim, and forces the shim to rotate about the post 372 and slide in between the proximal end of the spring stop and the arbor base 354. Any number of the shims can be activated by inserting the instrument into consecutive activation holes starting from the proximal most hole. To deactivate the shims in this embodiment, the instrument is inserted into the distal most deactivation holes where it engages a second edge 396 of the shim and rotates the shim back into the deactivated position. FIG. 18B shows one shim activated.

Figure 19B:
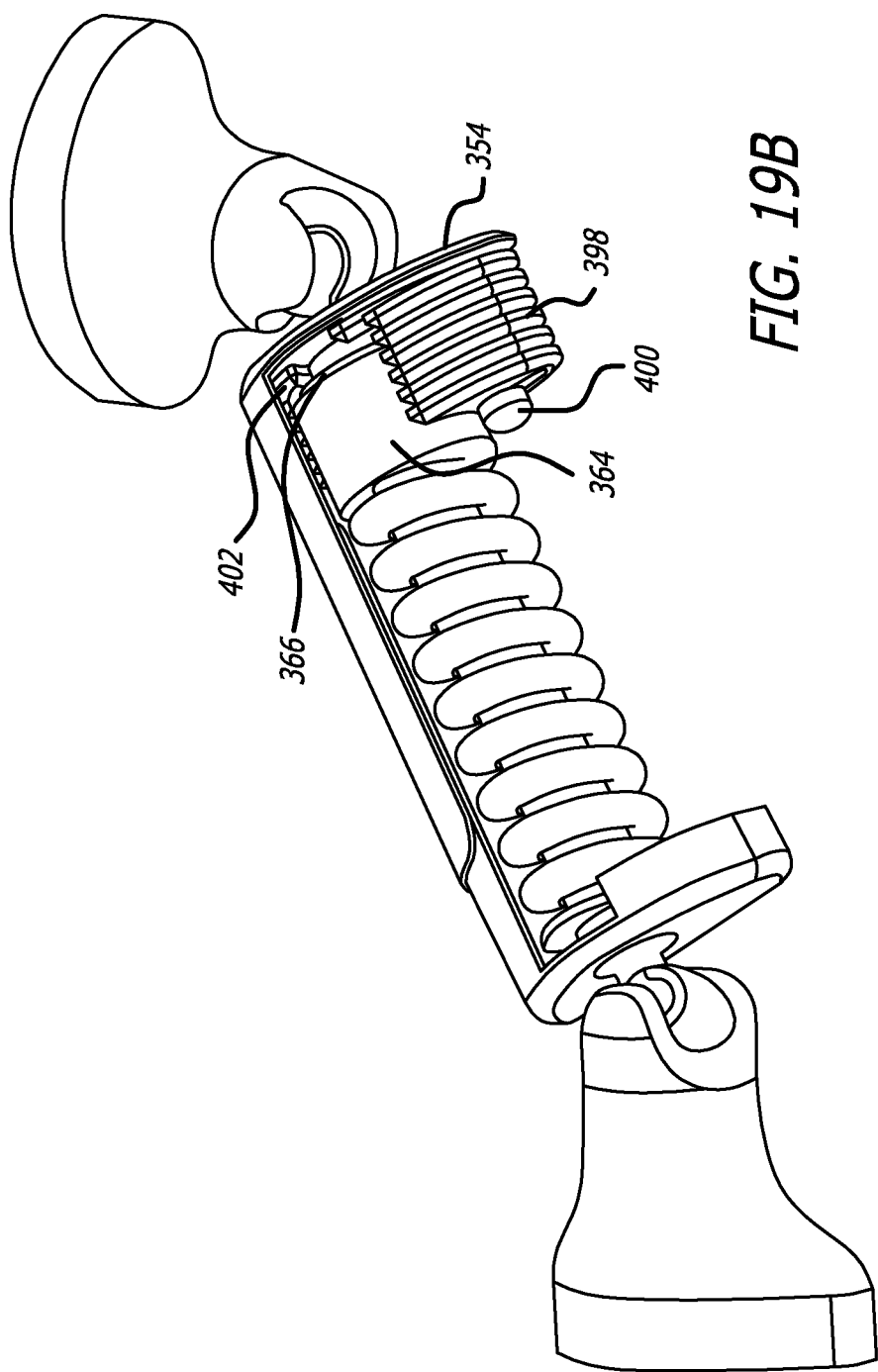
FIG. 19B is a partial perspective view of the energy absorbing device shown in FIG. 19A.

Another embodiment of an energy absorbing device 350b is shown in FIGS. 19A and 19B. In this embodiment, there is a first set of shims 398 on a first post 400 connected to the arbor base 354 on one side of the spring stop 364, and a second set of shims 402 on a second post (not shown) connected to the arbor base on the other side of the spring stop. There is a first set of activation holes 404 on one side of the arbor casing 356 and a second set of activation holes (not shown) on the other side of the arbor casing. The first and second sets of shims are activated by pressing an instrument into the most proximal holes of the first and second sets of activation holes, which rotates the shims in between the proximal end 366 of the spring stop and the arbor base. This action compresses the spring 352. To deactivate the shims, an instrument is inserted through the open top slot 406 of the arbor casing 356 and the piston casing 361 to rotate the shims back into the deactivated position near the wall of the spring stop. The user can deactivate any number of activated shims starting with the distal most activated shim.

Figure 20B:
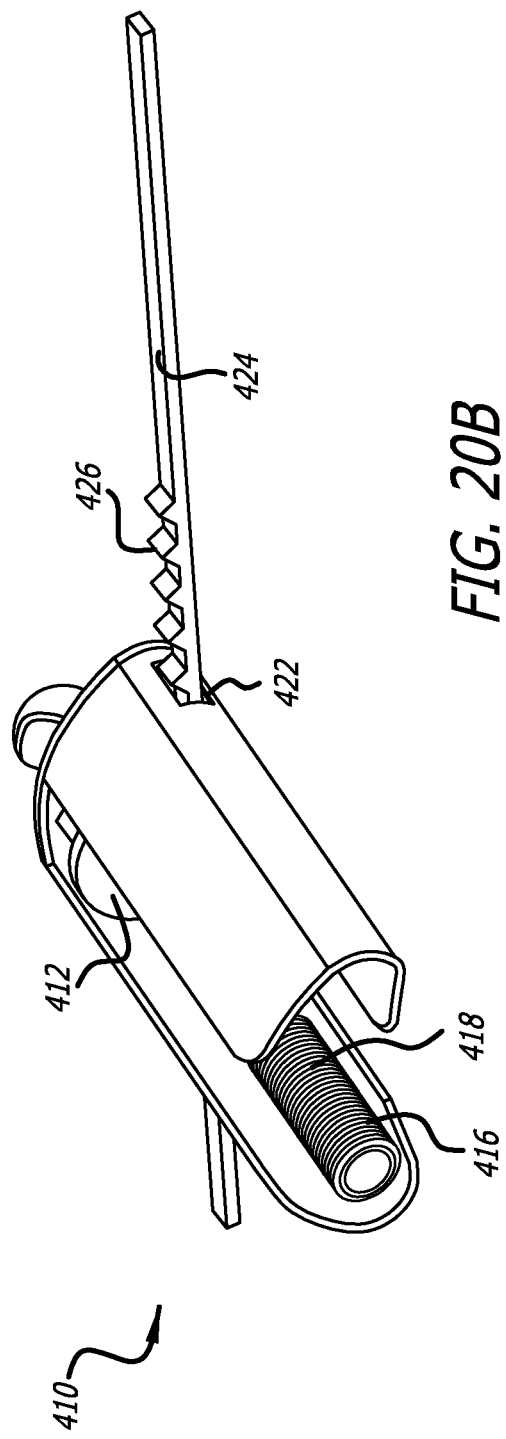

Referring now to FIGS. 20A and 20B, an energy absorbing device 410 is shown with the spring and piston base removed for clarity. The device of this embodiment includes a spring stop 412 with teeth 414 threaded onto a shaft 416 with threads 418 that is connected to the arbor base 420. An arbor casing or wall 421 includes a first opening 422 on one side and a second opening (not shown) on the opposite side of the casing. The first and second openings allows a tool 424 with teeth 426, such as a needle or rod, to be inserted into the casing to mesh with the teeth of the spring stop and rotate the spring stop in one of two directions. Pushing the tool to rotate the spring stop in one direction rotates the spring stop in a distal direction down along the threads of the arbor shaft. Rotating the spring stop in the opposite direction with the tool translates the spring stop in a proximal direction up along the threads of the arbor shaft. Translating the spring stop distally increases the compression on the spring and translating the spring stop proximally decreases the compression on the spring, thereby allowing the device to be adjusted to manipulate various loads.

Figure 21A:
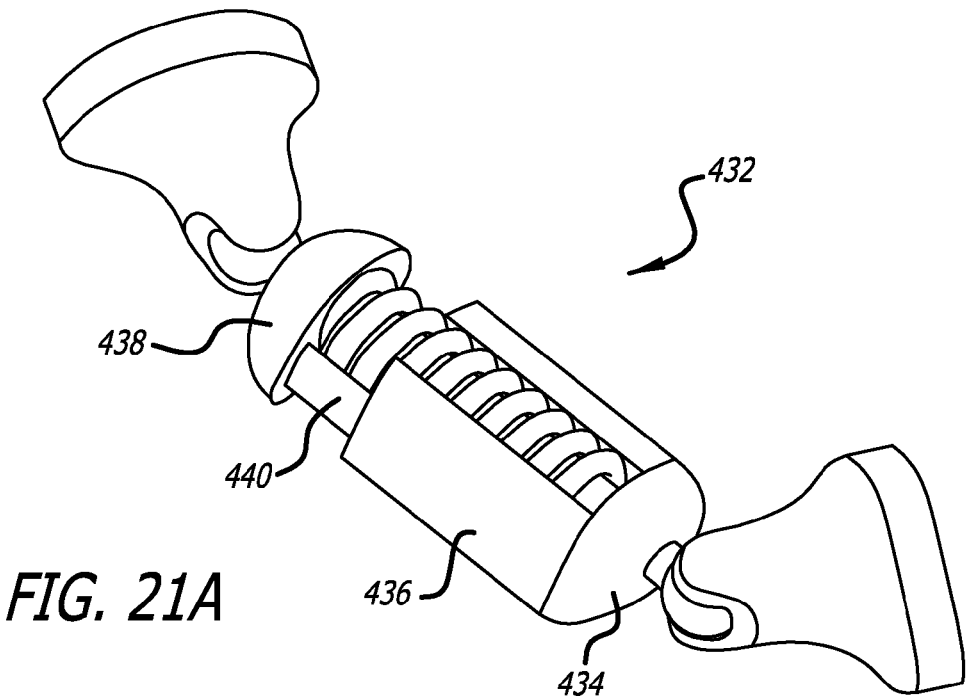
FIGS. 21A and 21B depict partial perspective views showing a non-circular single spring energy absorbing device with thickened walls.
Figure 21B:
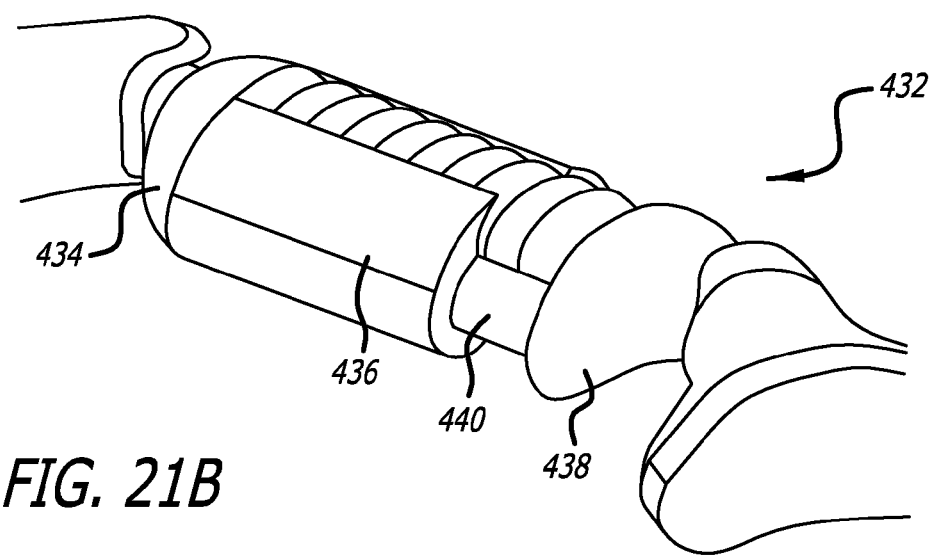

Another embodiment of an energy absorbing device 430 is shown in FIGS. 21A and 21B. In this embodiment, a non-circular link 432 is shown with an arbor base 434 having an arbor wall or casing 436, and a piston base 438 having piston wall or casing 440. The non-circular cross-section of the link allows the walls or casings of the bases to have added material making the walls thicker and therefore stronger. The added width of the walls will reduce rotation during load adjustments. The walls or casings of the energy absorbing devices 350, 350a, 350b, and 410 may be thin as previously shown or thicker as shown in FIGS. 21A and 21B.

Figure 22A:
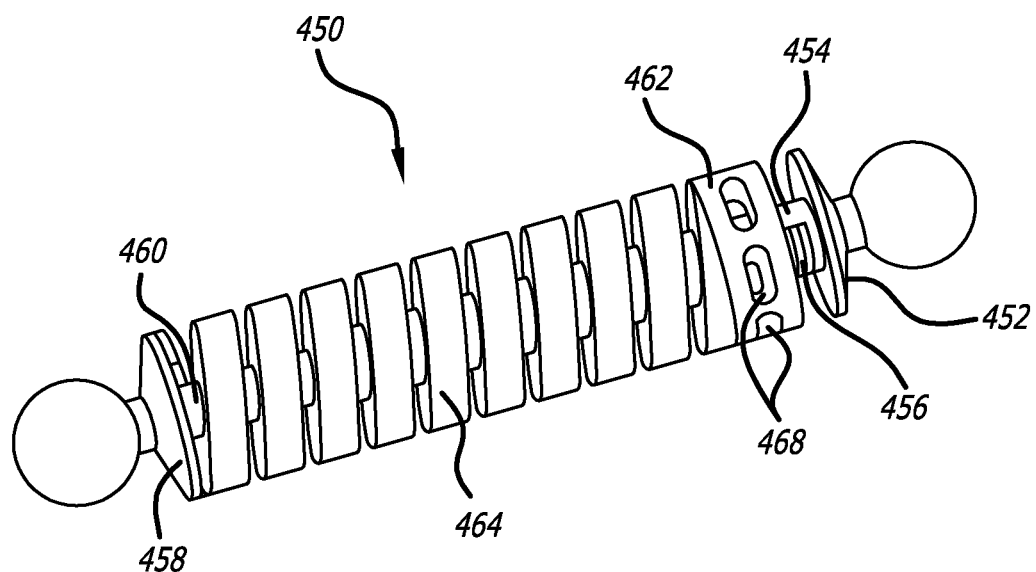
FIG. 22A is a perspective view, depicting an embodiment of a circular link element.
Figure 22B:
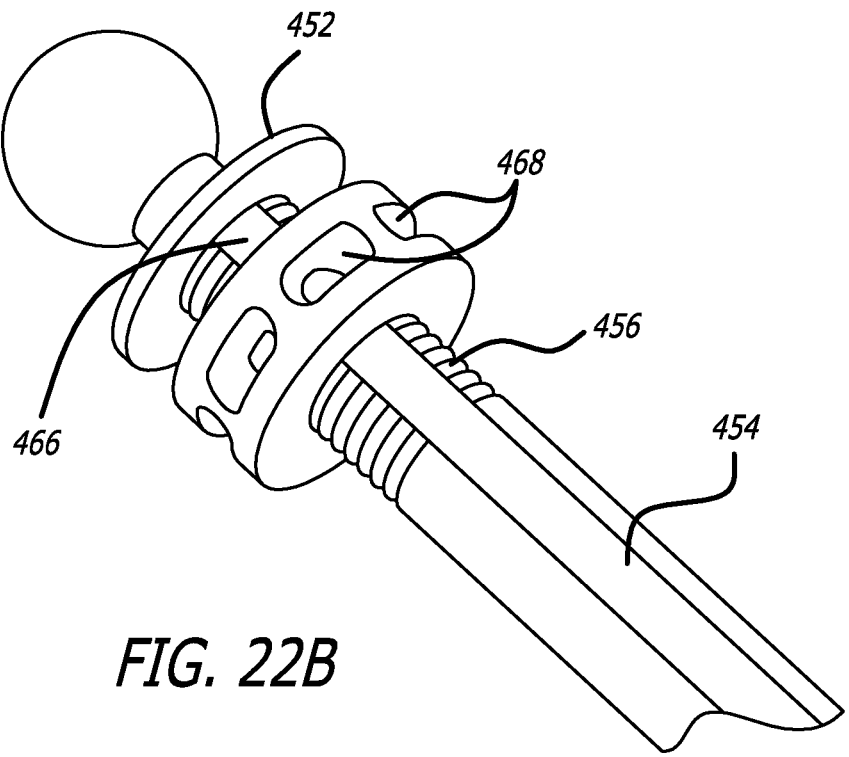
FIG. 22B is a partial perspective view, depicting the circular link element of FIG. 22A.

Other forms of links can be used in the energy absorbing system 100 to absorb any load placed on the system. As shown in FIGS. 22A and 22B, a circular link 450 is shown with an arbor base 452 including an arbor shaft 454 with threads 456, and a piston base 458 including a piston 460 that slides within the arbor shaft. There is also a spring stop 462 that is threaded onto the threads of the arbor shaft, and the spring stop is in contact with a compression spring 464 that is in between the spring stop and the piston base. There is a small finger lock 466 located on the arbor shaft that locks the rotational position of the spring lock. To unlock the spring stop to adjust the load of the device, a tool, such as a 2 mm rod, is inserted into the top of the link to depress the finger lock, moving it away from a groove within the spring stop. With the spring stop unlocked, the rod is positioned through a radial divot 468 of the spring stop. Adjustment occurs via multiple up and down actions or rocker of the rod. Depending on the pitch of the threads on the arbor shaft, compression or decompression of the spring can range from between about 1 mm to about 3 mm.

Figure 23A:
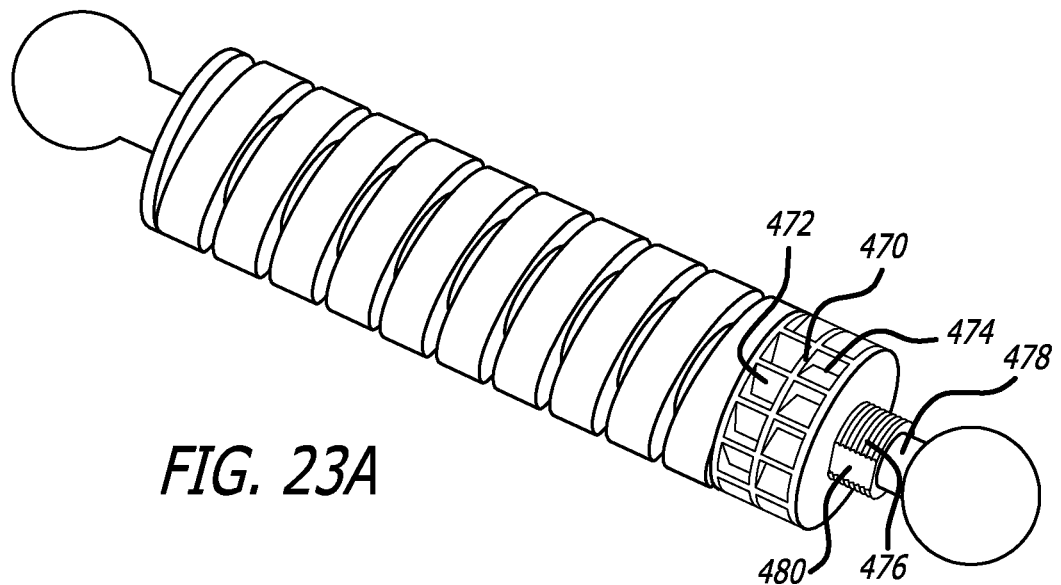
FIG. 23A is a perspective view, depicting another embodiment of a circular link element.
Figure 23B:
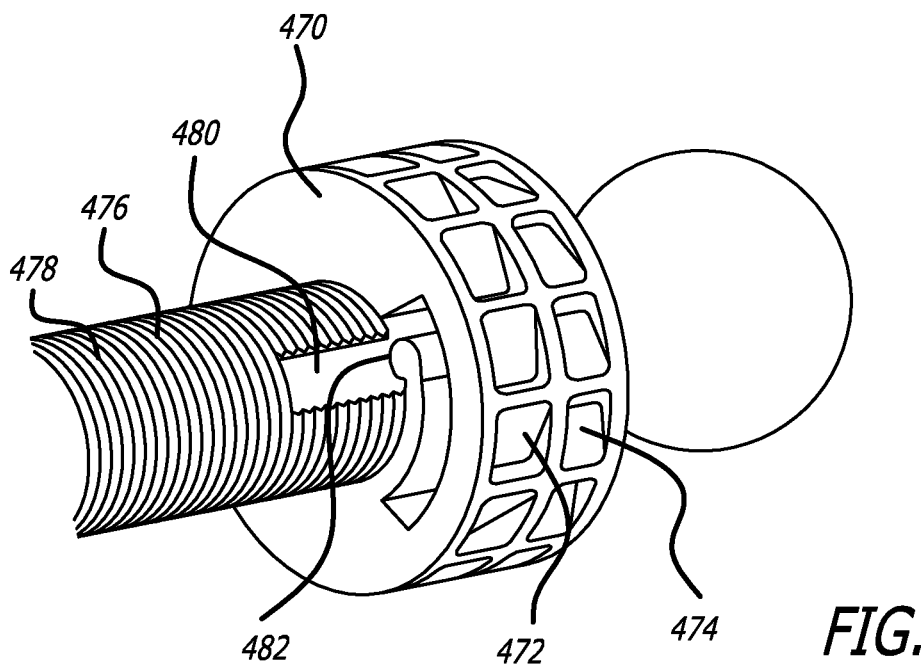
FIG. 23B is a partial perspective view, depicting the circular link element of FIG. 23A.

FIGS. 23A and 23B show another approach of a spring stop 470 that includes a first set of sloped notches 472 and a second set of sloped notches 474 that are sloped opposite to the first set. The spring stop is threaded onto threads 476 of arbor shaft 478. There is also a recess 480 disposed through the threads of the shaft. A spring finger 482 (see FIG. 23B) is built into the spring stop and engages the recess of the shaft. To further compress a spring 484, the spring stop is translated in one direction using repeated rocking motions with a tool, such as a 2 mm rod, that engages the first set of sloped notches. The spring stop will longitudinally translate until the spring finger snaps into the recess of the shaft making an audible click. This audible click tells the user that the spring stop has been re-seated, which results in moving the spring stop about 1 mm, or more depending on the pitch of the threads on the shaft. To adjust the device by decreasing the compression on the spring, the spring stop is translated in the opposite direction using the tool to engage the second set of sloped notches in a repeated motion.

Figure 24A:
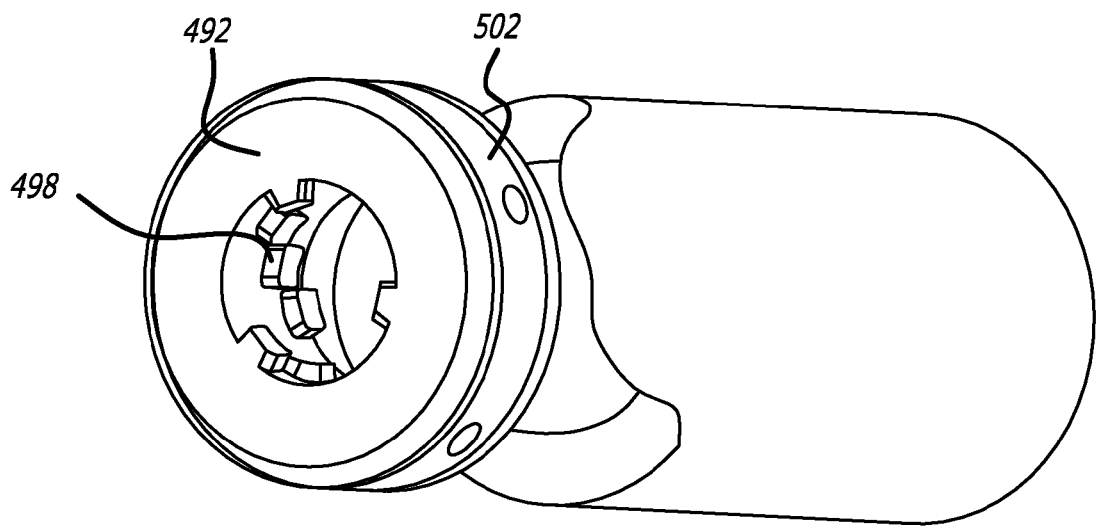
FIG. 24A is a perspective view, depicting an embodiment of a spring stop.
Figure 24B:
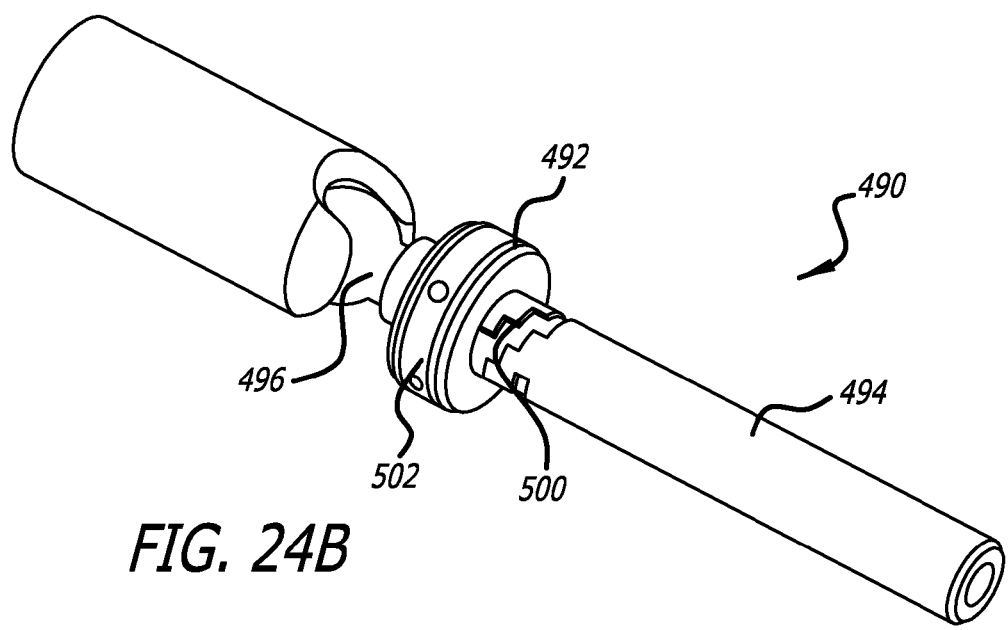
FIG. 24B is a partial perspective view, depicting the spring stop of FIG. 24A disposed on a shaft.

Yet another approach of a link 490 is shown in FIGS. 24A and 24B. In this embodiment a spring stop 492 is disposed on a shaft 494 of an arbor base 496. The inner surface of the spring stop includes raised bumps or teeth 498 that mesh with grooves 500 disposed on the arbor shaft. There is also a spring lock 502 on the spring stop that locks the spring stop in position on the shaft. To unlock the spring stop, a tool, such as a 1-2 mm rod, is inserted into the spring lock. The unlocked spring stop is then free to slide distally about 1 mm then rotate about 30° to lock in place. This helical movement can compress the spring (not shown) in order to adjust the device. The spring stop can also be unlocked and moved proximally about 1 mm then rotated 30° in the reverse direction and locked in place to decrease the compression of the spring (not shown). The spring stop may slide distally or proximally more or less than 1 mm depending on the design of the grooves on the shaft.

Figure 25A:
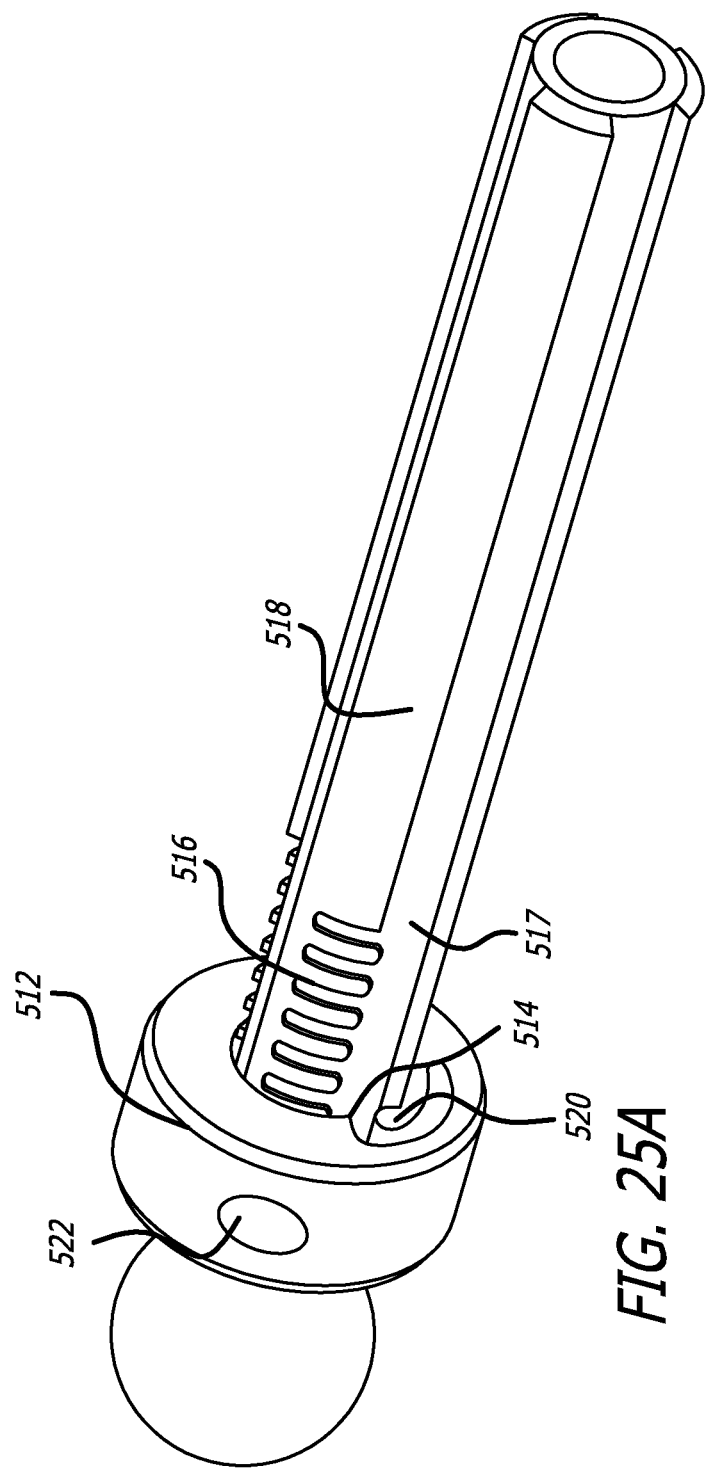
FIGS. 25A and 25B depict partial perspective views of another embodiment of a spring stop disposed on a shaft.
Figure 25B:
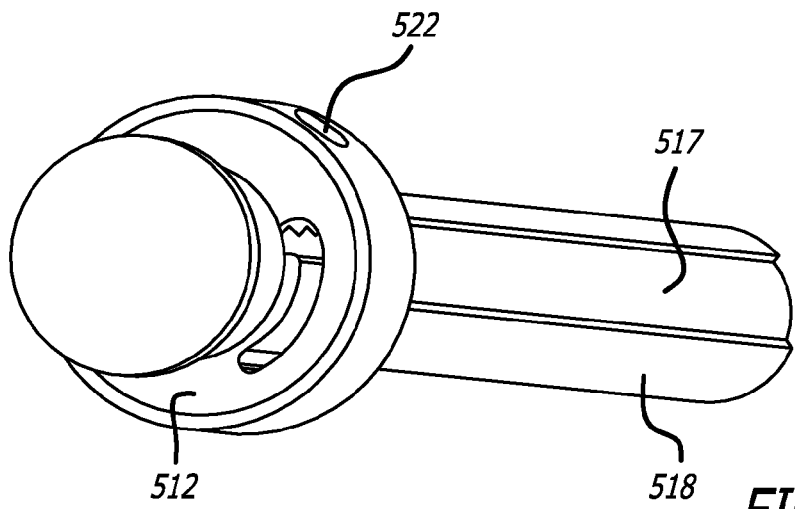

Another embodiment of a link 510 is shown in FIGS. 25A and 25B. The link includes a spring stop 512 having a tooth 514 on its inner surface to engage grooves 516 and a recess 517 on an arbor shaft 518. The spring stop also includes a spring finger 520 that prevents the spring stop from rotating or disengaging the grooves or recess of the shaft. To unlock the spring stop, the spring stop is rotated about 60° via a tool, such as a 2 mm rod, that is inserted into an opened or closed end hole 522 of the spring stop. The amount of rotation can be reduced by increasing the number of radial teeth sets on the shaft. Once unlocked, the spring stop is slid along the shaft to a new location and then rotated back 60° to lock the spring stop in position.

Figure 26:
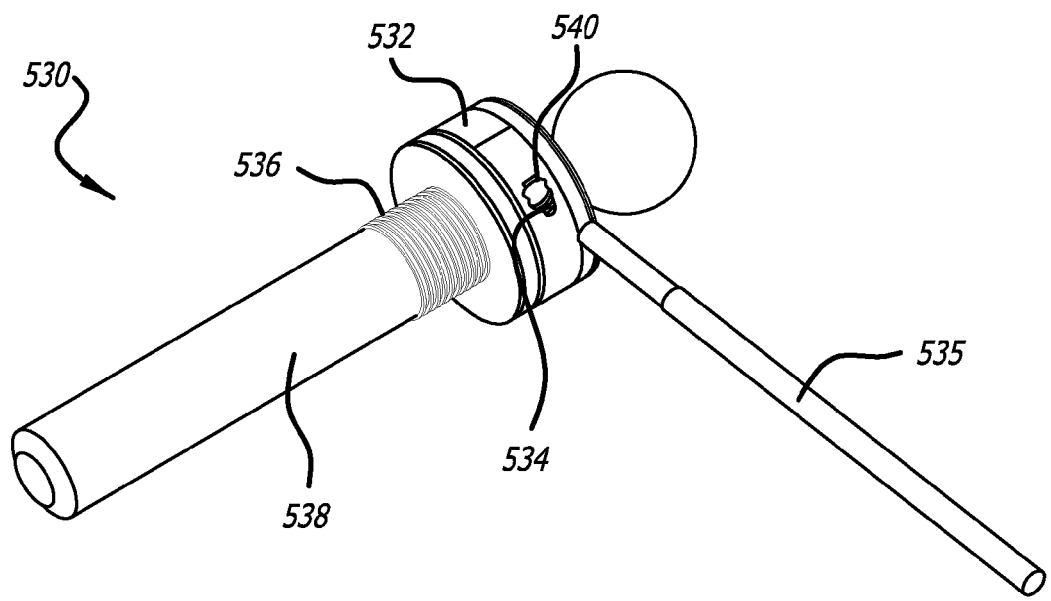
FIG. 26 is a partial perspective view, depicting yet another embodiment of a spring stop disposed on a shaft.

Referring now to FIG. 26, a link 530 is shown having a split-ring spring stop 532 with a turnbuckle 534. Inserting a tool, such as a hex tool 535, into the turnbuckle separates the split-ring to allow translation of the split ring to the next set of teeth 536 on a shaft 538, and creates the shift via teeth on the hex receiving part 540. The split-ring can be translated proximally or distally to adjust the load manipulating characteristics of the energy absorbing system.

Figure 27:
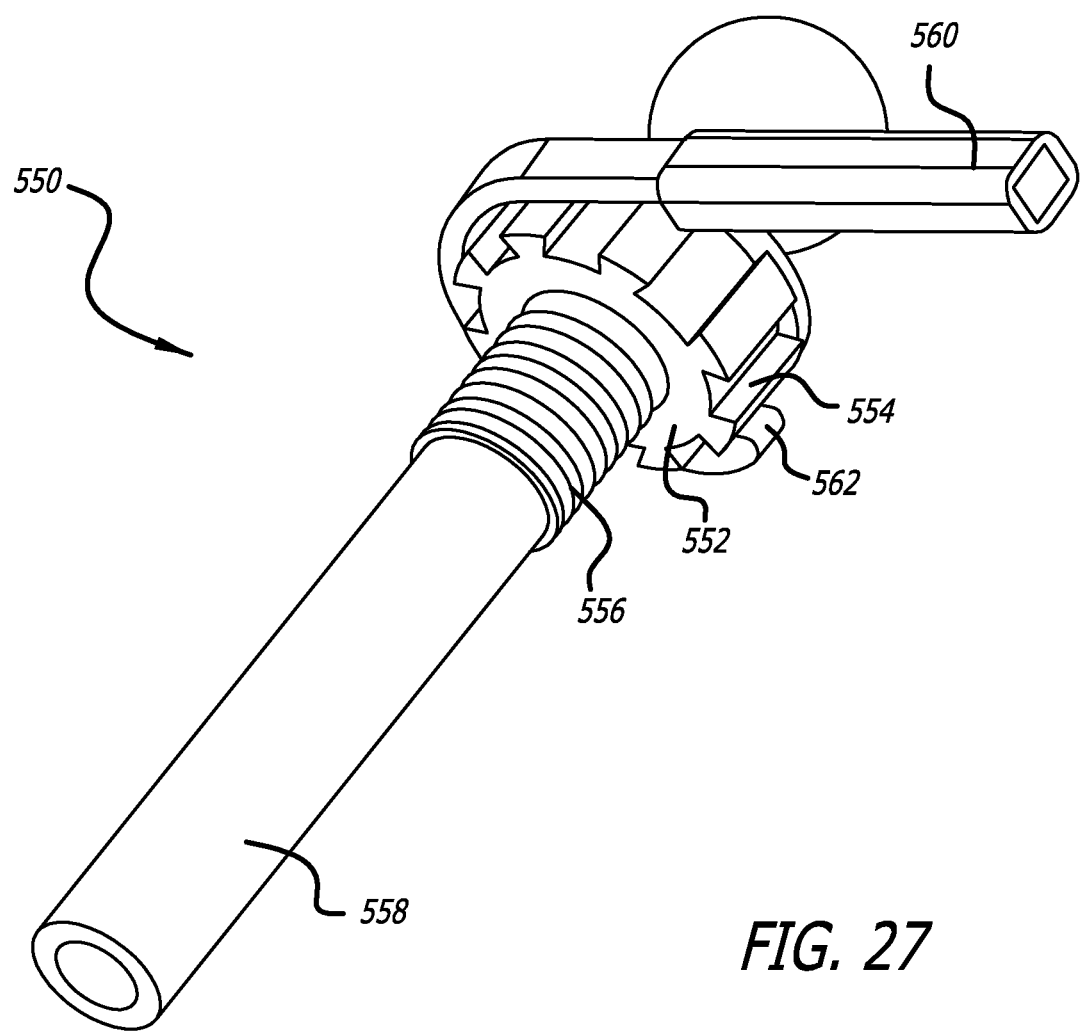
FIG. 27 is a partial perspective view, depicting another embodiment of a spring stop disposed on a shaft.

FIG. 27 shows another embodiment of a link 550 having a spring stop 552 with teeth 554 that is threaded onto threads 556 of a shaft 558. A tool 560 with a preformed internal member and a hook 562 slides out of a sheath (not shown) and wraps around the teeth of the spring stop. Pulling the tool creates rotation of the spring to translate the spring stop along the threads of the shaft. This allows adjustment of the energy absorbing device by increasing or decreasing the compression of the spring (not shown).

Figure 28:
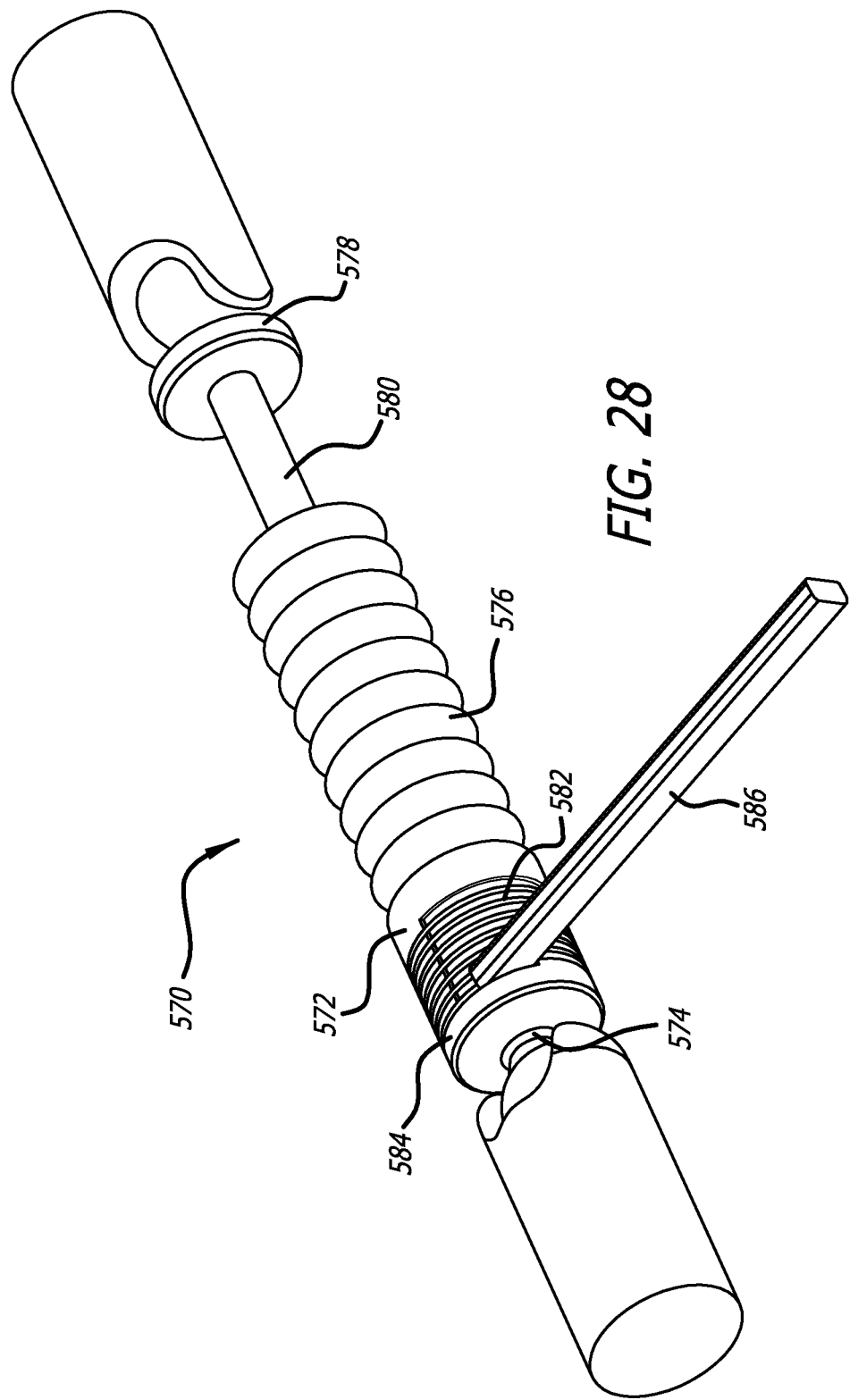
FIG. 28 is a perspective view, depicting an embodiment of a circular link with zero load on a spring showing flexible helical shims being disposed around a shaft to adjust the load of the circular link.

Another embodiment of a link 570 is shown in FIG. 28. In this embodiment a spring stop 572 is disposed over a shaft of an arbor base 574. A spring 576 is positioned over the shaft and is located between the spring stop and a piston base 578. The piston base includes a piston or rod 580 that slides within the arbor shaft. To adjust the device, flexible helical shims 582 are inserted or removed from around the arbor shaft proximate to the spring stop. An accessible housing 584 may be integrated with the spring stop or positioned proximate to the spring stop to capture the helical shims. A tool 586, such as a cannula or needle with a rectangular cross-section, is used to insert shims into the accessible housing. A tip of the tool is inserted into the accessible housing and flexible helical shims are elastically deformed into a generally straight line to be transported through the tool and into the housing where the shims recoil or spring around the arbor shaft. As shown in FIG. 28, the energy absorbing device is extended with zero load on the spring 576. There are six shims in position proximal to the spring stop, giving adjustability from about 0 mm to about 6 mm. Shims may also be removed to adjust the profile of the load manipulation of the device.

Figure 29A:
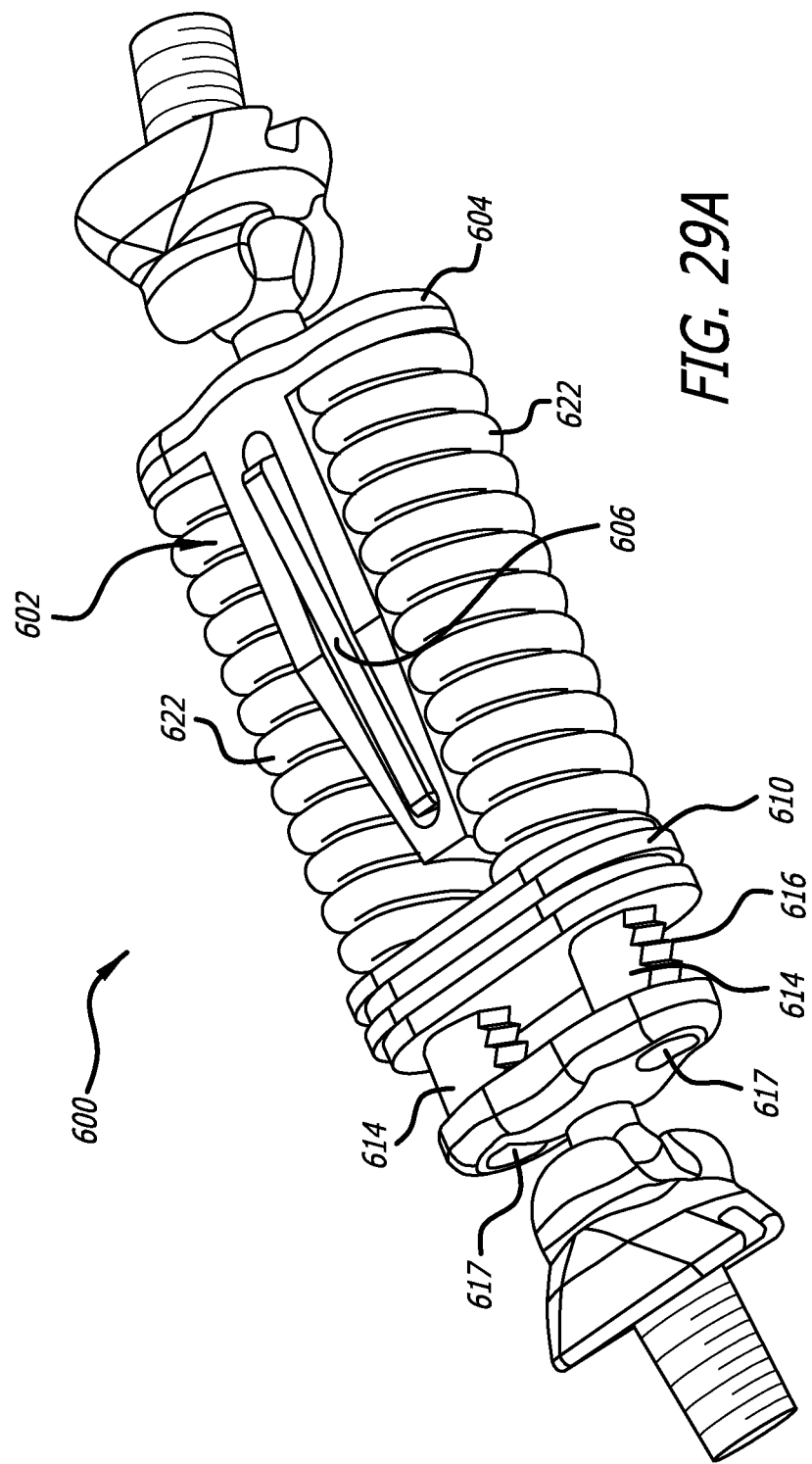
FIG. 29A is a perspective view, depicting a further embodiment of an energy absorbing device.
Figure 29B:
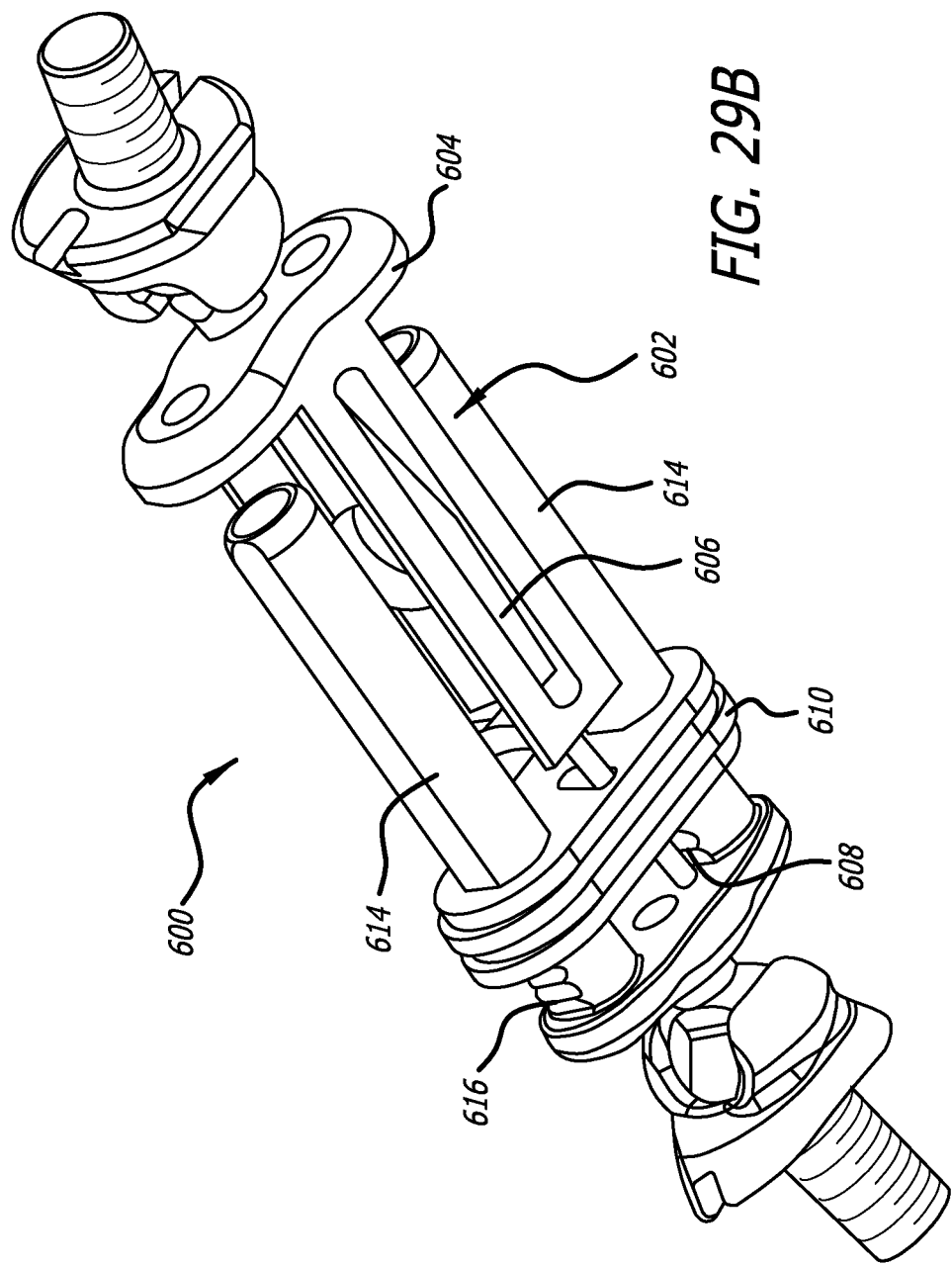
FIG. 29B is a perspective view, depicting an opposite side of the device of FIG. 29A with compression springs removed.
Figure 29C:
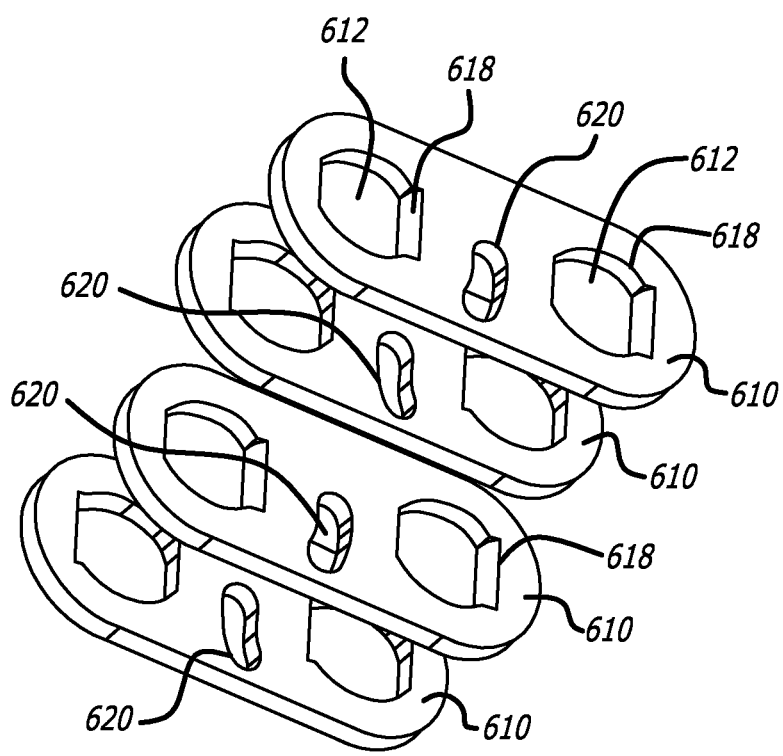
FIG. 29C is a perspective view, depicting the adjustment core plates of FIGS. 29A and 29B.

An energy absorbing device 600 incorporating a push down mechanism for unlocking a load adjustment mechanism is depicted in FIGS. 29A-C. In this embodiment, the device is provided with a piston base assembly 604 including a pivotable switch 606 including a bar extension 608. The device 600 further includes a series of adjustable core plates 610, here shown including four such plates. Each plate includes a pair of spaced holes 612 sized to receive a single arbor shaft 614 as with previously described approaches. It is noted that the arbor shafts extend from an arbor base including relief holes 617 in communication with bores for receiving the piston shafts. Such relief holes 617 can be incorporated as described into each of the disclosed embodiments to aid in avoiding binding of the piston shafts. Moreover, the relief holes 617 can be valved so that body fluid is drawn in during flexion of anatomy and thus, the structure acts as a pneumatic absorber for extension of the anatomy. The arbor shafts 614 include angled teeth 616 which engage corresponding structure forming a perimeter of the spaced holes. This corresponding structure can be in the form of ramps 618 which can be locked between the teeth 616 formed on the arbor shafts 614. The interaction between the core plates 610 and the arbor shafts 614 can provide the tactile or audible feedback necessary to indicate relative movement between the parts.

Each of the plates 610 also include a curved center slot 620, adjacent plates 610 having oppositely curved center slots 620.

The slots 620 are configured to receive the bar arm 608 of the pivotable switch 606, which extends generally perpendicularly through the plates 606.

Upon depression of the switch 606 an audible or tactile feedback can indicate the unlocking of the plates 610 from their engagement with the arbor shafts 614. That is, in a first position, the bar arm 608 of the switch 606 can lock the plates 610 within the teeth 616 of the arbor shafts 614. Once the switch 60 is depressed and caused to pivot, the bar arm 608 moves within the center curved slots 620 of the plates 610, thereby allowing relative lateral movement of the plates to occur. The lateral movement results in disengaging the plates from the arbor shafts 614 to an extent allowing the translation of the plates along the arbor shafts 614. By doing so, the operating length of the compression springs 622 can be altered to thereby adjust the range of the load and energy absorbing capabilities of the energy absorbing device 600. It is further contemplated that a tactile or audible click be induced as the plates 610 are moved along the arbor shafts 614. The switch 606 can then be depressed again to once again lock the plates 610 relative to the arbor shafts 614.

Figure 30A:
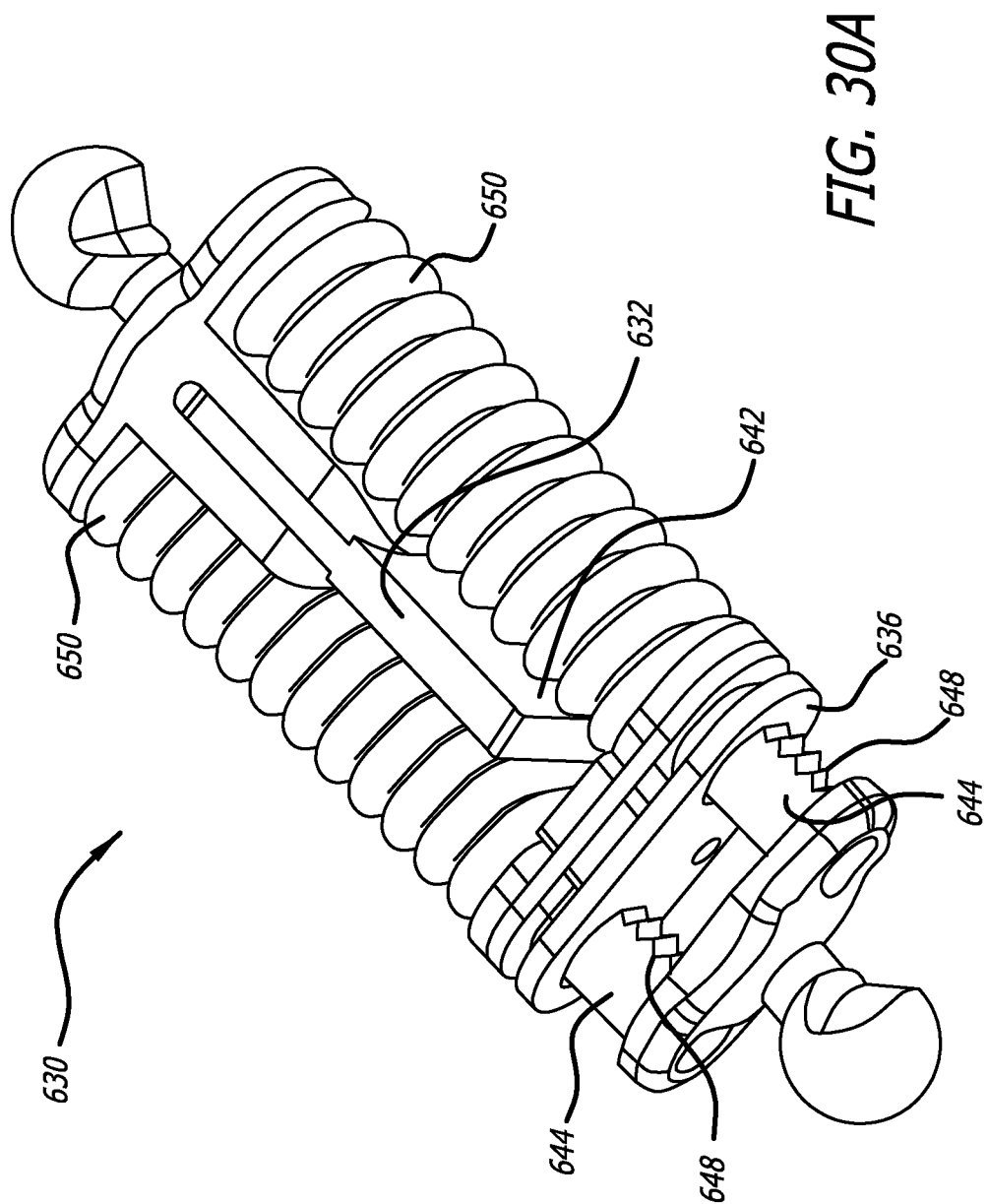
FIG. 30A is a perspective view, depicting yet a further embodiment of an energy absorbing device.
Figure 30B:
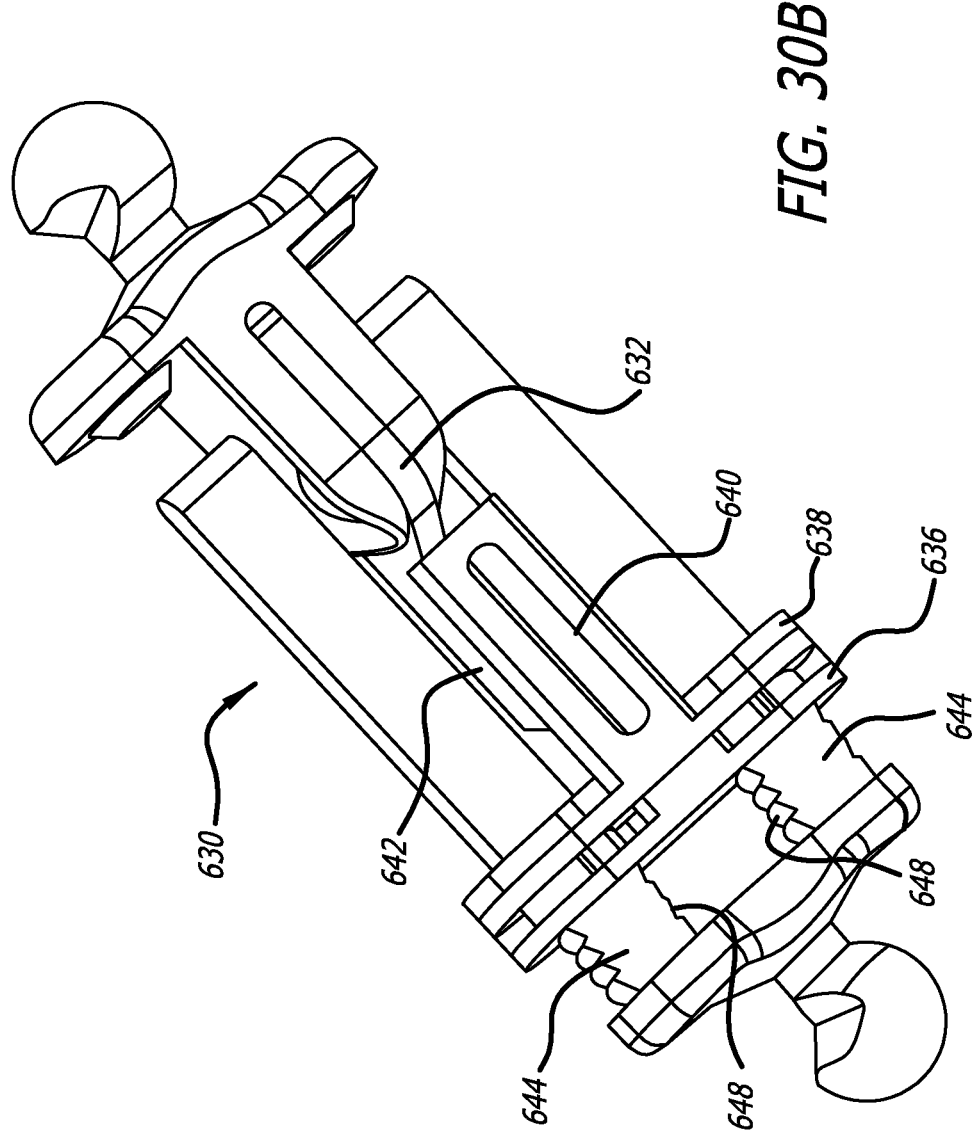
FIG. 30B is a perspective view, depicting an opposite side of the device of FIG. 30A with compression springs removed.
Figure 30C:
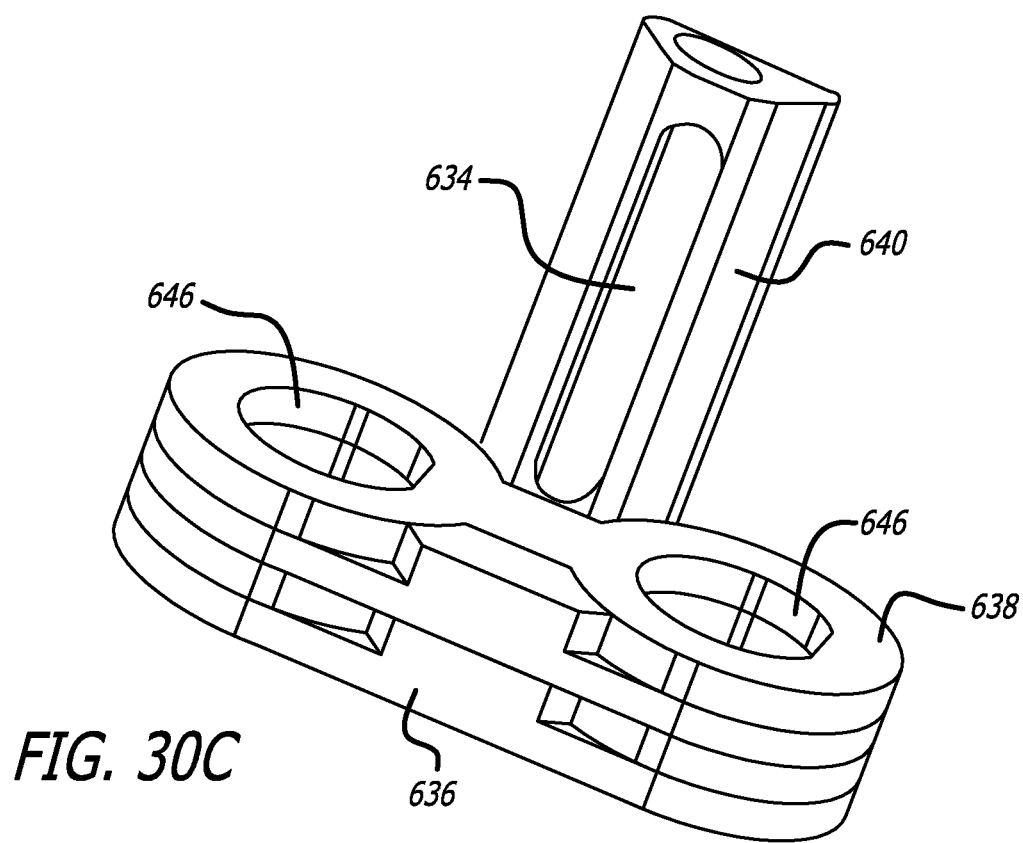
FIG. 30C is a perspective view, depicting the adjustment core assembly of FIGS. 30A and 30B.

In a related approach, as shown in FIGS. 30A-C, an energy absorbing device 630 includes a pivotable switch 632 which interacts with a bar arm 634 extending from one of two adjustment core plates. A first adjustment core plate 636 includes the bar arm 634 which extends therefrom in a generally perpendicular manner. The second adjustment plate 638 includes a channel 640 having an interior for receiving the bar arm 634. The switch 632 includes a terminal end portion 642 which engages the bar arm 634 such that in a first position, the terminal end portion 642 forces the bar arm 634 against an internal wall of the channel 640 to lock the plates 636, 638 in a longitudinal position along arbor shafts 644. In this embodiment as well, the plates 636, 638 include spaced through holes 646 sized and shaped to both receive the arbor shaft as well as lockingly engage teeth 648 formed on the arbor shaft 644. Moreover, such engagement is contemplated to provide auditory or tactile feedback necessary to indicate relative movement.

Upon depression of switch 632, the engagement between its terminal end portion 642 and the bar arm 634 of the plate 636 is relieved. This action allows the plates 636, 638 to slide laterally with respect to each other and out of a locking engagement with the arbor shaft 644. At this stage the plates 636, 638 can be moved longitudinally along the arbor shafts to thereby adjust the range of the load manipulation capabilities of the compression springs 650. The switch can then be depressed again, or alternatively simply released depending upon the particular configuration of the switch, to lock both the plates 636, 638 in position. This locking and unlocking action can again be associated with a feedback mechanism to alert the operator of status.

Figure 31B:
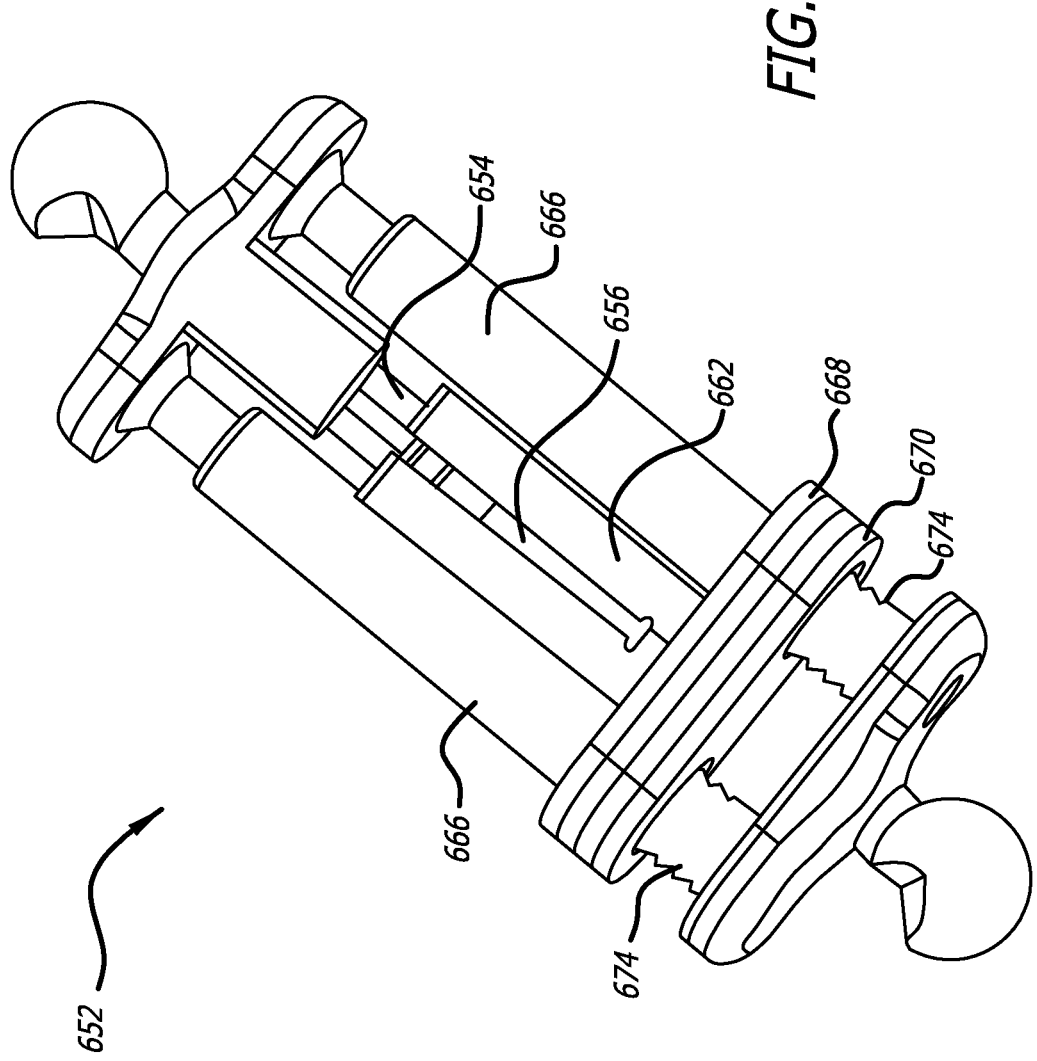
FIG. 31B is a partial perspective view, depicting an opposite side of the device of FIG. 31A with compression springs removed.
Figure 31C:
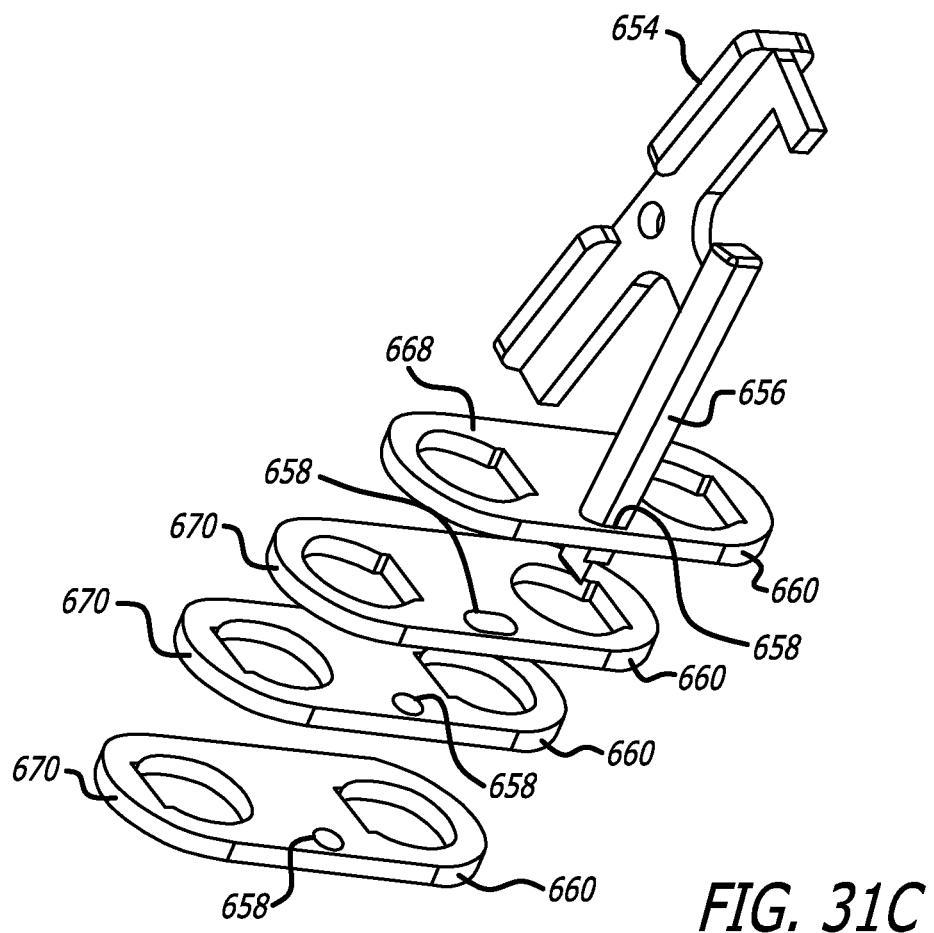
FIG. 31C is a perspective view, depicting the core adjustment subassembly of FIGS. 31A and 31B.

Turning now to FIGS. 31A-C, another embodiment of an energy absorbing device 652 including a switch is described. In this approach, the device 652 includes a pivoting switch 654 operatively connected to a pin 656. Operation of the switch 654 results in longitudinal motion of the pin 656 through center holes 658 formed in adjustment plates 660. Both the switch 654 and the pin 656 ride within a center extension 662 which is configured between springs 664 configured about arbor shafts 666. One end of the center extension abuts a center most positioned adjustment plate 668 of a stack of adjustment plates 670. Here also, the adjustment plates 668, 670 include holes 672 for locking engaging teeth 674 of the arbor shafts 666 in a manner to provide feedback upon relative movement. The center holes 658 are again positioned and shaped to both cause the plates to lockingly engage the arbor shafts 666 as well as to move laterally with respect to one another upon activation of the switch 654. When disengaged from a locking position, the adjustment plates 668, 670 can be translated along the arbor shafts to adjust the springs 664.

Referring now to FIGS. 32A-D, yet another approach is described. Thus, it is further contemplated that an energy absorbing device 680 include structure preventing accidental unlocking of adjustment structure. As with all of the disclosed embodiments, audible or tactile feedback is incorporated into the device 680 to alert the patient or operator as to status concerning a locked or unlocked state as well as relative movement of parts during adjustment. Adjustment core plates 682, 684 each include curved wings 686 which extend longitudinally along the device 680 exterior of springs 688 configured about arbor shafts 690. Moreover, the plates 682, 685 each include spaced holes 692 with perimeter for lockingly engaging teeth 694 formed on the arbor shafts 690 and for providing necessary feedback concerning positioning or movement.

The energy absorbing device 680 also includes a piston base 696 including a center extension 697 configured between the springs 688. At an opposite side of the device 680 and adjacent the arbor base 697 there is positioned a center extension 698.

Figure 32A:
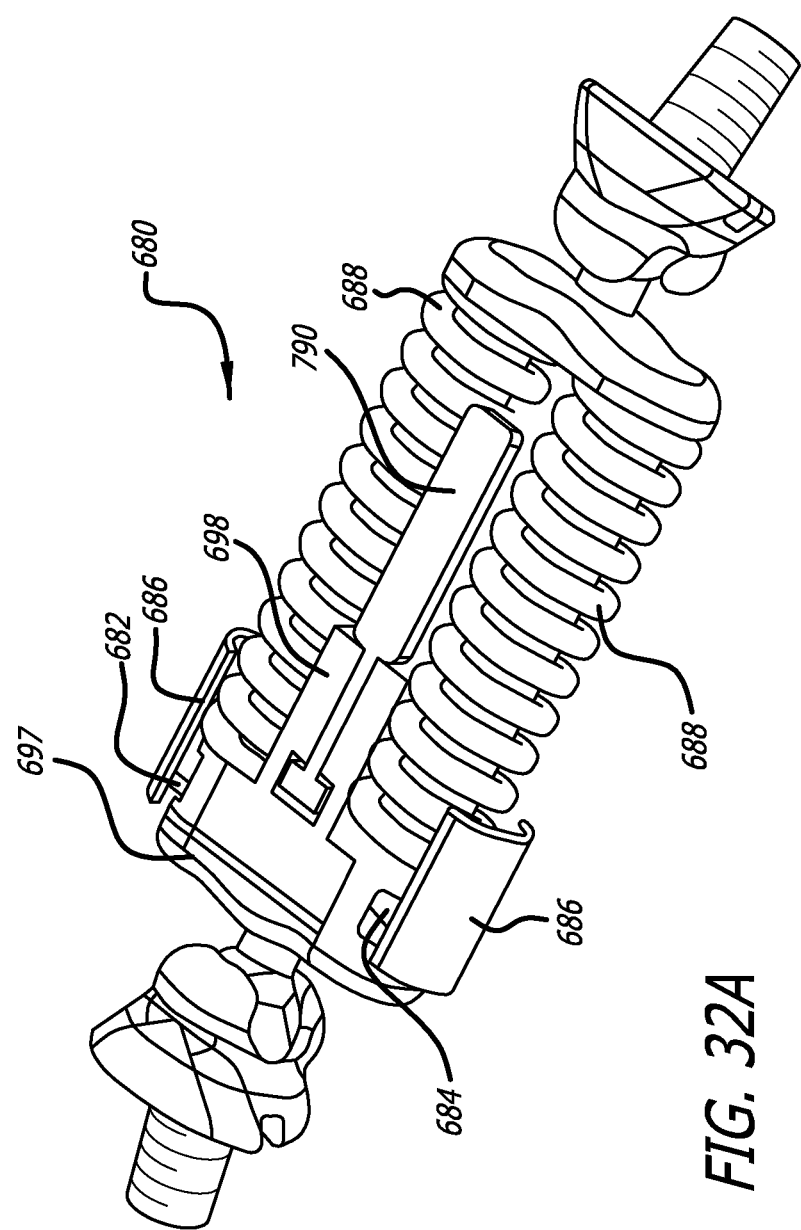
FIG. 32A is a perspective view, depicting an energy absorbing device including center and side squeeze mechanisms.
Figure 32B:
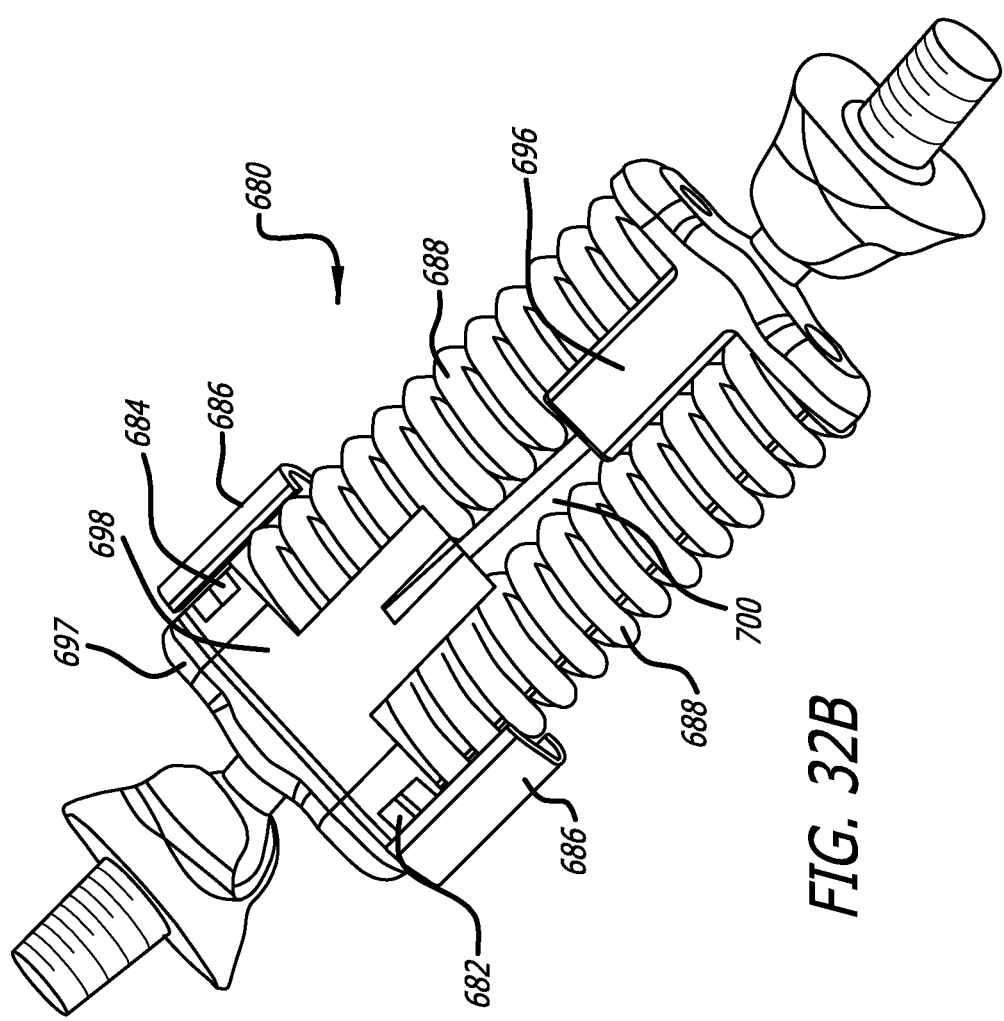
FIG. 32B is a perspective view, depicting an opposite side of the device depicted in FIG. 32A.
Figure 32C:
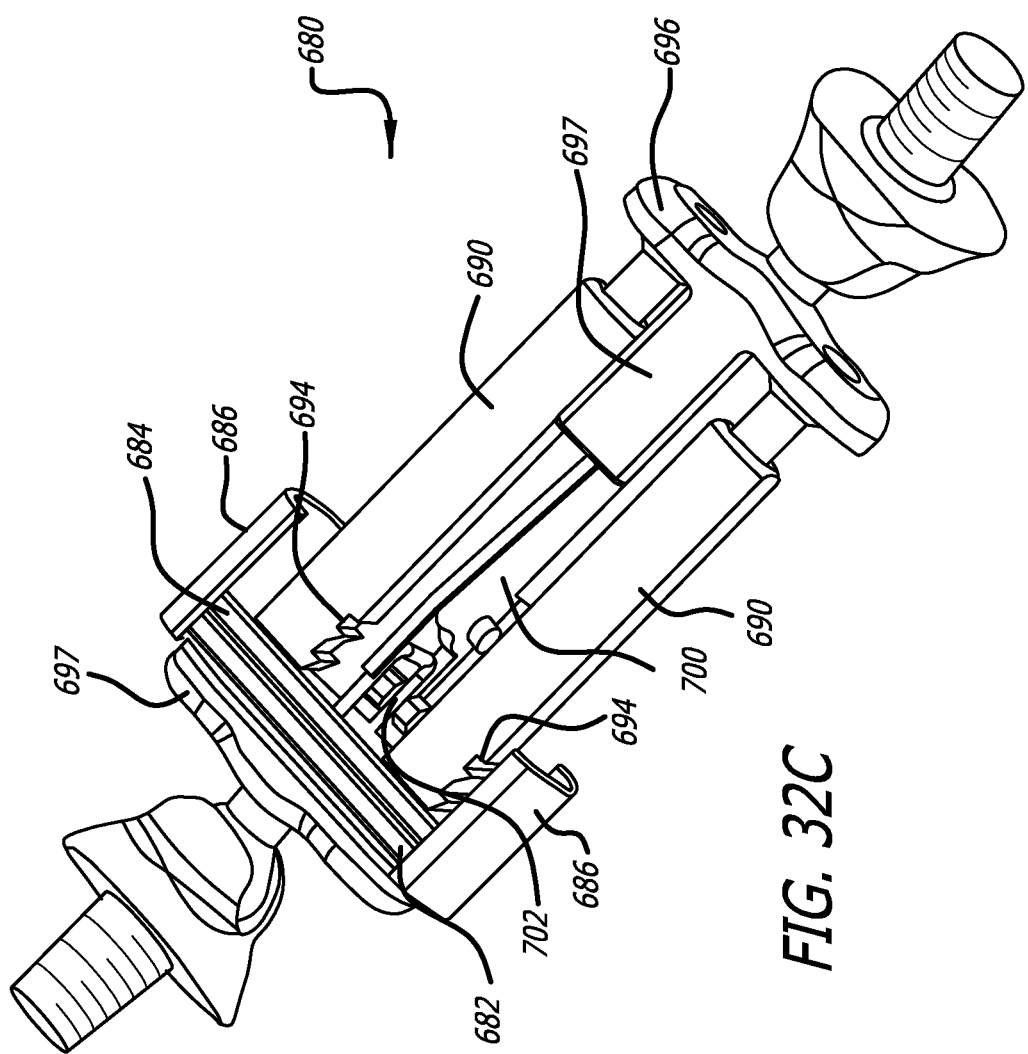
FIG. 32C is a perspective view, depicting the device of FIG. 32B with compression springs removed.
Figure 32D:
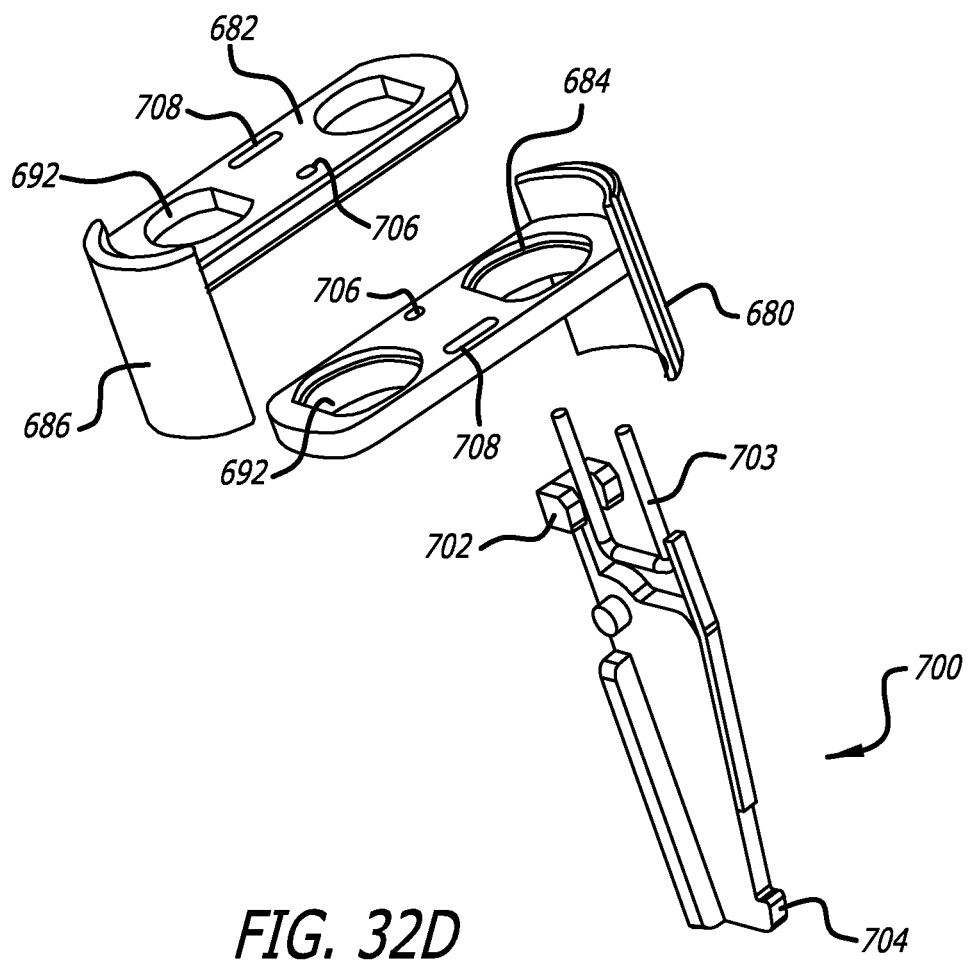
FIG. 32D is a perspective exploded view, depicting components of the adjustable subassembly of FIGS. 32A-C.

Pivotably attached to the center extension 698 is a switch 700 assembly. As best seen in FIG. 32D, the switch assembly includes a first extension 702 including a slot sized to receive a U-spring 703 and a second opposite end portion equipped with a tail 704. The tail 704 is sized and shaped to lockingly engage corresponding structure (not shown) formed in the piston base extension 697. The U-spring 703 includes ends 705 which extend through holes both round 706 and slotted 708, formed in the plates 682, 685.

In use, the switch assembly 700 operates to retain the U-spring 703 in an orthogonal position through its engagement with the adjustment plates 682, 684. The U-spring 703 in turn locks the adjustment plates 686, 684 against the arbor shafts 690 and within its teeth 694. Upon depression of the switch 700, the extension 702 disengages from the U-spring 703 thereby permitting the U-spring to be bent and thus, unlocking the device. Next, the curved wings 686 of the adjustment plates 682, 684 can be depressed to disengage the plates from the teeth 694 of the arbor shafts 690 so that translation of adjustment components is possible. As previously described, such translation results in altering when the compression springs will manipulate loads. The wings 686 are then released to set the longitudinal position of the plates on the arbor shaft. After desired adjustment is accomplished, the switch can be re-seated to thereby again lock the plates 682, 684 in position.

Figure 33A:
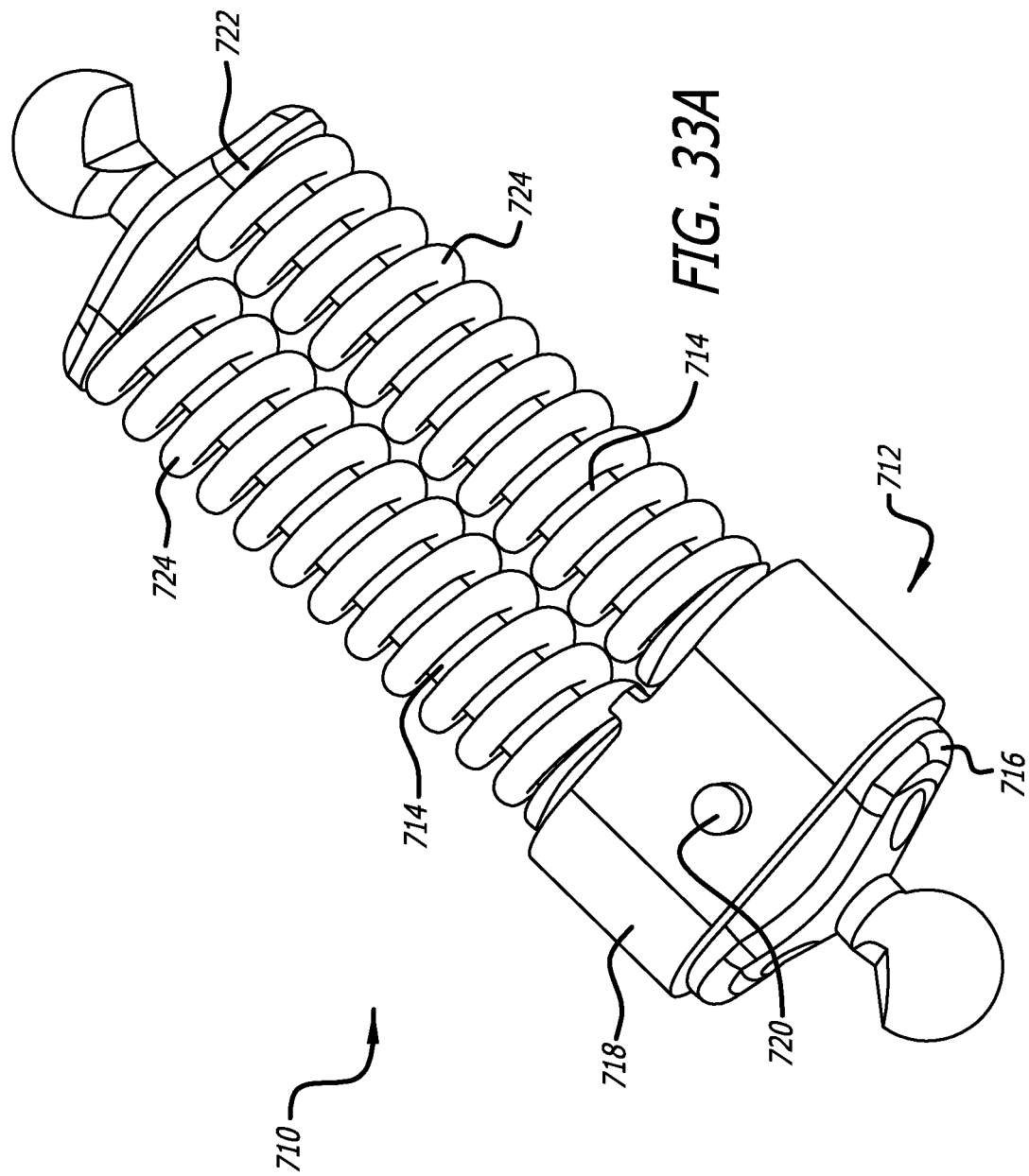
FIG. 33A is a perspective view, depicting an energy absorbing device including an adjustable spacer.
Figure 33B:
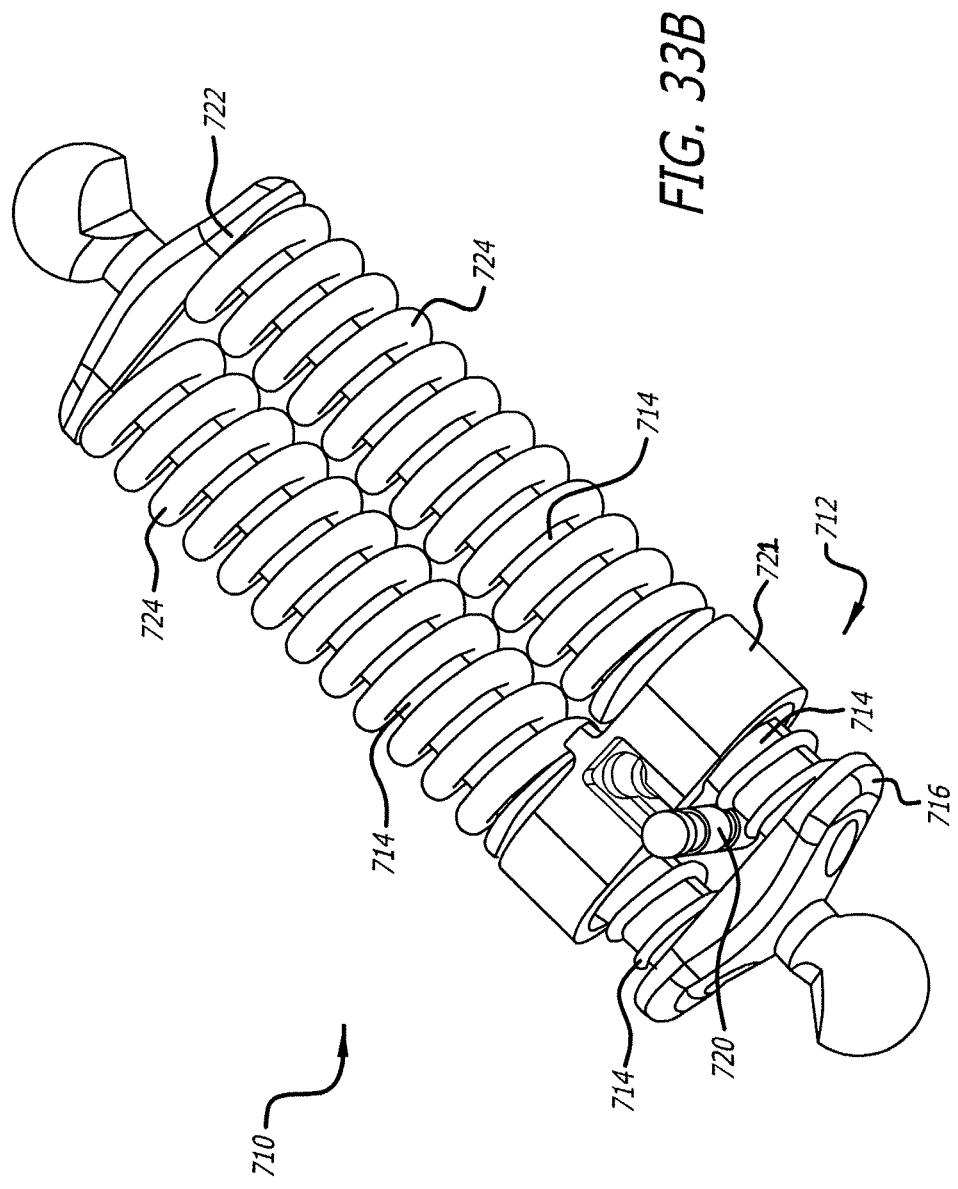
FIG. 33B is a perspective view, depicting the device of FIG. 33A with the spacer removed.
Figure 33C:
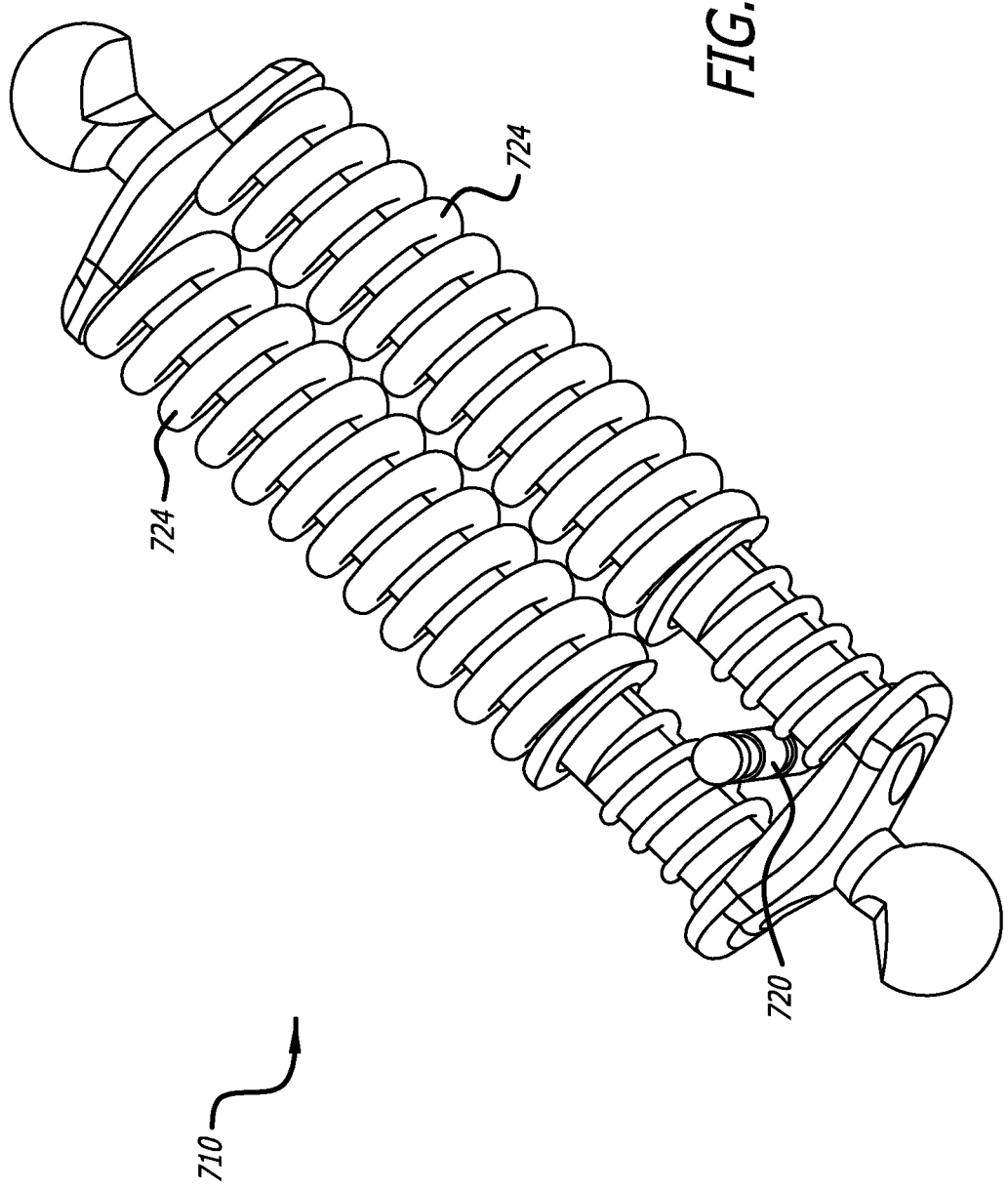
FIG. 33C is a perspective view, depicting the device of FIGS. 33A and 33B with a nut of the adjustable spacer subassembly removed.
Figure 34A:
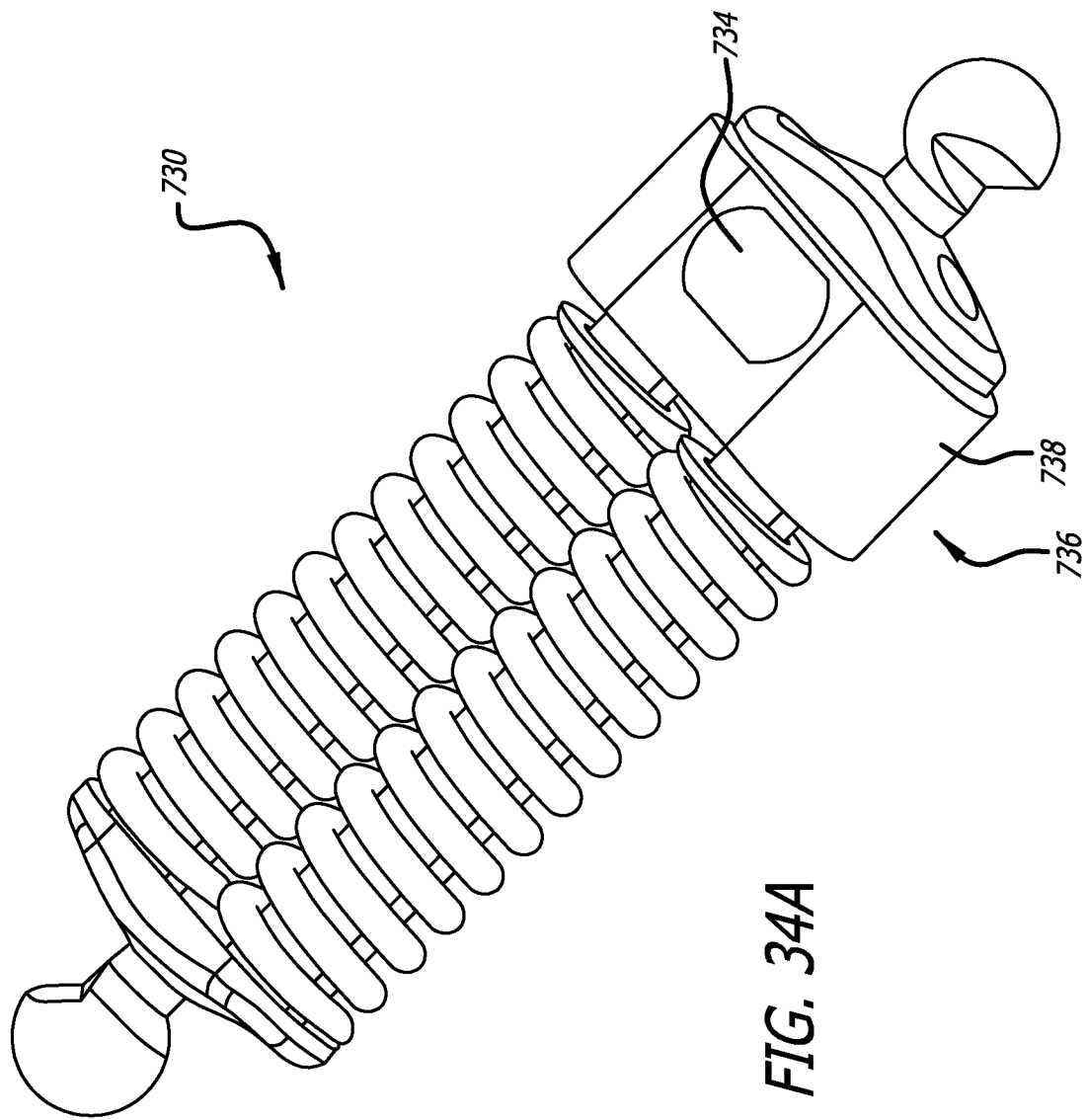
FIG. 34A is a perspective view, depicting an energy absorbing device including adjustable spacer structure.
Figure 34B:
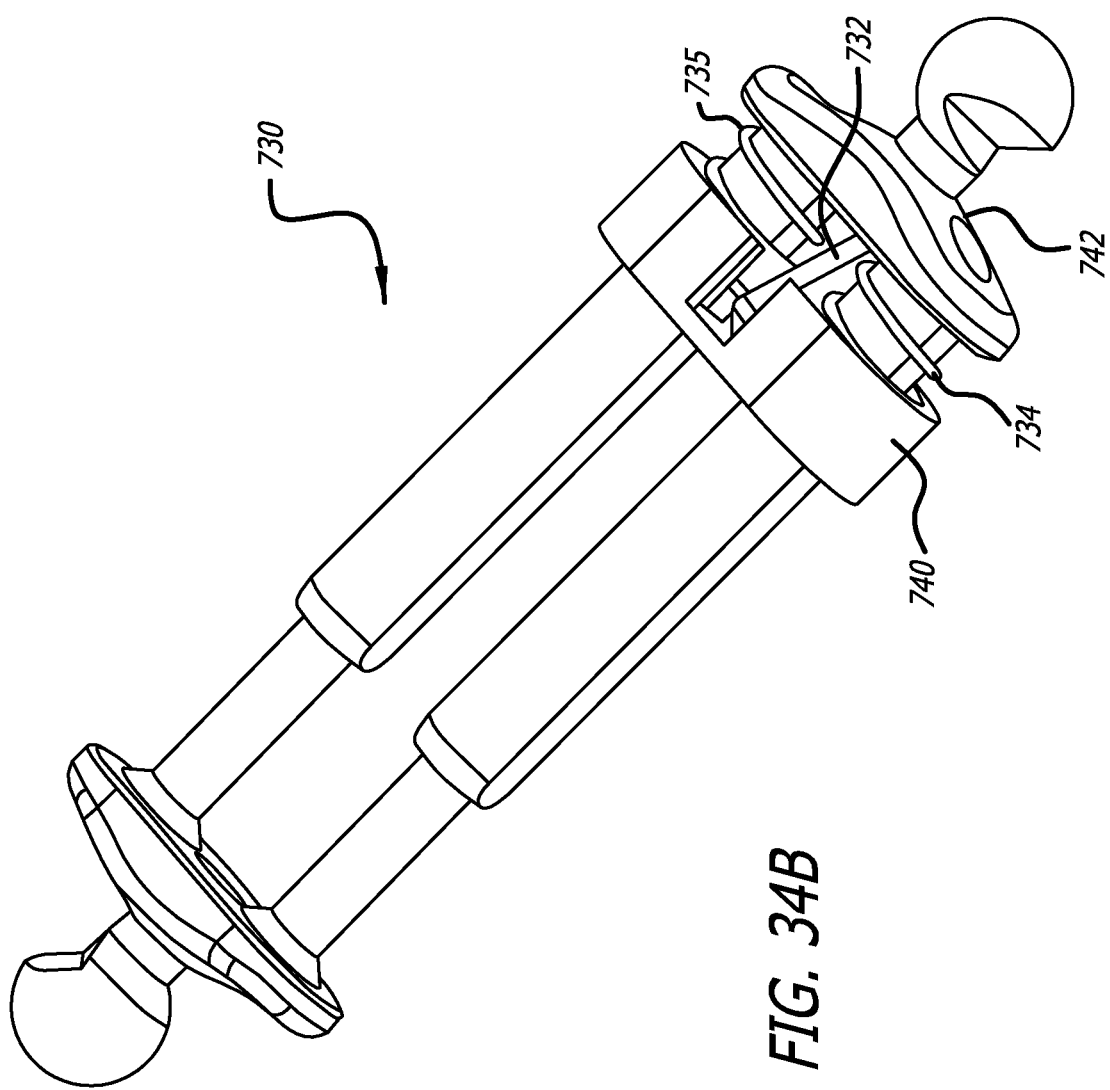
FIG. 34B is a perspective view, depicting the device of FIG. 34A with compression springs removed.
Figure 35A:
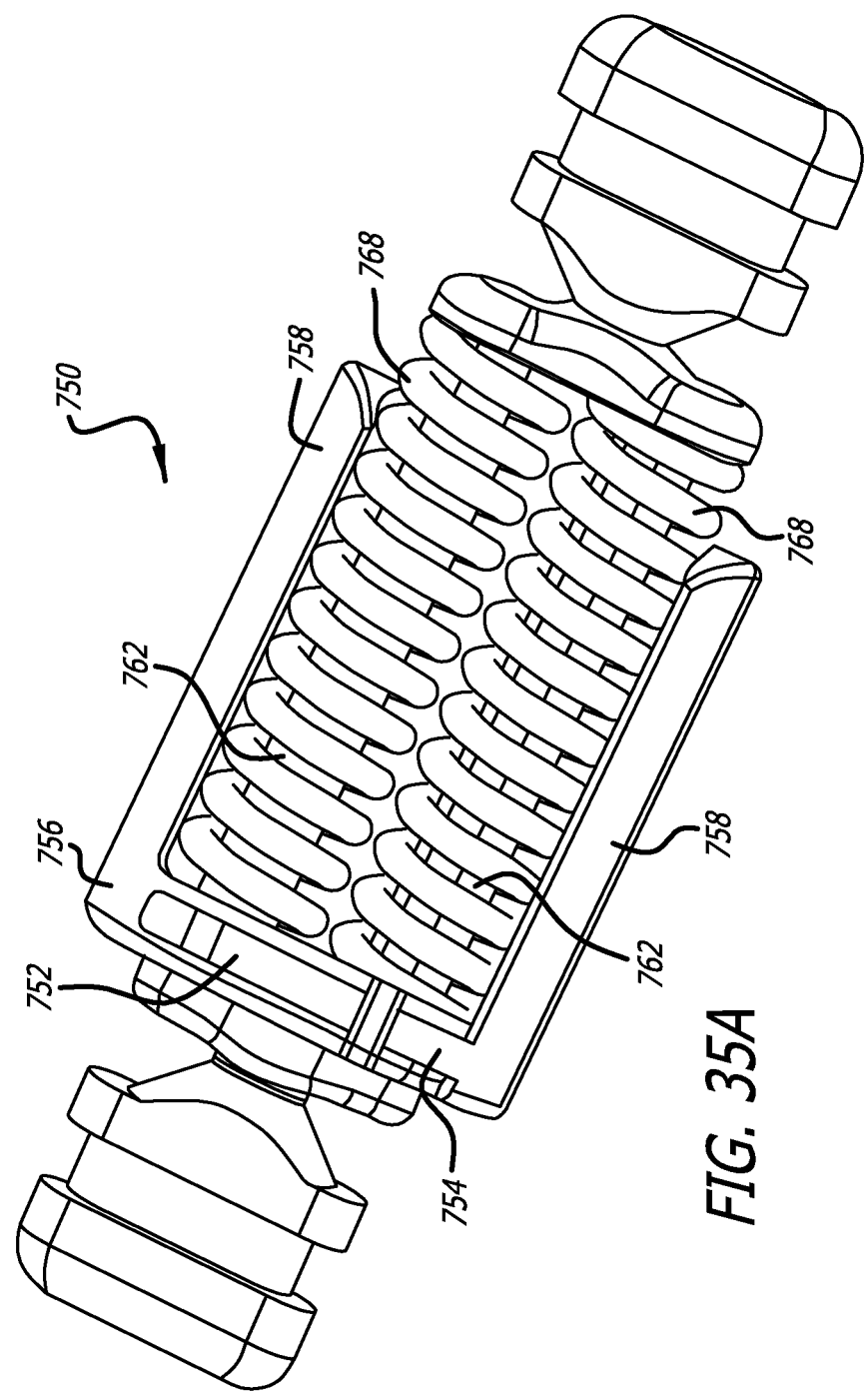
FIG. 35A is a perspective view, depicting an energy absorbing device including adjustable structure interacting with piston shafts.
Figure 35B:
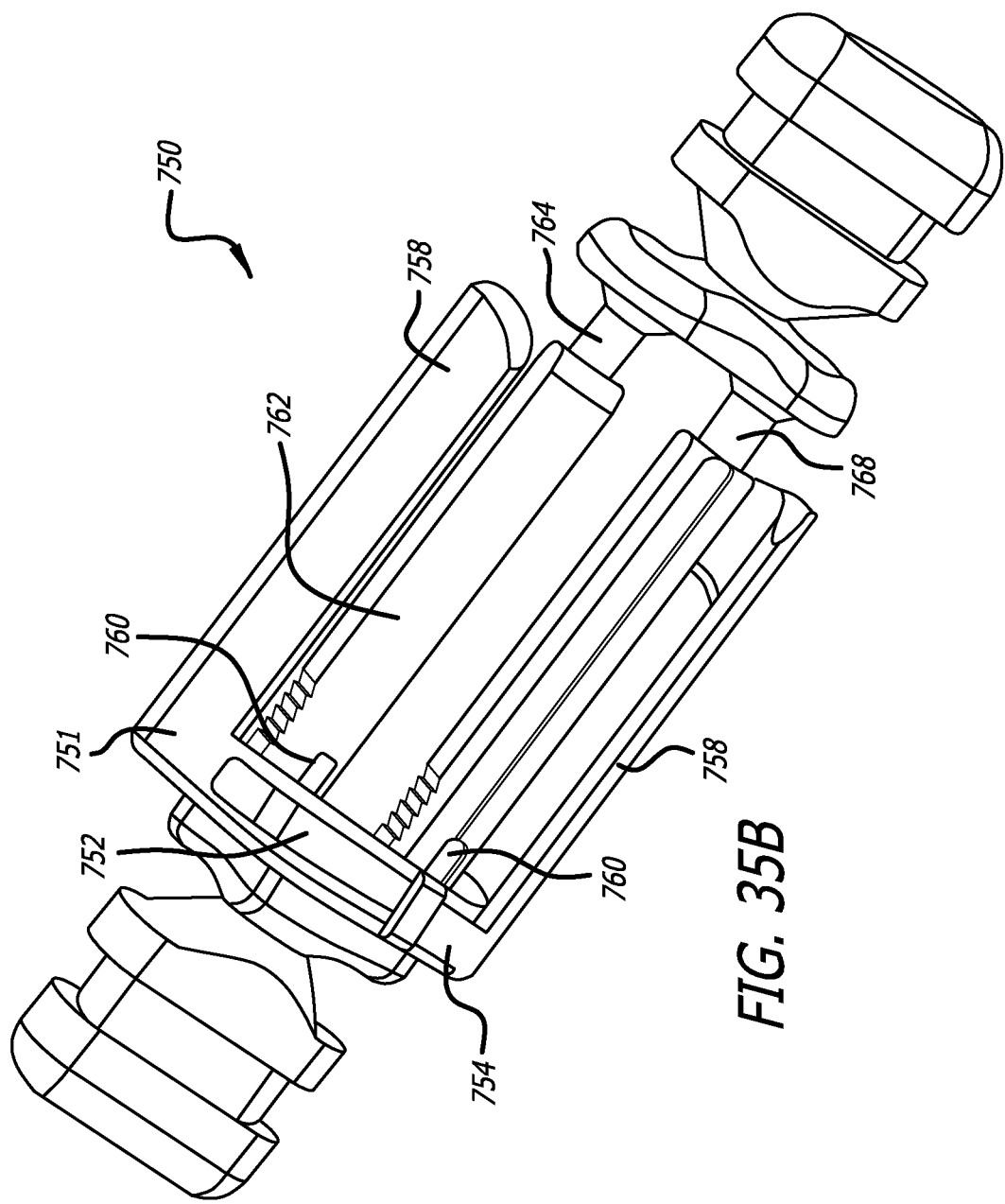
FIG. 35B is a perspective view, depicting the device of FIG. 35A with compression springs removed.
Figure 35C:
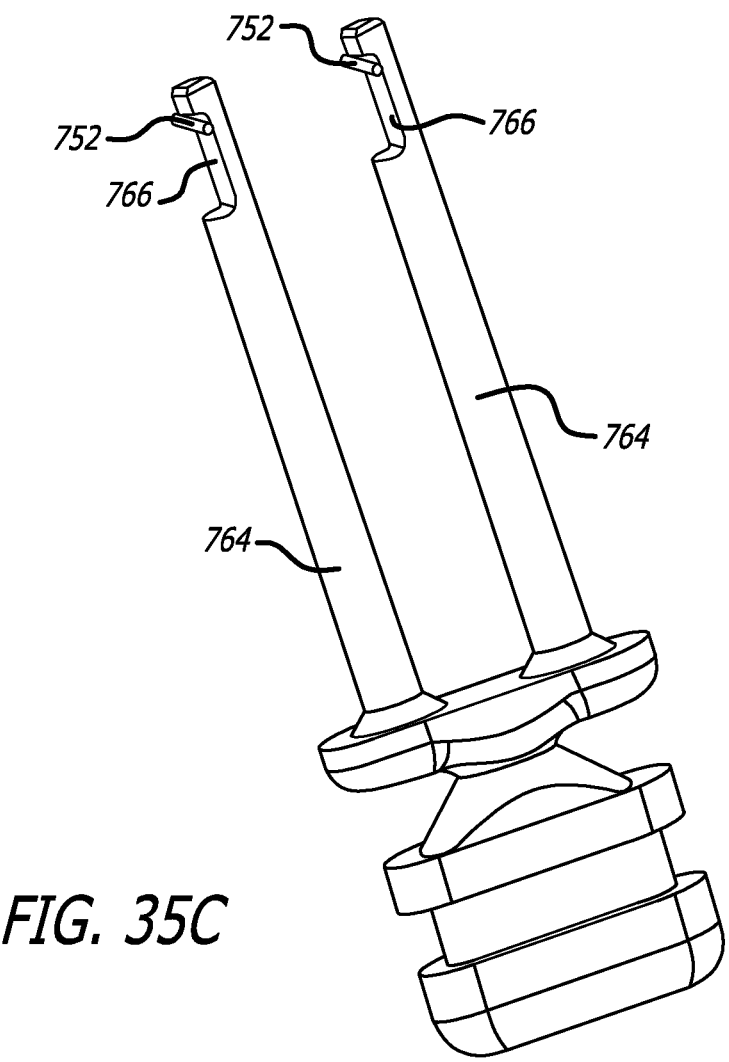
FIG. 35C is a perspective view, depicting the device of FIG. 35B with adjustment core and block structure removed.
Figure 35D:
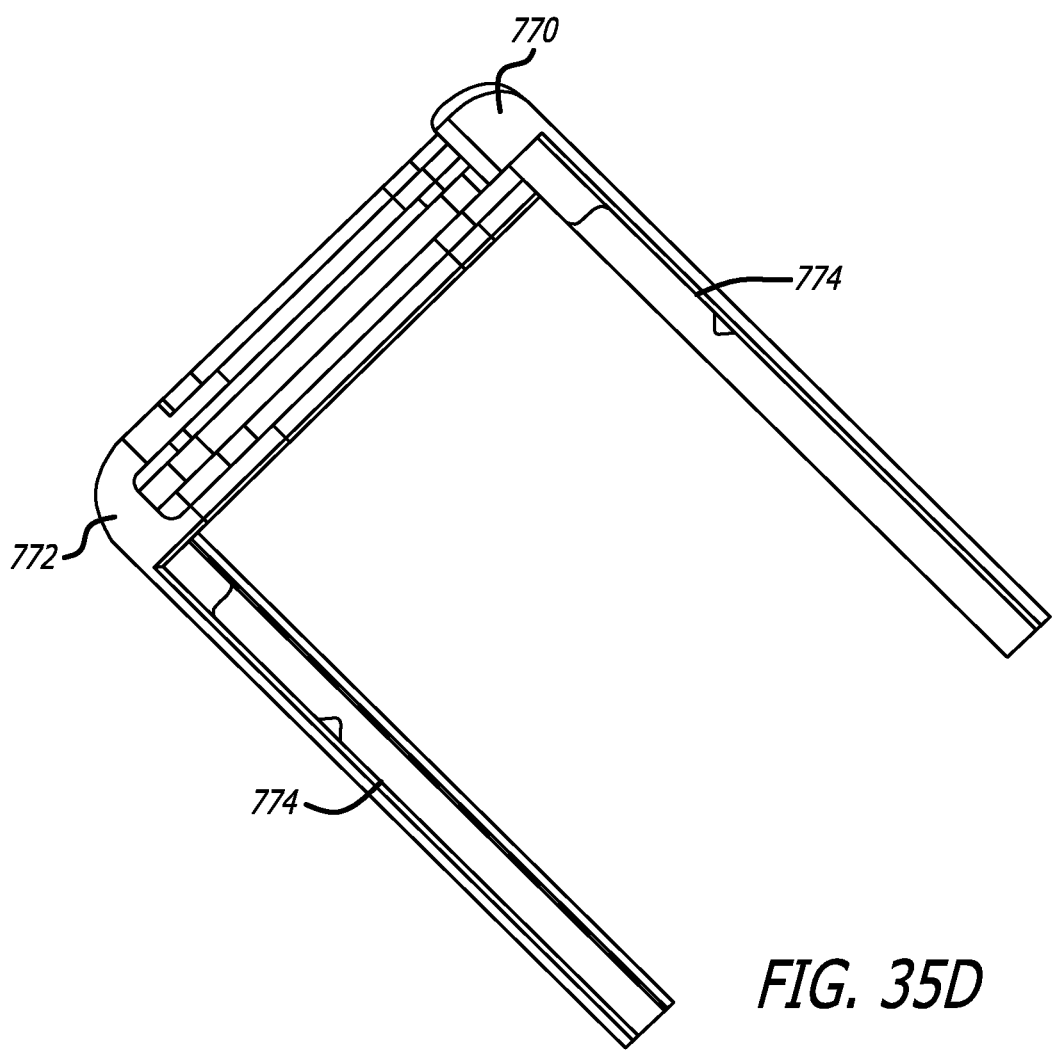
FIG. 35D is a perspective view, depicting an alternate approach to an adjustment assembly.
Figure 35E:
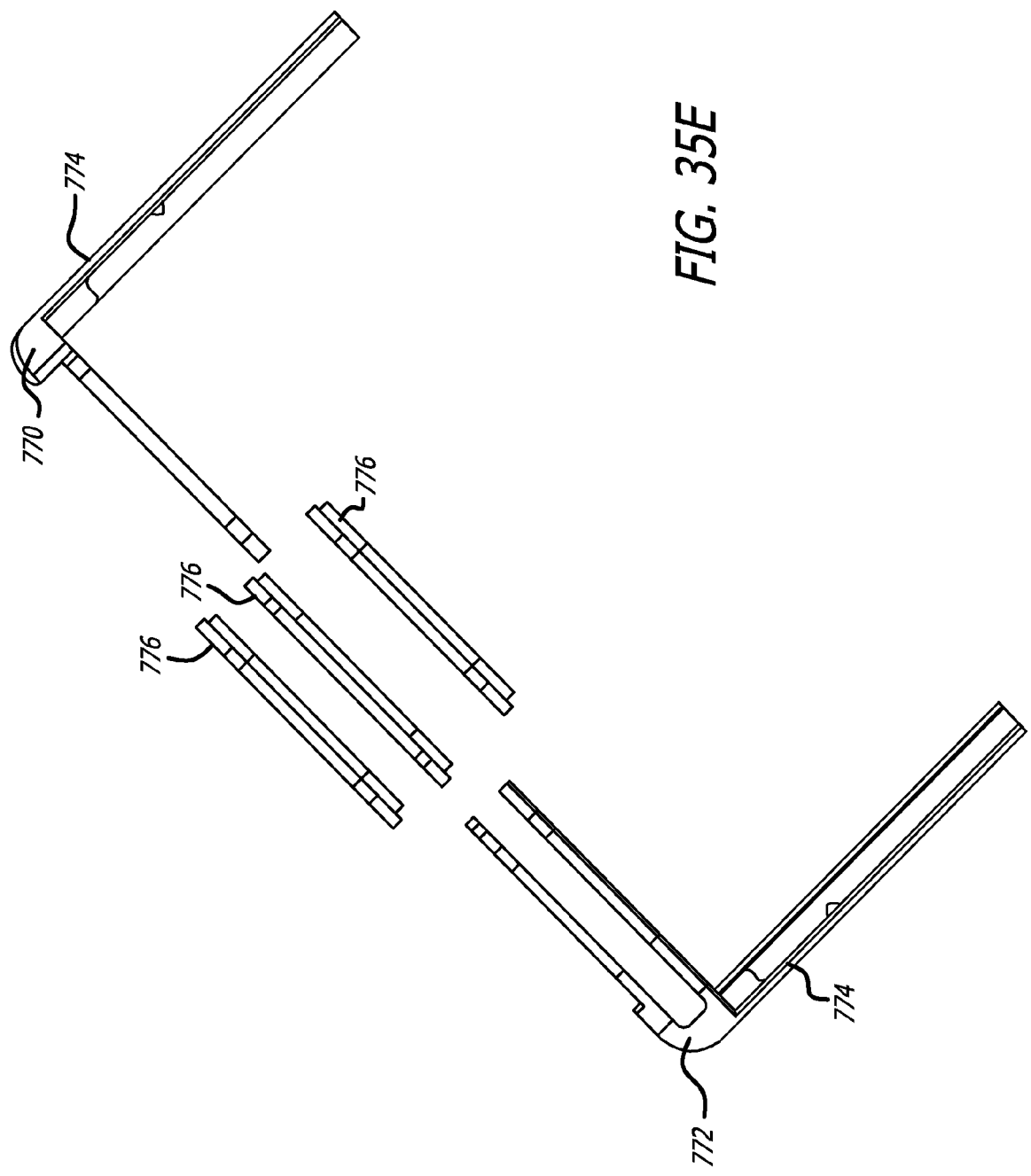
FIG. 35E is an exploded view, depicting the components of FIG. 35D.

An approach to an energy absorbing device 710 including a spring loaded spacer assembly 712 is shown in FIGS. 33A-C. In this approach, rather then relying on a locking engagement with arbor shafts 714, an adjustable spacer 718 of the spacer assembly 712 can be translated and locked in place spaced from the arbor base 716. This approach avoids the removal of material from arbor or link shafts, thus preserving the structural integrity of such members. To accomplish this the spacer 718 with pin 720 extending laterally therethrough is moved towards the piston base as best seen in FIG. 33B. So advancing the spacer 718 results in the pin engaging a slot formed in a spring biased nut 721 configured within the spacer 718. It is to be noted that the spring biased nut 721 is placed in apposition with the compression springs 724. Once the pin 720 is locked within the nut 721, the spacer 718 benefits from the positional relationship between the nut 721 and the springs 724 such that a desired adjustment in energy absorbing capabilities of the spring is achieved. Moreover, it is to be recognized that a compressible dome (not shown) can be configured over the pin to provide a desirable outer profile.

In an approach which relates to the immediately preceding device, rather than a pin, the energy absorbing device 730 can include a lever 732 which is accessible through a compressible dome 734. In this regard, the lever 732 can be held in an inactive state by pins or suture (not shown) after implantation during a time when natural bone and tissue can grow over the energy absorbing device 730 to aid in its fixation at an interventional site. Such pins or sutures can subsequently be removed to activate the device so that desired energy absorbing is accomplished. Structure holding an energy absorbing device in an inactive state can be incorporated into any one of the devices disclosed herein. In the present embodiment, when in an inactive state, the device 730 can be made to move through a normal range of motion with the only force being applied by the device 730 would be that generated by springs 735 of an adjustable spacer assembly 736.

Once the lever 732 is permitted to operate without constraint (such as by removing the sutures or pins), an operator can cause the lever 732 to pivot by applying a force through the dome 734. In its rotated position, the lever 732 which is pivotably supported by a spacer 738, causes the nut 740 housed within the spacer 738 to translate longitudinally away from the arbor base 742. The spacers 736 translate longitudinally with the translation of the nut to thereby bring the compression springs 724 into the load manipulating capabilities of the device 730.

FIGS. 35A-E depict an approach where adjustment structures can be additionally attached to cooperate with piston shafts of an energy absorbing device 750. In this approach, pins 752 (See FIG. 35C) attached to adjustment plates 754, 756 including curved side wings 758 are translatable within slots 760 formed through arbor shafts 762. The piston shafts 764 additionally include cut-outs 766 along which the pins 752 are translatable. Accordingly, in addition to adjusting the position of the blocks 754, 756 along the arbor shafts to adjust the absorber functioning of the compression springs 768, through the engagement of the pins 752 with the piston shafts 764, further adjustment can be achieved.

Moreover, whereas the adjustment assembly can include all of the structures necessary to cooperate with the anchor shaft 762, a contemplated alternative approach is to break the assembly into further sub-components. In this regard reference is made to FIGS. 36D and E which depict five components defining an adjustment assembly which could replace a two-piece approach. Thus, in addition to adjustment plates 770, 772 including curved wings 774, a series of three additional plates 776 can form the adjustment assembly. In this way, the detailed machining or forming which would be necessary to be configured into two pieces can be spread through further components thus streamlining manufacturing procedures.

Figure 36A:
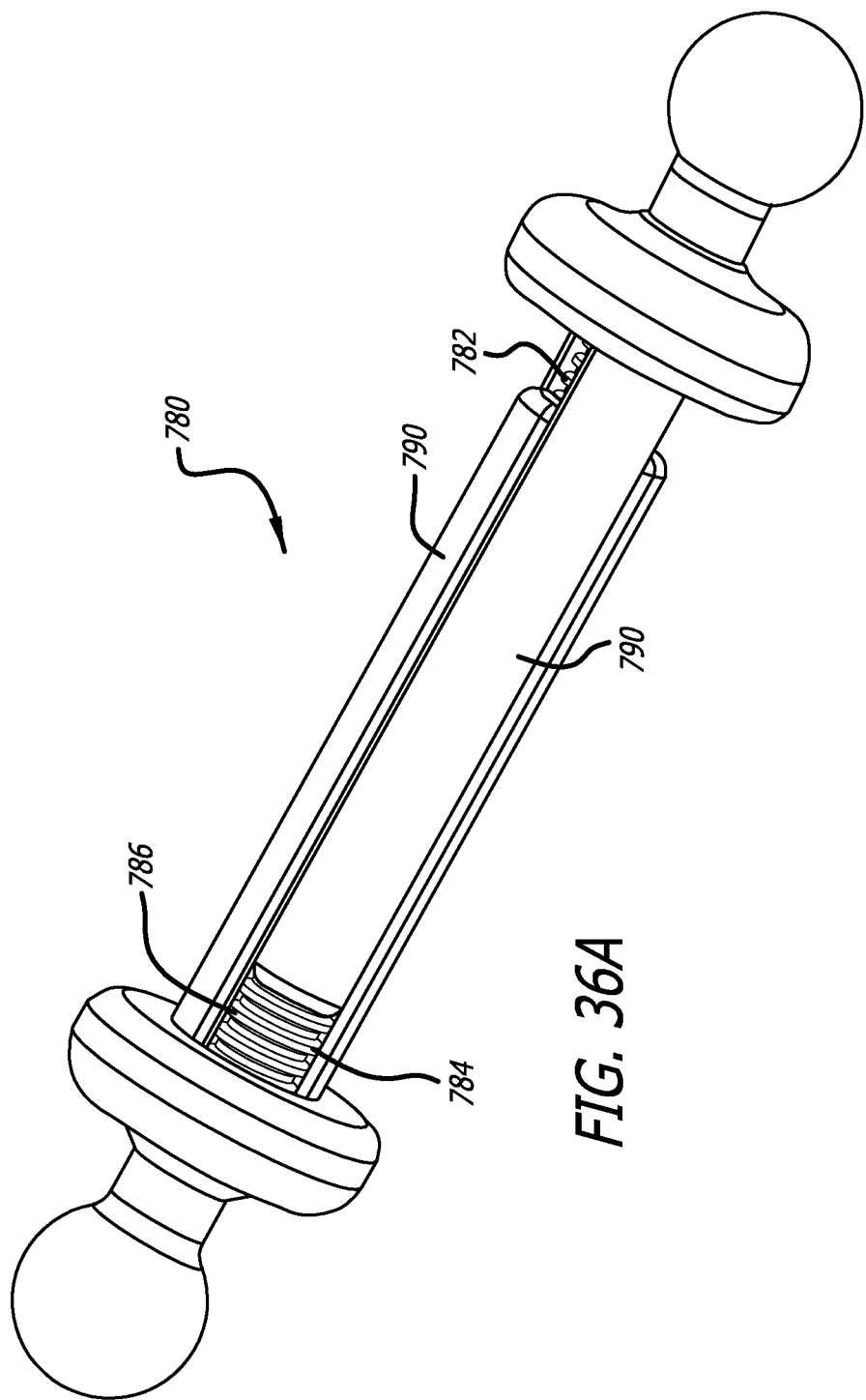
FIG. 36A is a perspective view, depicting an interlocking link with threaded adjustment structure.
Figure 36B:
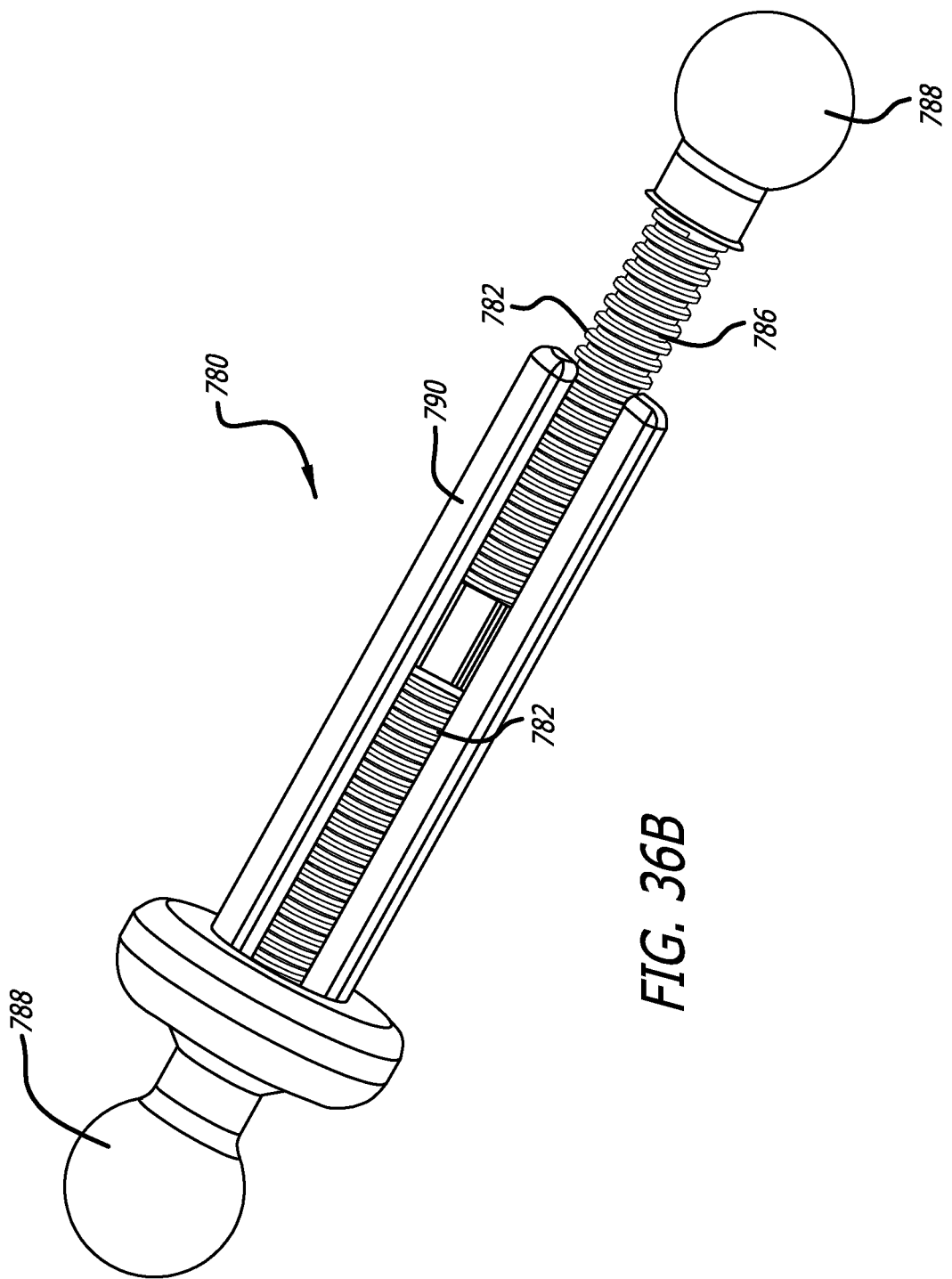
FIG. 36B is a perspective view, depicting the device of FIG. 36A with a slider removed.

Turning now to FIGS. 36A and B, an adjustable, interlocking link device 780 for an energy absorbing device is shown. The link device 780 includes a pair of longitudinally configured shafts 782, 784 having threads 786. The shafts each include ball ends 788 for attaching to a mount of a complete energy absorbing system such as that depicted in FIG. 1A. Configured about the thread shafts 782, 784 are a pair of sliders 790, each of the sliders defining curved arms extending longitudinally. The threaded shafts 782, 784 can be rotated to extend the overall length of the assembly. In this way, rather than relying on an adjustable spacer or other structure to alter the load manipulating ability of an energy absorbing device, adjusting the length of the interlocking link 780 can be employed to accomplish the same. In this regard, the energy absorbing assembly can be configured with one or more tie-rods the ends of which can be accessed to adjust both length of the assembly and effective spring height. For example, one end of a tie-rod can be rotated to adjust length and another end or a second tie-rod can be rotated to alter an amount of pre-loading of a spring.

Figure 37:
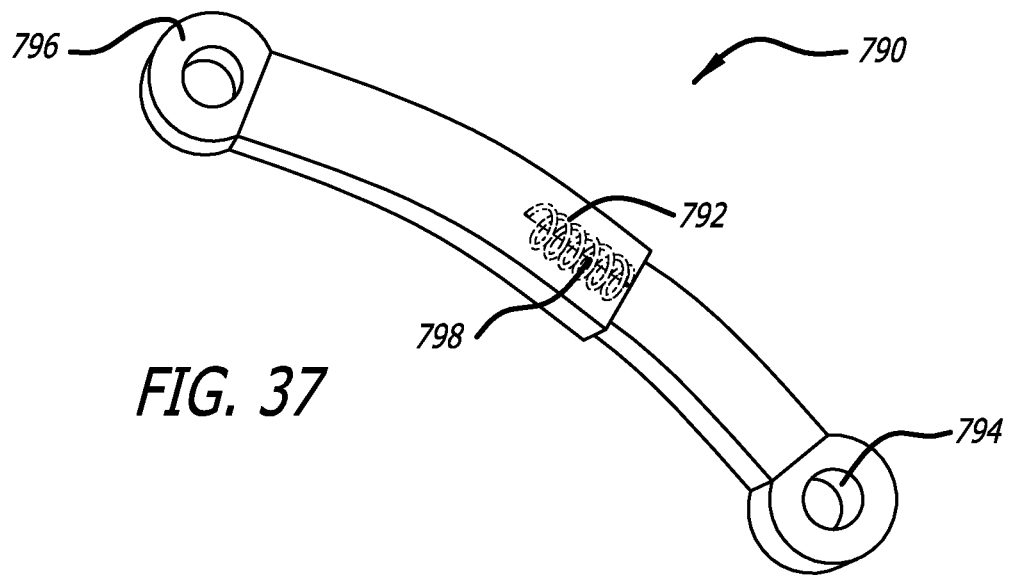
FIG. 37 is a perspective view, depicting an approach to a link which can be intra-operatively or post-operatively activated.

One form of a link assembly 790 can incorporate structure permitting intra-operative or post-operative activation or adjustment (See FIG. 37). While shown for use in the particular link assembly 790 depicted, such or similar structure can be used in each of the approaches disclosed herein. As shown in FIG. 37, a spring 792 can be configured to effectively control positioning and loading of link ends 794, 796. A release wire 798 can be placed into engagement with the spring 792 to retain it in a compressed configuration so as to cause it to be inactivated. Intra-operatively, the release wire 798 can be manipulated to permit the spring 792 to accomplish load manipulation. Alternatively, the release wire 798 can be manipulated by nicking the skin post-operatively to activate the spring 792.

It has also been contemplated that an implantable sensor unit can be configured at an interventional site to detect and keep track of indicators associated with changes in tissue density. One approach is described in WO 2007/098385, the entire contents of which are incorporated by reference. The implantable sensor unit can be configured for wireless communication with an external device and the external device can also be configured for wireless communication with the implantable sensor unit. In particular, the external device is adapted for retrieving, storing, and displaying, in human intelligible form, the tissue density data detected by the implantable sensor unit. The implantable sensor can additionally be affixed to bone of the skeletal system such that it may monitor the bone, adjacent soft tissues, such as muscles, nerves and connective tissues. The sensor may be within or integral to an artificial implant attached to the skeletal system, attached to an artificial implant, adjacent to an artificial implant, or any combination of these locations.

The implantable sensor can include a sensor, a signal processor, a memory unit, a telemetry circuit, and a power source. The sensor can be an acoustic transducer responsive to acoustic signals transmitted through human tissue. Further, it is fully contemplated that the sensor may include other electronics and components adapted for monitoring indicators of changes in tissue structure including deterioration and/or healing. The disclosed sensor has applications throughout the skeletal system including the hip, knee, ankle, elbow and jaw joints and load bearing bones such as the skull and long bones. Such disclosed sensors are useful to evaluate tissue properties and detect changes to tissue in the skeletal system. The sensor also has a particular application with respect to detecting changes in bone density as it relates to osteoporosis and the sensor can detect tissue density changes with respect to tissue around fixation implants, joint implants, or any other type of implant. Moreover, an acoustic sensor may also be used to detect changes in viscosity. Thus, the sensor may be utilized to listen for changes in bodily systems and organs and alert healthcare professionals to any impending or potential problems.

Accordingly, a number of embodiments are described above for adjusting the amount of load an energy absorbing device can manipulate to help reduce pain in a patient. These embodiments can be used in any energy absorbing system for use throughout the body but have clear applications to articulating body structures such as joints. Moreover, features and structures of certain of the disclosed embodiments can be incorporated into other disclosed embodiments by replacing structure or complementing structure.

It will be apparent from the foregoing that, while particular forms of the embodiments have been illustrated and described, various modifications can be made without parting from the spirit and scope of the invention.

We claim:

1. An implantable system for manipulating energy transferred by members defining a knee joint, the members defining a natural path of motion, comprising:
   a first attachment structure configured to be attached to a first member of the knee joint,
   a second attachment structure configured to be attached to a second member of the knee joint, and
   an adjustable energy absorbing device attached to the first attachment structure and second attachment structure, the adjustable energy absorbing device includes an energy absorbing component configured about a shaft and a spacer assembly configured to be translated along and longitudinally fixed onto the shaft to alter an amount of load the energy absorbing component accommodates.

2. The system of claim 1, wherein the spacer assembly is biased by a spring.

3. The system of claim 1, wherein the energy absorbing component includes an elastomeric member.

4. An implantable system for manipulating energy transferred by members defining a joint, comprising:
   a first attachment structure configured to be attached to a first member of the joint;
   a second attachment structure configured to be attached to a second member of the joint; and
   an adjustable energy absorbing device attached to the first attachment structure and second attachment structure, the adjustable energy absorbing device includes an energy absorbing component configured about a shaft and a spacer assembly configured to be translated along the shaft to alter functioning of the energy absorbing component,
   wherein the spacer assembly includes a nut and a transversely configured pin, the nut including a keyed recess for lockingly engaging with the pin.

5. The system of claim 4, wherein the pin extends through a spacer of the spacer assembly and is accessible through a domed cover.

6. The system of claim 5, wherein the nut is biased by a spring and the spacer of the spacer assembly is locked in relation to the nut upon advancement of the pin within the keyed recess of the nut.

7. An implantable system for manipulating energy transferred by members defining a knee joint, the members defining a natural path of motion, comprising:
   a first attachment structure configured to be attached to a first member of the knee joint;
   a second attachment structure configured to be attached to a second member of the knee joint; and
   an adjustable energy manipulation device attached to the first attachment structure and second attachment structure, the adjustable energy manipulation device includes an arbor being slidingly engaged with a piston, an assembly disposed over a shaft of the arbor or piston being configured to lock onto one of a plurality of positions along a length of the shaft, and a compression spring disposed over the shaft between the assembly and a base of the piston;
   wherein the assembly can be repositioned and locked on the arbor shaft to adjust the amount of load the energy manipulation device can manipulate by changing the compression of the spring.

8. The system of claim 7, wherein the joint is a knee joint affected with osteoarthritis and variable amounts of energy absorption occurs while the members follow a path of motion.

9. The system of claim 7, wherein the adjustable energy manipulation device includes a first spring and a second spring disposed over a first arbor shaft and a second arbor shaft, respectively.

10. The system of claim 7, wherein the assembly is a spring loaded stop collar.

11. The system of claim 1, wherein there is less energy absorption occurring through greater flexion of members defining the joint.

12. The system of claim 7, wherein there is less energy absorption occurring through greater flexion of members defining the joint.

13. The system of claim 1, wherein the first and second attachment structures are configured to be attached to bones on opposite sides of a knee joint and the energy manipulation device is configured to be located across the knee joint.

14. The system of claim 1, wherein the energy absorbing component includes as least two side by side springs each configured about a shaft and the spacer assembly is configured to be translated along the shafts.

15. The system of claim 14, wherein the at least two side by side energy absorbing components are arranged about the shafts in a side by side, parallel, non-coaxial arrangement.

16. The system of claim 4, wherein the first and second attachment structures are configured to be attached to bones on opposite sides of a knee joint and the energy manipulation device is configured to be located across the knee joint.

17. The system of claim 7, wherein the energy manipulation device is configured to be located across the knee joint.

* * * * *